United States Patent [19]
Denny et al.

[11] Patent Number: 6,130,237
[45] Date of Patent: Oct. 10, 2000

[54] CONDENSED N-ACLYINDOLES AS ANTITUMOR AGENTS

[75] Inventors: William A. Denny; Moana Tercel; Graham J. Atwell, all of Auckland, New Zealand

[73] Assignee: Cancer Research Campaign Technology Limited, London, United Kingdom

[21] Appl. No.: 09/266,966

[22] Filed: Mar. 12, 1999

Related U.S. Application Data

[63] Continuation of application No. PCT/NZ97/00117, Sep. 12, 1997.

[30] Foreign Application Priority Data

Sep. 12, 1996 [GB] United Kingdom .................... 9619082
Apr. 10, 1997 [GB] United Kingdom .................... 9707394

[51] Int. Cl.$^7$ .................................................. C07D 209/10
[52] U.S. Cl. .......................... 514/411; 548/427; 548/433; 548/450
[58] Field of Search .................... 548/427, 433, 548/450; 514/411

[56] References Cited

FOREIGN PATENT DOCUMENTS

| 0 351 865 | 1/1990 | European Pat. Off. . |
| 0 415 731 A2 | 3/1991 | European Pat. Off. . |
| WO 88/04659 | 6/1988 | WIPO . |
| WO 88/07378 | 10/1988 | WIPO . |
| WO 91 16324 | 10/1991 | WIPO . |
| WO 93/08288 | 4/1993 | WIPO . |
| WO 93/11099 | 6/1993 | WIPO . |
| WO 94/02450 | 2/1994 | WIPO . |
| WO 95/12678 | 5/1995 | WIPO . |
| WO 97 07097 | 2/1997 | WIPO . |
| WO 97 12862 | 4/1997 | WIPO . |
| WO 97 32850 | 9/1997 | WIPO . |

OTHER PUBLICATIONS

G. J. Atwell et al, "Synthesis and cytotoxicity of amino analogues of the potent DNA alkylating agent seco-o–CBI–TMI", Bioorg, Med. Chem. Lett., vol. 7, No. 12, 1997, pp. 1493–1496.

M. Tercel et al, "Nitrogen and sulfur analogues of the seco–CI alkylating agent: synthesis and cytotoxicity", Bioorg. Med. Chem. Lett., vol. 6, No. 22, 1996, pp. 2735–2740.

Nitiss et al., "A Temperature Sensitive Topoisomerase II Allele Confers Temperature Dependent Drug Resistance on Amsacrine and Etoposide: A Genetic System . . . ", Cancer Research 53, 89–93, Jan. 1, 1993.

Knox et al., "Bioactivation of CG 1954: Reaction of the Active 4–Hydroxylamino Derivative With Thioesters . . . " Biochemical Pharmacology, vol. 42, No. 9, pp. 1691–1697, 1991.

Knox et al., "The Bioactivationof 5–(Aziridin–1–YL)–2, 4–Dinitrobenzamide (CB1954)—II . . . " Biochemical Pharmacology, vol. 44, No. 12, pp. 2297–2301, 1992.

Huber et al., "Retroviral–mediated Gene Therapy for the Treatment of Hepatocellular Carcinoma: . . . ", Proc. Natl. Acad. Sci. USA, vol. 88, pp. 8039–8043, Sep. 1991.

Engelhardt et al., "Direct Gene Transfer of Human CFTR into Human Bronchial Epithelia of Xenografts with E1–deleted Adenoviruses", Nature Genetics, vol. 4, May 1993, pp. 27–33.

Mauger et al., "Self–Immolative Prodrugs: Candidates for Antibody–Directed Enzyme Prodrug Therapy . . . ", J. Med. Chem. 1994, 37, 3452–3458.

Lefebvre et al., "Oxytocin Gene Expression in Rat Uterus", Science, vol. 256, Jun. 12, 1992.

Boger et al., Duocarmycin–Pyrindamycin DNA Alkylation Properties and Identification, Synthesis, and Evaluation of Agents Incorporating the Pharmacophore of the Duocarmycin–Pyrindamycin Alkylation Subunit . . . , J. Am. Chem. Soc. 1990, 112, 8961–8971.

Boger et al., "Synthesis of N–(Phenylsulfonyl)–CI, N–((ter-t–Butyloxy)carbonyl)–CI, CI–CDPI1, and CI–CDPI2: CC–1065 Functional Analogues Incorporating the Parent . . . ", J. Am. Chem. Soc. 1990, 112, 5230–5240.

Primary Examiner—Robert Gerstl
Attorney, Agent, or Firm—Nixon & Vanderhye P.C.

[57] ABSTRACT

The invention provides compounds of general formula (I), wherein: X is halogen or $OSO_2R$, where R represents H or is unsubstituted or hydroxy-or amino-substituted lower alkyl; Y is a nitro or amine group or a substituted derivative thereof; W is selected from the structures of formulae (Ia, Ib or Ic), where E is —N═ or —CH═, G is O, S, or NH, and Q is either up to three of R, OR, NRR, $NO_2$, CONHR, NHCOR or NHCONHR, or is an additional group of formulae (Ia, Ib or Ic) and HET represents a 5- or 6-membered carbocycle or heterocycle; and A and B collectively represent a fused benzene or 2-$CO_2R$ pyrrole ring. In one embodiment, the group Y is an amine derivative substituted by a group which is a substrate for a nitroreductase or carboxypeptidase enzyme such that one of said enzymes is able to bring about removal of that group.

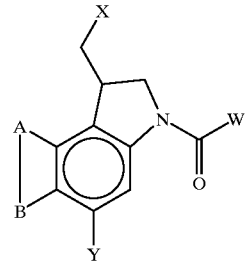

(I)

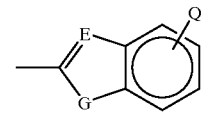

(Ia)

(Ib)

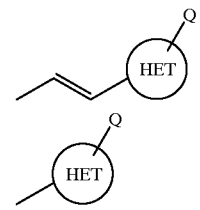

(Ic)

18 Claims, 5 Drawing Sheets

CONDENSED N-ACLYINDOLES AS ANTITUMOR AGENTS

This is a continuation of PCT application No. PCT/NZ97/00117, filed Sep. 12, 1997.

The present invention relates to novel amino analogues of the general class of cyclopropylindoles and their seco precursors, and is particularly concerned with the use of these compounds as prodrugs for antibody-directed enzyme-prodrug therapy (ADEPT) and gene-directed enzyme-prodrug therapy (GDEPT) for cancer.

BACKGROUND TO THE INVENTION

The use of prodrugs represents a clinically very valuable concept in cancer therapy since, particularly where the prodrug is to be converted to an anti-tumor agent under the influence of an enzyme that is linkable to a monoclonal antibody that will bind to a tumour associated antigen, the combination of such a prodrug with such an enzyme monoclonal/antibody conjugate represents a very powerful clinical agent. This approach to cancer therapy, often referred to as "antibody directed enzyme/prodrug therapy" (ADEPT) is disclosed in WO88/07378.

A further therapeutic approach termed "virus-directed enzyme prodrug therapy" (VDEPT) has been proposed as a method for treating tumour cells in patients using prodrugs. Tumour cells are targeted with a viral vector carrying a gene encoding an enzyme capable of activating a prodrug. The gene may be transcriptionally regulated by tissue specific promoter or enhancer sequences. The viral vector enters tumour cells and expresses the enzyme, in order that a prodrug is converted to an active drug within the tumour cells (Huber et al., Proc. Natl. Acad. Sci. USA (1991) 88, 8039). Alternatively, non-viral methods for the delivery of genes have been used. Such methods include calcium phosphate co-precipitation, microinjection, liposomes, direct DNA uptake, and receptor-mediated DNA transfer. These are reviewed in Morgan & French, Annu. Rev. Biochem., 1993, 62; 191. The term "GDEPT" (gene-directed enzyme prodrug therapy) is used to include both viral and non-viral delivery systems.

Cyclopropylindole compounds are a class of highly potent antitumour antibiotics with the natural products CC-1065 (V. L. Reynolds et al., J. Antibiot., 39, 1986, 319–314) and the duocarmycins (D. L. Boger, Pure & Appl. Chem., 66, 1994, 837–844), having IC50's in the low pM range. These compounds bind in the minor groove of DNA and alkylate in a highly sequence selective manner at N-3 of adenine (D. L. Boger et al., Tetrahedron, 47, 1991, 2661–2682). Studies with compounds that model the alkylation subunit have shown that the more stable open chain seco precursors are as potent as the cyclopropylindole compounds. Further, ring closure is not essential for DNA alkylation, and there is some measure of electronic control by the both the 6-substituent (D. L. Boger et al., J. Am. Chem. Soc., 113, 1991, 3980–3983) and the 1-substituent (D. L. Boger and W. Yun, J. Am. Chem. Soc., 116, 1994, 5523–5524) on the rate of alkylation.

A number of synthetic analogues of the natural products have been prepared in which the oxygen is protected as a carbamate that must be cleaved (by non-specific enzymatic hydrolysis) for activity. These compounds include carzelesin (L. H. Li et al., Cancer Res., 52, 1992, 4904–4913) and KW-2189 (E. Kobayashi et al., Cancer Res., 54, 1994, 2404–2410) which show anticancer activity against a range of human tumours and are in clinical trial. These compounds have the structures A and B respectively:

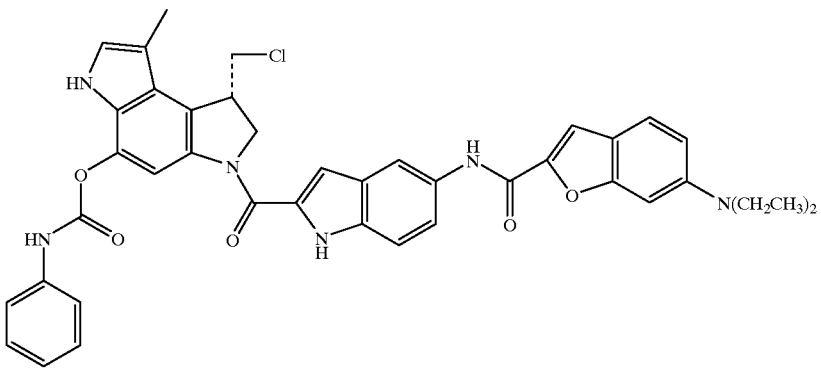

(A)

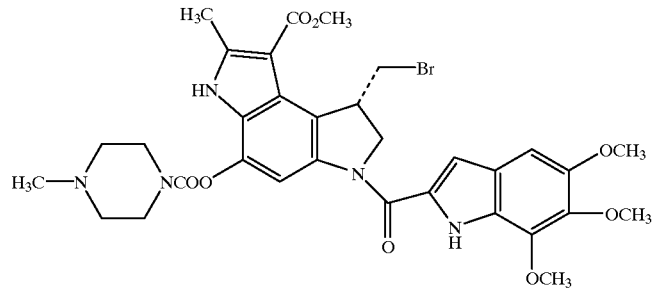

(B)

Further analogues of a similar type are disclosed in WO88/04659 and WO91/16324.

DISCLOSURE OF THE INVENTION

In one aspect, the present invention relates to the new class of seco cyclopropylindoles, represented by formula (I):

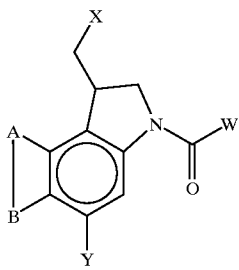

(I)

wherein:

X is halogen or $OSO_2R$, where R represents H or lower alkyl (up to four carbon atoms) optionally substituted with hydroxyl or amino groups, the amino groups being optionally substituted by one or two $C_{1-4}$alkyl groups;

Y is $NO_2$, NHOH, $N_3$, NHR, NRR, N=NR, N(O)RR, $NHSO_2R$, N=NPhR, SR or SSR, where Ph is a benzene ring and R is defined as above, but that in the case where Y is N=NR or SSR, then R can also be another moiety of general formula I (i.e. a symmetrical disulfide or azo compound);

W is selected from the structures of formulae (Ia, Ib or Ic):

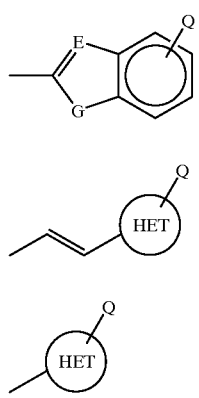

(Ia)

(Ib)

(Ic)

where E is —N= or —CH=, G is O, S, or NH, and Q is either up to three of R, OR, NRR, $NO_2$, CONHR, NHCOR or NHCONHR, where R is defined as above (which may be the same or different when Q is two or three), or is an additional group of formulae (Ia, Ib or Ic) and HET represents a 5- or 6-membered carbocycle or heterocycle containing up to two atoms selected from N, O or S;

A and B collectively represent a fused benzene or 2-$CO_2R$ pyrrole ring, where R is as defined above; or a physiologically functional derivative thereof.

In a second aspect, the present invention relates to the class of compounds represented by formula (II):

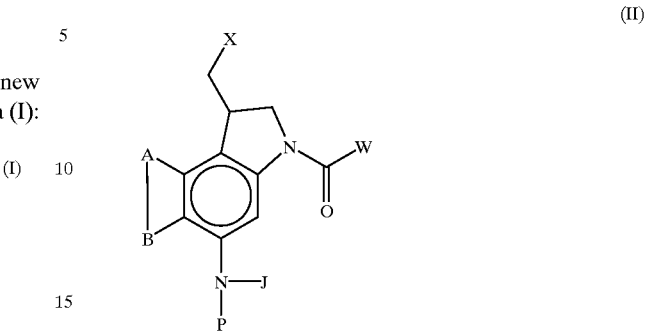

(II)

where A, B, E, G, Q, R, W and X are represented above for general formulae I, Ia, Ib or Ic, J is OH or R (where R is as defined above), and P is a group which is a substrate for a nitroreductase or carboxypeptidase enzyme such that one of said enzymes is able to bring about removal of the group P.

Group P may be selected from moieties of the formulae (IIa), (IIb), (IIc) or (IId):

  (IIa)

  (IIb)

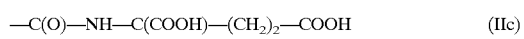  (IIc)

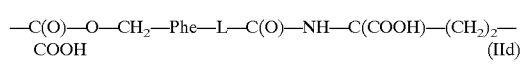  (IId)

wherein each occurrence of Z is independently H or Me, n is 1 or 2, Ph is a phenyl moiety substituted in the moiety of (IIa) by a nitro group at the 2-position, and substituted in the moiety of (IIb) by a nitro group in the 2- or 4-position, Phe is a phenylene ($C_6H_4$) ring in which the group —L, which is O or NH, is para to the group —O—$CH_2$, the groups Ph and Phe being further optionally substituted by a group $R^1$ which may be a group R, CONHR, NHCOR, NHR, OR or $SO_2R$, where R is defined as above; or a physiologically functional derivative thereof.

It is recognised that certain compounds of general formulae I and II may exist in one of two different enantiomeric or diastereomeric forms. In such cases it is to be understood that general formulae I and II represent either enantiomeric or diastereomeric form or a mixture of both.

A halogen group means a fluoro, chloro, bromo or iodo group. A chloro group is preferred. Preferred compounds of formulae (I) and (II) include those in which X represents Cl. Preferred compounds include those in which W represents Ia, E represents —CH=, G represents NH, and Q represents three Ome groups. Compounds in which P represents formulae (IIb) are also preferred. $R_1$ desirably represents H or CONHR, where R is defined as above. Compounds in which the $CH_2X$ substituent is in the S configuration are also preferred.

Examples of compounds of formula (I) include those of formula (III):

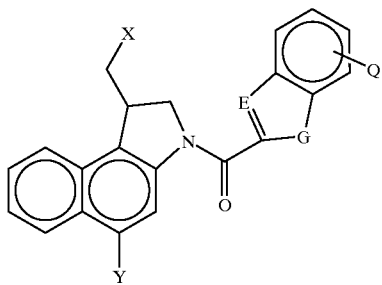

(III)

where X, Y, E, G and Q are defined as above, and those of formula (IV):

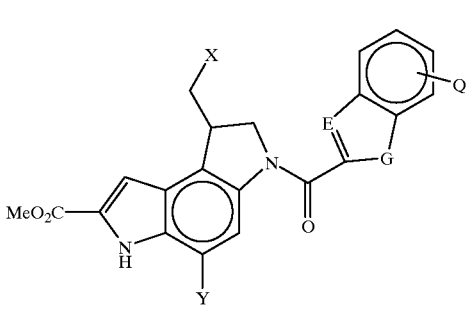

(IV)

where X, Y, E, G and Q are defined as above.

It is preferred that when P is a group (IIb), the nitro group is in the 4-(para) position.

In another aspect, the present invention relates to the use of the compounds of formulae (I) or (II) as anticancer drugs. The compounds may be used for the selective killing of oxic and hypoxic tumour cells in methods of treatment of cancers, for example leukemias and particularly solid cancers including breast, bowel and lung tumours, including small cell lung carcinoma.

In a further aspect, the present invention relates to the use of the compounds of formula (II), in conjunction with nitroreductase or carboxypeptidase enzymes (for example, the aerobic NR2 nitroreductase isolated from E. coli) in methods of ADEPT and GDEPT therapy.

The invention also provides pharmaceutical compositions comprising a compound of the formula (I) or the formula (II), together with a pharmacologically acceptable carrier or diluent.

DESCRIPTION OF THE DRAWINGS

In FIGS. 1–4, small roman numerals on the figures refer to reaction conditions which are described in more detail in the accompanying description and examples. However in outline, the conditions are summarised as follows:

FIG. 1:
(i) $NaHCO_3$ (1 equiv), then 4-MeObenzyl chloride.
(ii) 70% $HNO_3$/AcOH.
(iii) $(Tf)_2O/NEt_3/CH_2Cl_2$.
(iv) $CH_2(COOMe)_2/K_2CO_3/DMF$.
(v) $CF_3COOH/PhOCH_3$.
(vi) $SOCl_2/DMF$ (1:1)/py/$NaN_3/CH_2Cl_2$.
(vii) Toluene/reflux.
(viii) $BH_3.DMS/THF$/reflux.
(ix) $(BOC)_2O$/N-methylimidazole.
(x) NaOMe/MeOH/THF/20° C., then $CF_3COOH$.
(xi) DIBAL/THF.
(xii) MsCl/py, then LiCl/DMF.
(xiii) HCl, then EDCI.HCl/5,6,7-TMI-2-carboxylic acid.
(xiv) $H_2/PtO_2/THF$.
FIG. 2:
(i) $HS(CH_2)_3SH/BF_3.OEt_2$
(ii) $NaHCO_3$, then 4-MeObenzyl chloride
(iii) $(CF_3SO_2)_2O/Et_3N$
(iv) $CH_2(CO_2Me)_2/NaH$
(v) $CF_3CO_2H$
(vi) $(PhO)_2PON_3/Et_3N$
(vii) $BH_3.Me_2S$
(viii) $(BOC)_2O/DMAP$
(ix) NaOMe
(x) DIBAL
(xi) $Hg(ClO_4)_2$
(xii) $N_3CH_2COOMe/NaOMe$
(xiii) xylene/heat
(xiv) $Pph_3/CCl_4$
(xv) step xiii of Scheme 1
(xvi) step xiv of Scheme 1
FIG. 3:
(i) $NaHCO_3$, then 4-MeObenzyl chloride
(ii) $(CF_3SO_2)_2O/Et_3N$
(iii) $CH_2(CO_2Me)_2/NaH$
(iv) $CF_3CO_2H$
(v) $(PhO)_2PON_3/Et_3N$
(vi) $BH_3/Me_2S$
(vii) $(BOC)_2O/DMAP$
(viii) $NBS/CCl_4$
(ix) DMSO
(x) $HS(CH_2)_3SH/BF_3 OEt_2$.
Scheme 4:
(i) $BH_3/B(OMe)_3$
(ii) $Ac_2O/Et_3N$
(iii) Fe/AcOH
(iv) $(BOC)_2O$
(v) allyl bromide/NaH
(vi) $K_2CO_3$
(vii) $MnO_2$
(viii) $N_3CH_2CO_2Me/NaHMDS$
(ix) $MsCl/Et_3N$
(x) xylene
(xi) $Bu_3SnH/TEMPO$
(xii) Zn/AcOH
(xiii) $HNO_3/MeNO_2$
(xiv) HCl, then TMI acid/EDCI
(xv) Dichlorotriphenylphosphorane/pyridine
(xvi) $H_2/PtO_2/THF$
(xvii) $HCO_2H/Ac2O/THF$ then (32a) BH₃.DMS/reflux
(32c) NaBH₃CN/HCHO
(32d) 4-NO₂PhCH₂OCOCl

DETAILED DESCRIPTION OF THE INVENTION

Figure 1:
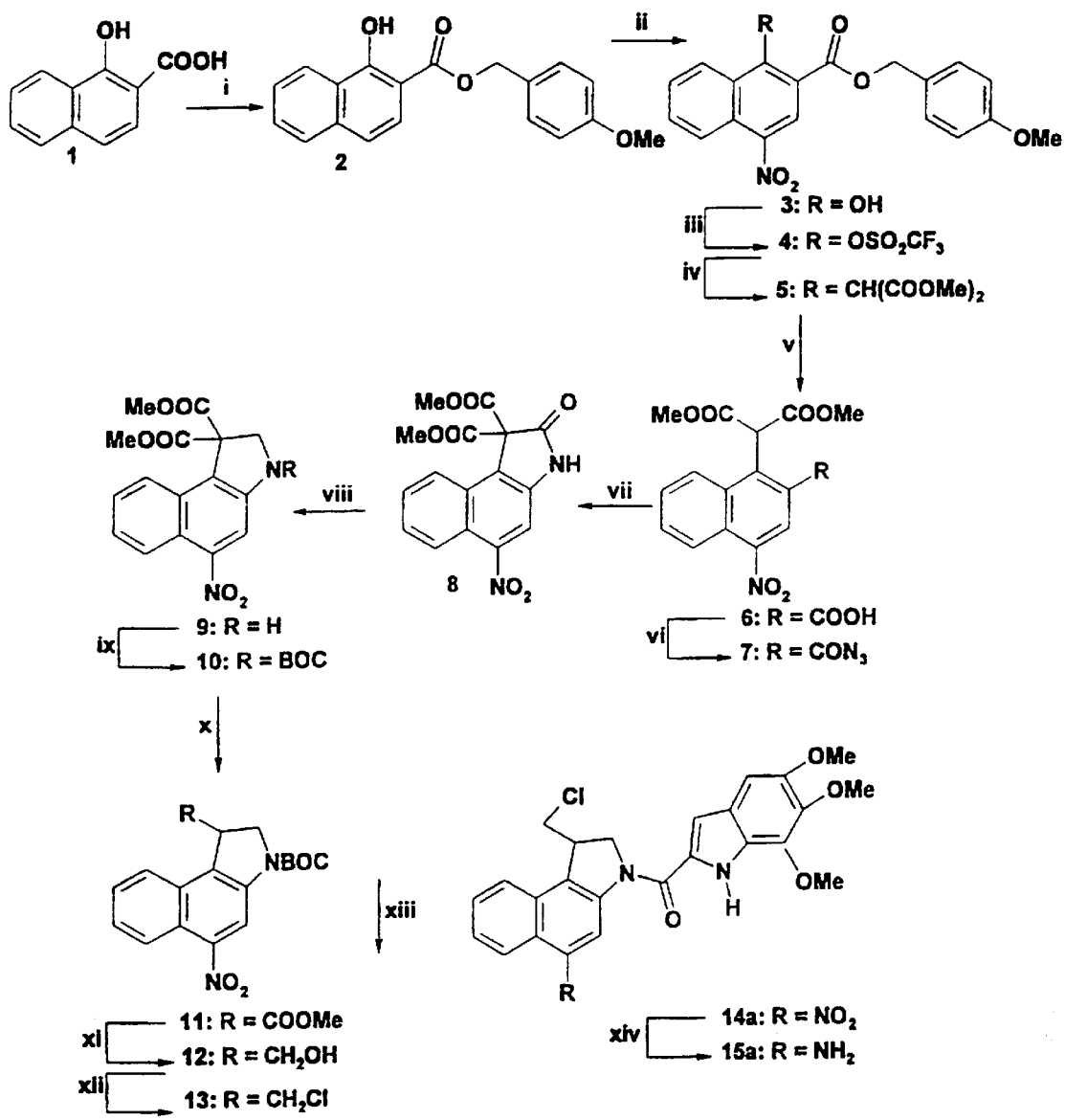
FIGS. 1 to 4 illustrate routes of synthesis for compounds of the invention referred to below as Schemes 1 to 4 respectively.
Figure 2:
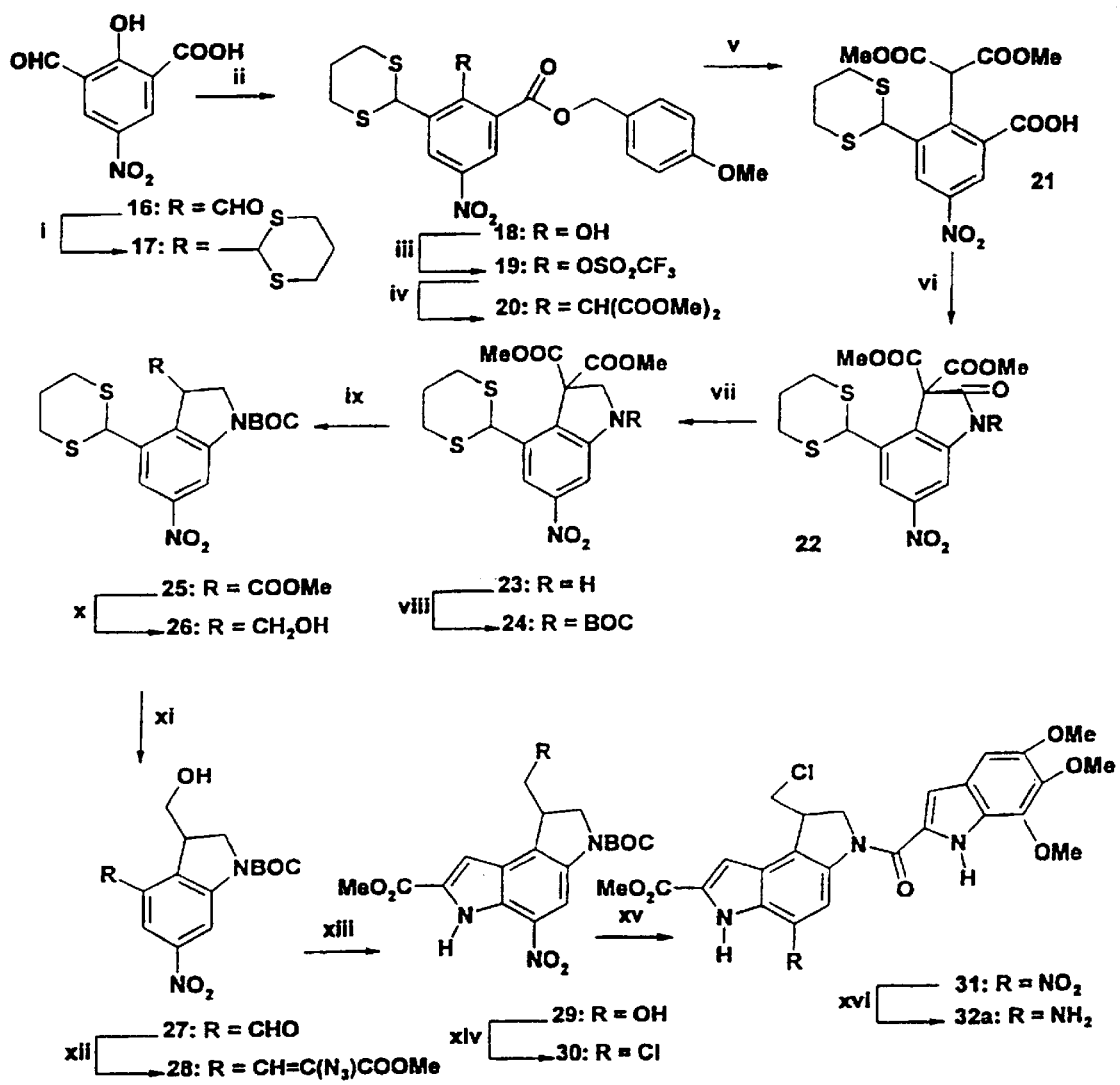
Figure 3:
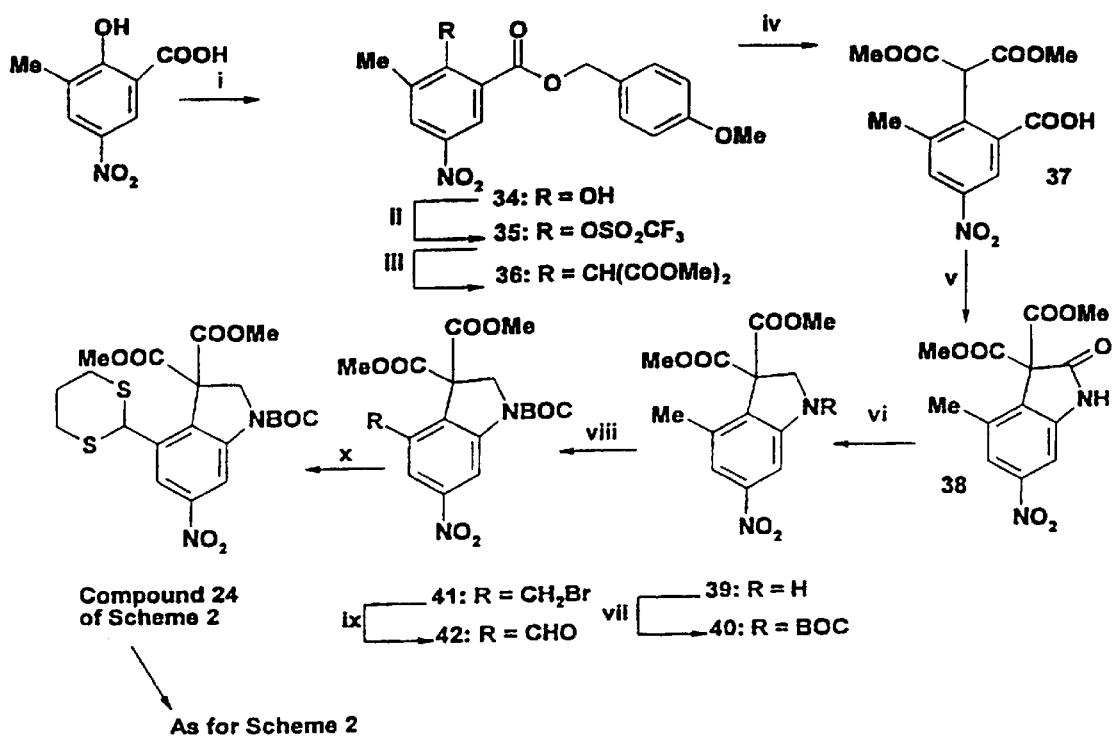
Figure 4:
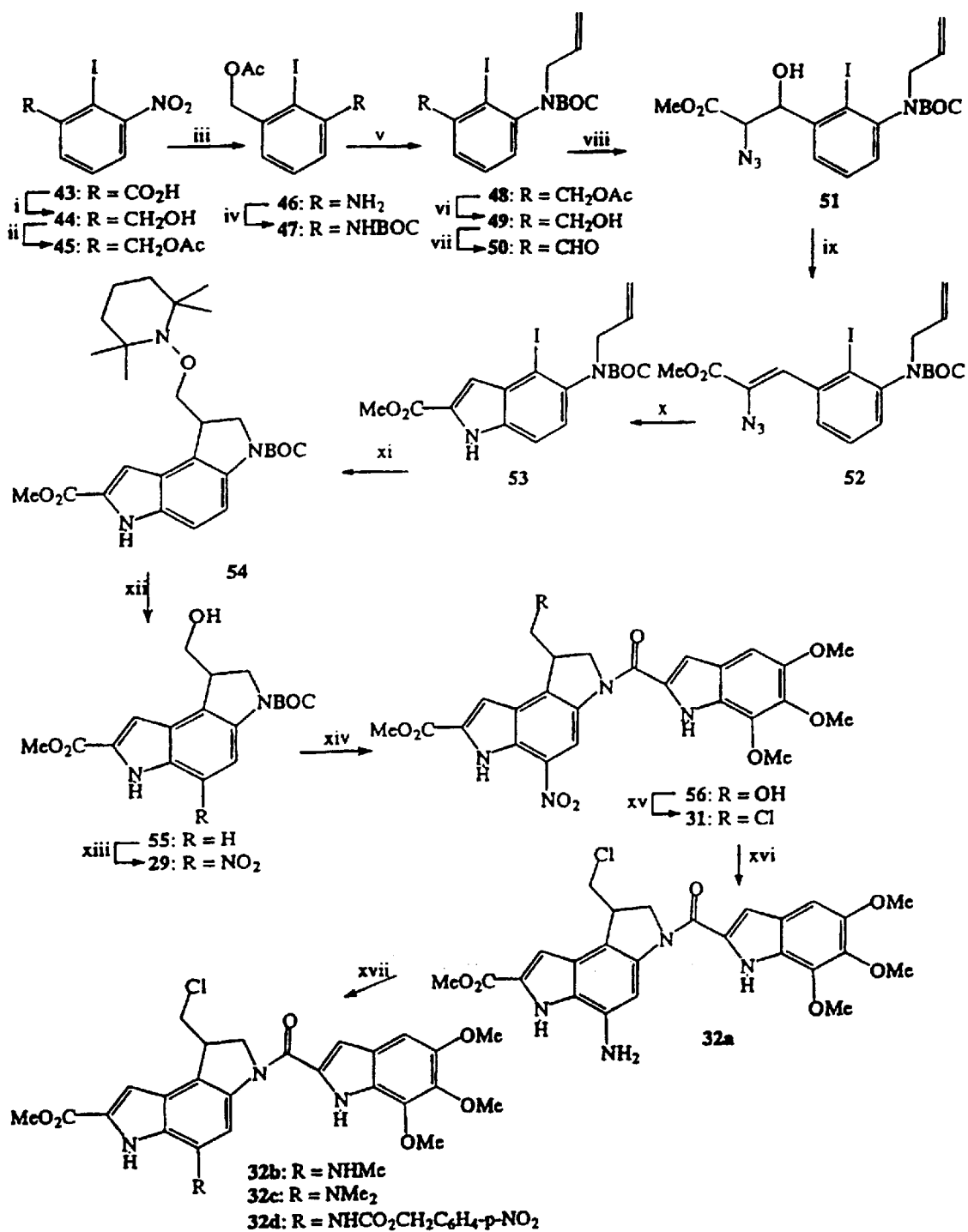

A. Synthesis of Compounds of the Formula (I)

The compounds of formula (I), where A and B represent a fused benzene ring, can be prepared by the process outlined in Scheme 1.

In Scheme 1, 1-hydroxynaphthalene-2-carboxylic acid (1) is protected as the 4-methoxybenzyl ester (2), and this is nitrated at the 4-position by 70% HNO₃ in AcOH to give (3). This is then transformed to the 1-trifluoromethanesulfonate derivative (4), which is treated directly with dimethyl malonate anion to give the 1-malonyl derivative (5). Deprotection of the 4-methoxybenzyl ester group with TFA gives the acid (6), which is converted to the unstable carbonyl azide (7) by treatment with the SOCl₂/DMF adduct in the presence of sodium azide and pyridine. Heating of this in toluene results in cyclisation to the indolone (8). This is reduced with borane/dimethyl sulfide in THF to give the indoline (9), which is N-protected with ditert-butyldicarbonate to give (10). This diester compound is decarboxymethylated with sodium methoxide, and the resulting monoester (11) is reduced with DIBAL to the alcohol (12). This alcohol is treated with an alkylsulfonyl halide (preferably methanesulfonyl chloride, as in the example of Scheme 1) in pyridine. If a compound of formula I in which X is halogen is desired, this reaction is followed by treatment of the resulting sulfonate ester with a lithium or potassium halide. In the example of Scheme 1, treatment with lithium chloride in DMF gives the chloride (13). The N-BOC group of 13 is removed by treatment with dioxane saturated with Hcl gas, and the resulting free amine is reacted immediately with acids in the presence of EDCI-HCl to give the corresponding amides (in the example of Scheme 1, with 5,6,7-trimethoxyindole-2-carboxylic acid to give (14a) of formula (I). Other acids corresponding to the group W are readily available. For example, for acids corresponding to formula (Ia), reference may be made to the synthetic routes disclosed in WO88/04659 and WO91/16324. For acids corresponding to formula (Ib), some synthetic methods are described in the literature (for example, Wang, Y., Grupta, R., Huang, L., Luo, W. and Lown, J. W., Anti-Canter Drug Design, 1996, 11, 15–34). In this example, reduction of (14a) by hydrogenation in the presence of platinum oxide then gave the desired amino compound (15a). Controlled hydrogenation of the nitro compounds (Y=NO₂ in formula I) in DMF provides the hydroxylamines (Y=NHOH in formula I). Diazonium chemistry may be used to convert the amino compounds (Y=NH₂ in formula I) to the azides (Y=N₃ in formula I), to sulfur derivatives (Y=SR or SSR in formula I), or to symmetrical azo compounds (Y=NNR in formula I). Unsymmetrical azo compounds (Y=NNPhR in formula I) can be prepared by reaction of the amines *Y=NH₂ in formula I) with nitroso compounds ONPhR. The amines (Y=NH₂ in formula I) can also be alkylated by standard methods (including reductive amination) to give substituted amines (Y=NHR or NRR in formula I). When Y is a tertiary amine, oxidation (for example with peracids) can be used to provide the corresponding N-oxides (Y=NRR(O) in formula I).

The compounds of formula (I), where A and B represent a fused pyrrole ring (with a 2-methoxycarbonyl substituent) can be prepared by the processes outlined in Schemes 2 to 4. In Scheme 2, 3-carboxy-2-hydroxy-5-nitrobenzaldehyde (16) [Bull. Soc. Chim. Fr., 1969, 817] is protected as the 1,3-dithiane derivative (17). Protection of the acid as the ester (18), preparation of the trifluoromethanesulfonate (19), displacement with dimethylmalonate anion to give (20) and deprotection of the ester to give acid (21) proceeds essentially as described in Scheme 1. Acid 21 is cyclised to the indolone (22) by diphenylphosphoryl azide in the presence of triethylamine, then reduced to the indoline (23) with borane/dimethyl sulfide and protected as the N-BOC derivative (24). Treatment of this with sodium methoxide causes decarboxymethylation, the monoester (25) is reduced to the alcohol (26) with DIBAL, and the 1,3-dithiane protecting group cleaved with a mercuric salt. The resulting aldehyde (27) is condensed with methyl azidoacetate in the presence of sodium methoxide, and the product (28) is cyclised in boiling xylene to give the pyrrole-fused alcohol (29). Conversion of this to the chloride (30) may be achieved using triphenylphosphine/carbon tetrachloride. Removal of the BOC protecting group, and coupling with an acid (in the Example of Scheme 2, with 5,6,7-trimethoxyindole-2-carboxylic acid) to give (31), and subsequent hydrogenation over platinum oxide to give aniline (32) follows the procedures described in Scheme 1.

Scheme 3 presents an alternative synthesis of compounds of formula (I), where A and B represent a fused pyrrole ring (with a 2-methoxycarbonyl substituent). In Scheme 3, 2-hydroxy-3-methyl-5-nitrobenzoic acid (33) [Ann., 1900, 311, 26] is protected as the 4-methoxybenzyl ester (34). Conversion to the trifluoromethanesulfonate (35), displacement with malonate to give (36) and deprotection of the ester to give acid (37) proceeds essentially as described in Scheme 1. The acid 37 is cyclised to the indolone (38), reduced to the indoline (39) and protected as the N-BOC derivative (40) as described in Scheme 2. Bromination with N-bromosuccinamide provides bromide (41), which may be oxidised to the aldehyde (42) and subsequently protected to provide an alternative route to the 1,3-dithiane (24) of Scheme 2.

Scheme 4 presents a further alternative synthesis of compounds of formula (I), where A and B represent a fused pyrrole ring (with a 2-methoxycarbonyl substituent). In Scheme 4, 2-iodo-3-nitrobenzoic acid (43) is reduced with borane-dimethylsulfide to the alcohol 44, converted to the acetate 45, then reduced (Fe powder/AcOH) to the amine 46 and protected as the NBOC derivative 47. This is sequentially N-alkylated with allyl bromide to give the N-allyl compound 48, which is hydrolysed to the alcohol 49 and this oxidised with MNO₂ to give the aldehyde 50. Treatment of 50 with sodium bis(trimethylsilyl)amide and methyl azidoacetate gives the azidoalcohol 51, which is converted to the azidocinnamate 52 by reaction with methanesulfonyl chloride and triethylamine. A solution of 52 in xylene is heated under reflux to give the indole 53. Reaction of 53 with tributyltin hydride and TEMPO (2,2,6,6-tetramethylpiperidinyloxy) gives 54, which is reduced with Zn powder to the pyrrolo[3,2-e]indole 55, and nitration of this with c.HNO₃ in CH₃NO₂ gives 29. The NBOC group of 29 is removed in HCl-saturated dioxane, and the resulting free amine is reacted immediately with acids in the presence of EDCI-HCl as described in Scheme 1, to give the corresponding amides (in the case illustrated in Scheme 4, with 5,6,7-trimethoxyindole-2-carboxylic acid to give 56). Treatment of 56 with dichlorotriphenylphosphorane gives the chloride 31, that can be hydrogenated (THF/PtO₂/H₂) to the amine 32a.

Although Schemes 1–4 are illustrated with particular substituents in each case, alternative substituted compounds may be used to provide other compounds of formula (I). In addition to Schemes 1–4 above, reference may also be made to the synthetic routes disclosed in WO88/04659 and WO91/16324, especially those in which Q is another group of the formula (Ia). Analogous routes may be used to make compounds of the present invention.

B. Synthesis of Compounds of the Formula (II)

The compounds of formula (II) where P is IIa or IIb may be prepared by reaction of compounds of the formula (I) where Y is $NH_2$, NHOH or NHR with a reactive derivative of IIa or IIb, for example an acid or chloroformate derivative, made from the corresponding carboxylic acids or alcohols respectively. These carboxylic acids and alcohols may be made by known chemistry, and some are commercially available.

Compounds of the formula (II) where P is IIc may be prepared by reaction of compounds of the formula (I) where Y is $NH_2$, NHOH or NHR with a reactive derivative of glutamic acid (for example an isocyanate or protected isocyanate). The carboxy groups of glutamic acid may be protected by esterification with groups R, where R is defined as above but is not H. t-Butyl ester groups are preferred, and reference may be made, for example, to WO88/07378 and WO91/03460 for appropriate reaction conditions.

C. GDEPT

C(i) Vector Systems

In general, the vector for use in GDEPT therapies may be any suitable DNA or RNA vector.

Suitable viral vectors include those which are based upon a retrovirus. Such vectors are widely available in the art. Huber et al. (ibid) report the use of amphotropic retroviruses for the transformation of hepatoma, breast, colon or skin cells. Culver et al. (Science (1992) 256; 1550–1552) also describe the use of retroviral vectors in GDEPT. Such vectors or vectors derived from them may also be used. Other retroviruses may also be used to make vectors suitable for use in the present invention. Such retroviruses include rous sarcoma virus (RSV).

Englehardt et al. (Nature Genetics (1993) 4; 27–34) describe the use of adenovirus based vectors in the delivery of the cystic fibrosis transmembrane conductance product (CFTR) into cells, and such adenovirus based vectors may also be used. Vectors utilising adenovirus promoter and other control sequences may be of use in delivering a system according to the invention to cells in the lung, and hence useful in treating lung tumours.

Other vector systems including vectors based on the Molony murine leukaemia virus are known (Ram, Z. et al., Cancer Research (1993) 53; 83–88; Dalton & Treisman, Cell (1992) 68; 597–612). These vectors contain the Murine Leukaemia virus (MLV) enhancer cloned upstream at a β-globin minimal promoter. The β-globin 5' untranslated region up to the initiation ATG is supplied to direct efficient translation of the enzyme.

Suitable promoters which may be used in vectors described above, include MLV, CMV, RSV and adenovirus promoters. Preferred adenovirus promoters are the adenovirus early gene promoters. Strong mammalian promoters may also be suitable. An example of such a promoter is the EF-1α promoter which may be obtained by reference to Mizushima and Nagata ((1990), Nucl. Acids Res. 18; 5322). Variants of such promoters retaining substantially similar transcriptional activities may also be used.

C(ii) Nitroreductase

Compounds of the formula (II) in which P is a group (IIa) or (IIb) and compounds of the formula (I) in which Y is a group $NO_2$ or N(O)RR can be activated by reduction of the group P or Y (as defined above) by nitroreductase.

Preferably, the enzyme is a non-mammalian nitroreductase enzyme, such as a bacterial nitroreductase. An E. coli nitroreductase as disclosed in WO93/08288 is particularly preferred. The enzyme may be modified by standard recombinant DNA techniques, e.g. by cloning the enzyme, determining its gene sequence and altering the gene sequence by methods such as truncation, substitution, deletion or insertion of sequences for example by site-directed mutagenesis. Reference may be made to "Molecular Cloning" by Sambrook et al. (1989, Cold Spring Harbor) for discussion of standard recombinant DNA techniques. The modification made may be any which still leaves the enzyme with the ability to reduce the nitro group of the protecting group P in formula II or the nitro or amine N-oxide groups when these are represented by Y in formula I but alters other properties of the enzyme, for example its rate of reaction or selectivity.

In addition, small truncations in the N- and/or C-terminal sequence may occur as a result of the manipulations required to produce a vector in which a nucleic acid sequence encoding the enzyme is linked to the various other vector sequences.

C(iii) Carboxypeptidase

Compounds of the formula (II) in which P is a group (IIc) can be activated by removal of the group P by a carboxypeptidase.

The enzyme is preferably a bacterial carboxypeptidase, especially carboxypeptidase CPG2 or Pseudomonas γ-glutamylhydrolase EC3.4.22.12 (Levy, C. C. & Goldman, P., J. Biol. Chem. 242; p 2933 (1967).

Carboxypeptidase G2 (CPG2) is disclosed in WO88/07378. Although native CPG2 is preferred, alterations to its sequence which are amino acid substitutions, deletions or insertions (e.g. of about 1, 2, 3, 4, 5, 10 or 20 residues in each case) are also possible. In any event, the alteration will be such that the enzyme retains its ability to convert a prodrug to an active drug at substantially the same rate as the native enzyme. In this context, "substantially the same rate" will desirably be within 1 order of magnitude, and preferably from about 50-fold e.g. about 2-fold less to 2, 5 or 10 fold more.

In addition to specific changes the enzyme may otherwise be altered by truncation, substitution, deletion or insertion as long as the activity of the enzyme is substantially unchanged as defined above. For example, small truncations in the N- and/or C-terminal sequence may occur as a result of the manipulations required to produce a vector in which a nucleic acid sequence encoding the enzyme is linked to a suitable promoter.

D. ADEPT

For applications in ADEPT systems, an antibody directed against a tumour specific marker is linked to the nitroreductase or carboxypeptidase enzyme, which may be modified as described above. The antibody may be monoclonal or polyclonal. For the purposes of the present invention, the term "antibody", unless specified to the contrary, includes fragments of whole antibodies which retain their binding activity for a tumour target antigen. Such fragments include Fv, F(ab') and F(ab')$_2$ fragments, as well as single chain antibodies. Furthermore, the antibodies and fragments thereof may be humanised antibodies, e.g. as described in EP-A-239400.

The antibodies may be produced by conventional hybridoma techniques or, in the case of modified antibodies or fragments, by recombinant DNA technology, e.g. by the expression in a suitable host vector of a DNA construct encoding the modified antibody or fragment operably linked to a promoter. Suitable host cells include bacterial (e.g. *E. coli*), yeast, insect and mammalian. When the antibody is produced by such recombinant techniques the enzyme may be produced by linking a nucleic acid sequence encoding the enzyme (optionally modified as described above) to the 3' or 5' end of the sequence of the construct encoding the antibody or fragment thereof.

E. Physiologically Functional Derivatives

Physiologically functional derivatives of prodrugs include salts, amides and esters. Esters include carboxylic acid esters in which the non-carbonyl moiety of the ester grouping is selected from straight or branched chain $C_{1-6}$alkyl, (methyl, n-propyl, n-butyl or t-butyl); or $C_{3-6}$cyclic alkyl (e.g. cyclohexyl). Salts include physiologically acceptable base salts, e.g. derived from an appropriate base, such as alkali metal (e.g. sodium), alkaline earth metal (e.g. magnesium) salts, ammonium and $NR_{4''}$ (wherein R'' is $C_{1-4}$ alkyl) salts. Other salts include acid addition salts, including the hydrochloride and acetate salts. Amides include non-substituted and mono- and di-substituted derivatives. Such derivatives may be prepared by techniques known per se in the art of pharmacy.

F. Applications of the Invention

The compounds of the invention can be used in a method of treatment of the human or animal body. Such treatment includes a method of treating the growth of neoplastic cells in a patient with neoplastic disease which comprises administering to a patient in need of treatment compounds of formula (I) of the invention, or compounds of formula (II) of the invention as part of an ADEPT or GDEPT therapy system. Neoplastic diseases include leukaemia and solid tumours such as breast, bowel and lung tumours including small cell lung carcinoma.

It will be understood that where treatment of tumours is concerned, treatment includes any measure taken by the physician to alleviate the effect of the tumour on a patient. Thus, although complete remission of the tumour is a desirable goal, effective treatment will also include any measures capable of achieving partial remission of the tumour as well as a slowing down in the rate of growth of a tumour including metastases. Such measures can be effective in prolonging and/or enhancing the quality of life and relieving the symptoms of the disease.

F(i) Compounds of the Formula (I)

Compounds of the formula (I) of the present invention may be used in a method of treatment of neoplastic disease in a patient, which method comprises administering to a patient in need of treatment an effective amount of a compound of formula (I). The compound may be administered in the form of a pharmaceutical composition.

While the exact dose of the compound will be at the discretion of the physician, taking account of the condition and needs of the patient, typical doses will be in the range of from about 0.1 to 200 mg/Kg, preferably about from 10 to 100 mg/Kg per patient per day.

F(ii) ADEPT Therapy

The antibody/enzyme conjugate for ADEPT can be administered simultaneously but it is often found preferable, in clinical practice, to administer the enzyme/agent conjugate before the prodrug, e.g. up to 72 hours or even 1 week before, in order to give the enzyme/agent conjugate an opportunity to localise in the region of the tumour target. By operating in this way, when the prodrug is administered, conversion of the prodrug to the cytotoxic agent tends to be confined to the regions where the enzyme/agent conjugate is localised, i.e. the region of the target tumour the premature release of the compound of formula (II) is minimised.

In ADEPT the degree of localisation of the enzyme/agent conjugate (in terms of the ratio of localized to freely circulating active conjugate) can be further enhanced using the clearance and/or inactivation systems described in WO89/10140. This involves, usually following administration of the conjugate and before administration of the prodrug, the administration of a component (a "second component") which is able to bind to the such part of the conjugate so as to inactivate the enzyme and/or accelerate the clearance of the conjugate from the blood. Such a component may include an antibody to the enzyme component of the system which is capable of inactivating the enzyme.

The second component may be linked to a macromolecule such as dextran, a liposome, albumin, macroglobulin or a blood group O erythrocyte so that the second component is restrained from leaving the vascular compartment. In addition or as an alternative, the second component may include a sufficient number of covalently bound galactose residues, or residues of other sugars such as lactose or mannose, so that it can bind the conjugate in plasma but be removed together with the conjugate from plasma by receptors for galactose or other sugars in the liver. The second component should be administered and designed for use such that it will not, to any appreciable extent, enter the extravascular space of the tumour where it could inactivate localised conjugate prior to and during administration of the prodrug.

In ADEPT systems, the dose of the prodrug and conjugate will ultimately be at the discretion of the physician, who will take into account such factors as the age, weight and condition of the patient. Suitable doses of prodrug and conjugate are given in Bagshawe et al. Antibody, Immunoconjugates, and Radiopharmaceuticals (1991), 4, 915–922. A suitable dose of conjugate may be from 500 to 200,000 enzyme units/m$^2$ (e.g. 20,000 enzyme units/m$^2$) and a suitable dose of prodrug may be from about 0.1 to 200 mg/Kg, preferably about from 10 to 100 mg/Kg per patient per day.

In order to secure maximum concentration of the conjugate at the site of desired treatment, it is normally desirable to space apart administration of the two components by at least 4 hours. The exact regime will be influenced by various factors including the nature of the tumour to be targeted and the nature of the prodrug, but usually there will be an adequate concentration of the conjugate at the site of desired treatment within 48 hours.

The ADEPT system when used with nitroreductase also preferably comprises a suitable cofactor for the enzyme. Suitable cofactors include a riboside or ribotide of nicotinic acid or nicotinamide.

The antibody/enzyme conjugate may be administered by any suitable route usually used in ADEPT therapy. This includes parental administration of the antibody in a manner and in formulations similar to that described in section G(iv) below.

F(iii) GDEPT Therapy

For use of the vectors in therapy, the vectors will usually be packaged into viral particles and the particles delivered to the site of the tumour, as described in for example Ram et al. (ibid). The viral particles may be modified to include an antibody, fragment thereof (including a single chain) or tumour-directed ligand to enhance targeting of the tumour.

Alternatively the vectors may be packaged into liposomes. The liposomes may be targeted to a particular tumour. This can be achieved by attaching a tumour-directed antibody to the liposome. Viral particles may also be incorporated into liposomes. The particles may be delivered to the tumour by any suitable means at the disposal of the physician. Preferably, the viral particles will be capable of selectively infecting the tumour cells. By "selectively infecting" it is meant that the viral particles will primarily infect tumour cells and that the proportion of non-tumour cells infected is such that the damage to non-tumour cells by administration of a prodrug will be acceptably low, given the nature of the disease being treated. Ultimately, this will be determined by the physician.

One suitable route of administration is by injection of the particles in a sterile solution. Viruses, for example isolated from packaging cell lines may also be administered by regional perfusion or direct intratumoral direction, or direct injection into a body cavity (intracaviterial administration), for example by intraperitoneum injection.

The exact dosage regime for both ADEPT will, of course, need to be determined by individual clinicians for individual patients and this, in turn, will be controlled by the exact nature of the prodrug and the cytotoxic agent to be released from the prodrug but some general guidance can be given. Chemotherapy of this type will normally involve parenteral administration of modified virus and administration by the intravenous route is frequently found to be the most practical.

In GDEPT systems the amount of virus or other vector delivered will be such as to provide a similar cellular concentration of enzyme as in the ADEPT system mentioned above. Typically, the vector will be administered to the patient and then the uptake of the vector by transfected or infected (in the case of viral vectors) cells monitored, for example by recovery and analysis of a biopsy sample of targeted tissue. This may be determined by clinical trials which involve administering a range of trial doses to a patient and measuring the degree of infection or transfection of a target cell or tumour. The amount of prodrug required will be similar to or greater than that for ADEPT systems.

In using a GDEPT system the prodrug will usually be administered following administration of the vector encoding an enzyme. Suitable doses of prodrug are from about 0.1 to 200 mg/Kg, preferably about from 10 to 100 mg/Kg per patient per day.

F(iv) Administration of Drug or Prodrug

While it is possible for the compounds of formula (I) or the prodrugs of formula (II) to be administered alone it is preferable to present them as pharmaceutical formulations. The formulations comprise the compounds, together with one or more acceptable carriers thereof and optionally other therapeutic ingredients. The carrier or carriers must be "acceptable" in the sense of being compatible with the other ingredients of the formulation and not deleterious to the recipients thereof, for example, liposomes. Suitable liposomes include, for example, those comprising the positively charged lipid (N[1-(2,3-dioleyloxy)propyl]-N,N,N-triethylammonium (DOTMA), those comprising dioleoyl-phosphatidylethanolamine (DOPE), and those comprising 3β[N-(n'N'-dimethylaminoethane)-carbamoyl]cholesterol (DC-Chol).

Formulations suitable for parental or intramuscular administration include aqueous and non-aqueous sterile injection solutions which may contain anti-oxidants, buffers, bacteriostats, bactericidal antibiotics and solutes which render the formulation isotonic with the blood of the intended recipient; and aqueous and non-aqueous sterile suspensions which may include suspending agents and thickening agents, and liposomes or other microparticulate systems which are designed to target the compound to blood components or one or more organs. The formulations may be presented in unit-dose or multi-dose containers, for example sealed ampoules and vials, and may be stored in a freeze-dried (lyophilized) condition requiring only the addition of the sterile liquid carrier, for example water, for injections, immediately prior to use. Injection solutions and suspensions may be prepared extemporaneously from sterile powders, granules and tablets of the kind previously described.

It should be understood that in addition to the ingredients particularly mentioned above the formulations may include other agents conventional in the art having regard to the type of formulation in question. Of the possible formulations, sterile pyrogen-free aqueous and non-aqueous solutions are preferred.

The doses may be administered sequentially, e.g. at daily, weekly or monthly intervals, or in response to a specific need of a patient. Preferred routes of administration are oral delivery and injection, typically parental or intramuscular injection or intratumoural injection.

The exact dosage regime will, of course, need to be determined by individual clinicians for individual patients and this, in turn, will be controlled by the exact nature of compound of formula (I) but some general guidance can be given. Typical dosage ranges generally will be those described above which may be administered in single or multiple doses. Other doses may be used according to the condition of the patient and other factors at the discretion of the physician.

The invention is illustrated by the following examples which start on the next page.

EXAMPLES

Figure 5:
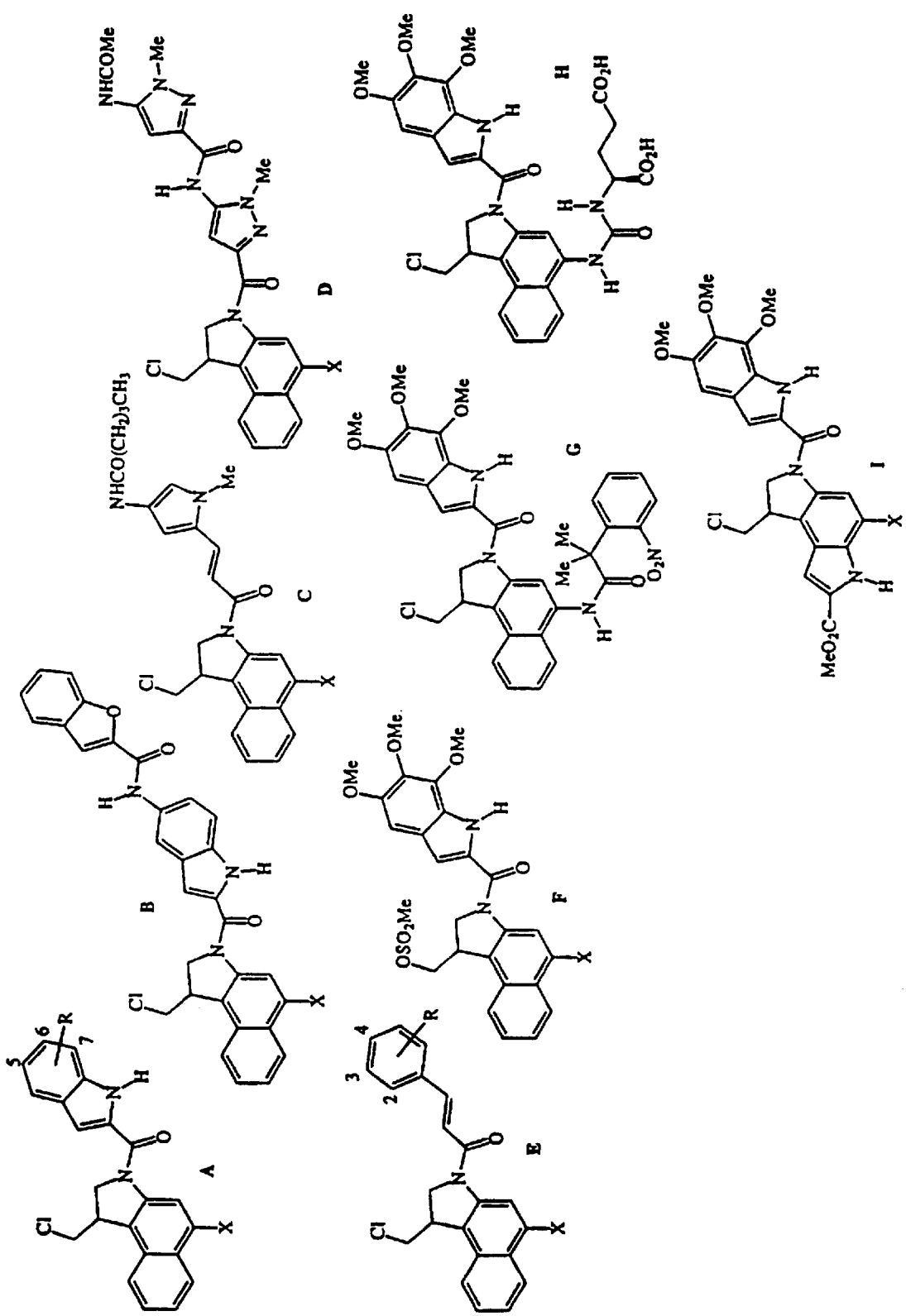
FIG. 5 shows the general structures of compounds of the invention further exemplified in the examples and characterised in Table 1 below.

The following examples A to NN illustrate the preparation of compounds representative of general formulae I and II by the methods outlined in Schemes 1 to 4. The compounds prepared are summarised in Table 1 below, which in column 2 refers to the structures set out in FIG. 5.

TABLE 1

| No. | form | X | R | Mp | Formula | Analyses |
|---|---|---|---|---|---|---|
| 14a | A | $NO_2$ | 5,6,7-triOMe | 243–245 | $C_{25}H_{22}ClN_3O_6$ | C, H, N |
| 14aR[a] | A | $NO_2$ | 5,6,7-triOMe | — | $C_{25}H_{22}ClN_3O_6$ | |
| 14aS[b] | A | $NO_2$ | 5,6,7-triOMe | — | $C_{25}H_{22}ClN_3O_6$ | |
| 15a | A | $NH_2$ | 5.6,7-triOMe | 199–204 | $C_{25}H_{24}ClN_3O_4$ | C, H, N, Cl1 |
| 15aR[a] | A | $NH_2$ | 5,6,7-triOMe | — | $C_{25}H_{24}ClN_3O_4$ | |
| 15aS[b] | A | $NH_2$ | 5,6,7-triOMe | — | $C_{25}H_{24}ClN_3O_4$ | |
| 14b | A | $NO_2$ | 5-$NO_2$ | >300 | $C_{22}H_{15}ClN_4O_5$ | C, H, N, Cl |

TABLE 1-continued

| No. | form | X | R | Mp | Formula | Analyses |
|---|---|---|---|---|---|---|
| 15b | A | $NH_2$ | 5-$NH_2$ | >300 | $C_{22}H_{19}ClN_4O$ | C, H, N, Cl |
| 14c | A | $NO_2$ | 5-NHCOMe | 252–253 | $C_{24}H_{19}ClN_4O_4$ | C, H, N, Cl |
| 15c | A | $NH_2$ | 5-NHCOMe | >300 | $C_{24}H_{21}ClN_4O_2$ | C, H, N, Cl |
| 14d | A | $NO_2$ | 5-OMe | 241–243 | $C_{23}H_{18}ClN_3O_4$ | C, H, N, Cl |
| 15d | A | $NH_2$ | 5-OMe | 250–255 | $C_{23}H_{20}ClN_3O_2$ | C, H, N, Cl |
| 14e | A | $NO_2$ | 5-O$(CH_2)$2$NMe_2$ | 224–227 | $C_{25}H_{25}ClN_4O_4$ | C, H, N, Cl |
| 15e | A | $NH_2$ | 5-O$(CH_2)$2$NMe_2$ | >250 | $C_{26}H_{27}ClN_4O_2$ | C, H, N, Cl |
| 14f | A | $NO_2$ | 5-OMe, 6-O$(CH_2)$2$NMe_2$ | 224–234 | $C_{27}H_{27}ClN_4O_5$ | C, H, N |
| 15f | A | $NH_2$ | 5-OMe, 6-O$(CH_2)$2$NMe_2$ | 130–133 | $C_{27}H_{29}ClN_4O_3 \cdot \frac{1}{2}H_2O$ | C, H, N, Cl |
| 14g | A | $NO_2$ | 5-OMe, 7-O$(CH_2)$2$NMe_2$ | 230–240 | $C_{21}H_{21}ClN_4O_5$ | C, H, N, Cl |
| 15g | A | $NH_2$ | 5-OMe, 7-O$(CH_2)$2$NMe_2$ | 109–111 | $C_{27}H_{29}ClN_4O_3 \cdot 1\frac{1}{2}H_2O$ | C, H, N, Cl |
| 14h | B | $NO_2$ | | 277 | $C_{31}H_{21}ClN_4O_5$ | C, H, N, Cl |
| 15h | B | $NH_2$ | | >300 | $C_{31}H_{23}ClN_4O_3 \cdot \frac{1}{2}H_2O$ | C, H, N |
| 14i | C | $NO_2$ | | 216 | $C_{25}H_{25}ClN_4O_4$ | C, H, N |
| 15i | C | $NH_2$ | | 245–250 | $C_{25}H_{27}ClN_4O_2$ | C, H, N |
| 14j | D | $NO_2$ | | 158–160 | $C_{25}H_{23}ClN_8O_5$ | C, H, N |
| 15j | D | $NH_2$ | | >250 | $C_{25}H_{25}ClN_8O_3$ | C, H, N, Cl |
| 14k | E | $NO_2$ | 3-NHCOMe | 214–216 | $C_{24}H_{20}ClN_3O_4$ | C. H, N, Cl |
| 15k | E | $NH_2$ | 3-NHCOMe | >250 | $C_{24}H_{22}ClN_3O_2$ | C, H, N, Cl |
| 14l | E | $NO_2$ | 3-OMe | 200 | $C_{23}H_{19}ClN2O_4$ | C, H, N, Cl |
| 15l | E | $NH_2$ | 3-OMe | >200 | $C_{23}H_{21}ClN2O_2$ | C, H, N, Cl |
| 15m | E | $NH_2$ | 4-NHCOMe | >250 | $C_{24}H_{22}ClN_3O_2$ | C, H, N, Cl |
| 15n | E | $NH_2$ | 4-OMe | 114–116 | $C_{23}H_{21}ClN2O_2$ | C, H, N, Cl |
| 14o | F | $NO_2$ | | 213.5–214.5 | $C_{26}H_{25}N_3O_9S$ | C, H, N |
| 15o | F | $NH_2$ | | >260 | $C_{26}H_{27}N_3O_7S$ | C, H, N |
| 15p | A | NHMe | 5,6,7-triOMe | 122–125 | $C_{26}H_{26}ClN_3O_4$ | C, H, N, Cl |
| 15q | A | $NMe_2$ | 5,6,7-triOMe | 174–175 | $C_{27}H_{28}ClN_3O_4$ | C, H, N |
| 15r | A | $T^c$ | | 191–192 | $C_{33}H_{29}ClN_4O_8$ | C, H, N, Cl |
| 15s | G | — | | 139–143 | $C_{36}H_{33}ClN_4O_7$ | mass spec |
| 15t | H | | | foam | $C_{31}H_{31}ClN_4O_9$ | mass spec |
| 31 | I | $NO_2$ | | 246–247.5 | $C_{25}H_{23}ClN_4O_8$ | C, H, N |
| 32a | I | $NH_2$ | | 190–196 | $C_{25}H_{25}ClN_4O_6 \cdot \frac{1}{2}EtOAc$ | C, H, N |
| 32b | I | NHMe | | 201–205 | $C_{26}H_{27}ClN_4O_6 \cdot H_2O$ | C, H, N, Cl |
| 32c | I | $NMe_2$ | | 200–202 | $C_{27}H_{29}ClN_4O_6$ | C, H, N |
| 32d | I | $T^c$ | | 257–258.5 | $C_{33}H_{30}ClN_5O_{10}$ | C, H, N |

Footnotes to Table 1:
[a]R enantioners.
[b]S enantiomers.
[c]T = —NH—C(O)—$CH_2$—Ph-p$NO_2$ Example A Preparation of 1-chloromethyl-5-nitro-3-[5,6,7-trimethoxyindol-2-yl)-carbonyl]-1,2-dihydro-3H-benz[e]indole (This is a compound 15a of Scheme 1). A suspension of powdered sodium salt of 1-hydroxynaphthalene-2-carboxylic acid (1) (61.3 g, 0.29 mmol) in DMSO (205 mL) was treated with 4-methoxybenzyl chloride (98%, 46.7 g, 0.29 mmol) and then stirred at 70° C. for 1 h. After cooling, the mixture was poured into dilute aqueous $KHCO_3$ (3.5 L) and the resulting precipitate was collected, washed with water and dried. The solid was extracted with boiling petroleum ether (bp 60–65° C., 1100 mL), treated with decolourising charcoal and the filtered solution was cooled for a prolonged period at 0° C. to provide crude 4-methoxybenzyl 1-hydroxynaphthalene-2-carboxylate (2) (59.4 g, 66%), suitable for further use. A sample was recrystallised from $iPr_2O$/petroleum ether, mp 92–93° C. $^1$H NMR [$(CD_3)_2SO$] δ 11.91 (s, 1H, OH), 8.31 (d, J=8.2 Hz, 1H, H-3), 7.92 (d, J=8.1 Hz, 1H, H-4), 7.73 (d, J=8.8 Hz, 1H, ArH), 7.71 (brt, J=7.5 Hz, 1H, ArH), 7.61 (br t, J=1.6 Hz, 1H, ArH), 6.99 (d, J=8.6 Hz, 2H, H-3',5'), 5.40 (s, 2H, $CH_2$), 3.34 (s, 3H, $CH_3$). Anal. Calculated for $C_{19}H_{16}O_4$): C, 74.0; H, 5.2. Found: C, 73.7; H, 5.2%.

A warm vigorously stirred solution of 2 (25.4 g, 0.082 mmol) in AcOH (260 mL) was cooled to 25° C. and treated in one portion with a solution of $HNO_3$ (70% w/w, 18.6 g, 0.20 mmol) in AcOH (25 mL). The temperature rose to 35° C. (controlled with external cooling) and a solid separated. After stirring for a further 10 min at 30° C., the mixture was cooled to 0° C. The precipitate was collected, washed with cold AcOH and $iPr_2O$, and recrystallised from $CH_2Cl_2$/petroleum ether to give 4-methoxybenzyl 1-hydroxy-4-nitronaphthalene-2-carboxylate (3) (17.9 g, 61%) mp 163–164° C. $^1$H NMR [$(CD_3)_2SO$] δ 12.46 (br s, 1H, OH), 8.60 (s, 1H, H-3), 8.60 (d, J=8.6 Hz, 1H, H-5), 8.47 (d, J=8.3 Hz, 1H, H-8), 7.97 (br t, J=7.8 Hz, 1H, H-6), 7.79 (br t, J=7.7 Hz, 1H, H-7), 7.50 (d, J=8.6 Hz, 2H, H-2',6'), 7.00 (d, J=8.7 Hz, 2H, H-3',5'), 5.32 (s, 2H, $CH_2$), 3.78 (s, 3H, $OCH_3$). Anal. Calculated for $C_{19}H_{15}NO_6$: C, 64.6; H, 4.3; N, 4.0. Found: C, 64.7; H, 4.0; N, 4.2%.

A suspension of 3 (12.90 g, 36.5 mmol) in $CH_2Cl_2$ (180 mL) was treated with $Et_3N$ (6.58 mL, 47.5 mmol) and the resulting solution was cooled to 0° C. and treated with triflic anhydride (7.82 mL, 43.8 mmol). The mixture was stirred at 0° C. for 30 min. and then treated with additional $NEt_3$ (1.00 mL, 7.2 mmol) followed by triflic anhydride (1.19 mL, 6.7 mmol). After stirring for a further 2 h at 20° C., the mixture was washed twice with water, then dried and concentrated under reduced pressure. The residue was extracted with boiling petroleum ether (bp 90–95° C., 500 mL) in the presence of decolourising charcoal, and the filtered solution was then cooled to 55° C. and refiltered through a celite pad to remove insoluble impurities. Following prolonged cooling, the separated solid was collected and washed with petroleum ether to give crude 4-methoxybenzyl 4-nitro-1-trifluoromethylsulfonyloxynaphthalene-2-carboxylate (4)

(13.09 g, 74%), suitable for further use. A sample recrystallised from petroleum ether had mp 74–75° C. $^1$H NMR (CDCl$_3$) δ 8.71 (s, 1H, H-3), 8.57 (d, J=8.1 Hz, 1H, H-5), 8.30 (d, J=8.4 Hz, 1H, H-8), 7.92 (br t, J=7.9 Hz, 1H, H-6), 7.84 (br t, J=7.8 Hz, 1H, H-7), 7.44 (d, J=8.7 Hz, 2H, H-2',6'), 6.93 (d, J=8.8 Hz, 2H, H-3',5'), 5.43 (s, 2H, CH$_2$), 3.82 (s, 3H, OCH$_3$). Anal. Calculated for C$_{20}$H$_{14}$F$_3$NO$_8$S: C, 49.5; H, 2.9; N, 2.91; S, 6.6. Found: C, 49.7; H, 2.8; N, 2.9; S, 6.6%.

A stirred solution of 4 (13.20 g, 27.2 mmol) and dimethyl malonate (5.39 g, 40.8 mmol) in DMF (85 mL) was cooled to –5° C. and treated with powdered K$_2$CO$_3$ (22.53 g, 163 mmol). The mixture was allowed to warm to 20° C. over a 2 h period, and after stirring for a further 12 h at 20° C. was poured slowly into cold stirred 0.5N HCl (1750 mL). The resulting solid was dissolved in CH$_2$Cl$_2$ and the solution was washed twice with water, dried (Na$_2$SO$_4$) and then evaporated to dryness. The residue was crystallised from CH$_2$Cl$_2$/iPr$_2$O/petroleum ether to give 4-methoxybenzyl 1-[di(methoxycarbonyl)methyl]-4-nitronaphthalene-2-carboxylate (5) (10.66 g, 84%), suitable for further use. A sample recrystallised from MeOH had mp 124–125° C. $^1$H NMR (CDCl$_3$) δ 8.62 (s, 1H, H-3), 8.45 (d, J=8.6 Hz, 1H, H-5), 8.21 (d, J=8.7 Hz, 1H, H-8), 7.70 (br t, J=7.7 Hz, 1H, H-6), 7.69 (br t, J=7.8 Hz, 1H, H-7), 7.41 (d, J=8.7 Hz, 2H, H-2',6'), 6.94 (d, J=8.7 Hz, 2H, H-3',5'), 6.62 (s, 1H, ArCH), 5.37 (s, 2H, CH$_2$), 3.83 (s, 3H, PhOCH$_3$), 3.69 (s, 6H, 2×CO$_2$CH$_3$). Anal. Calculated for C$_{24}$H$_{21}$NO$_9$: C, 61.6; H, 4.7; N, 3.1%.

Trifluoroacetic acid (36 mL) was added in one portion to a mixture of 5 (9.20 g, 19.7 mmol) and anisole (12.16 g, 20 mmol), and the resulting solution was stirred at 20° C. for 10 min and then diluted with cold water (800 mL). The precipitated semi-solid was collected, dissolved in EtOAc and the solution was washed with water, dried (Na$_2$SO$_4$) and then concentrated under reduced pressure below 30° C. The residue was triturated with iPr$_2$O to provide a crude product, which was recrystallised from EtOAc/iPr$_2$O/petroleum ether/AcOH (1drop) to give 1-[di(methoxycarbonyl)-methyl]-4-nitronaphthalene-2-carboxylic acid (6) (6.37 g, 93%), mp 153–154° C. (dec.). $^1$H NMR [(CD$_3$)$_2$SO] δ 14.1 (br s, 1H, CO$_2$H), 8.62 (s, 1H, H-3), 8.36 (d, J=8.2 Hz, 1H, H-5), 8.30 (d, J=8.7 Hz, 1H, H-8), 7.92 (br t, J=7.6 Hz, 1H, H-6), 7.84 (br t, J=7.7 Hz, 1H, H-7), 6.65 (s, 1H, ArCH), 3.63 (s, 6H, 2×CO$_2$CH$_3$). Anal. Calculated for C$_{16}$H$_{13}$NO$_8$: C, 55.3; H, 3.8; N, 4.0. Found: C, 55.4; H, 3.8; N, 3.7%.

A stirred suspension of 6 (7.00 g, 20.16 mmol) and powdered NaN$_3$ (3.28 g, 50.44 mmol) in CH$_2$Cl$_2$ (100 mL) was treated with pyridine (3.99 g, 50.44 mmol), then cooled to –5° C. and treated in one portion with N,N-dimethyl(chlorosulfonyl)methaniminium chloride [SOCl$_2$/DMF adduct] (4.26 g, 22.18 mmol). After stirring at 20° C. for 2 h, the mixture was washed twice with water, dried (Na$_2$SO$_4$) and filtered through a short column of silica gel, eluting with further CH$_2$Cl$_2$ (400 mL). Removal of the solvent under reduced pressure below 30° C. gave the crude carbonyl azide (7), which was immediately heated with stirring in dry toluene (65 mL) under reflux for 8 min. The mixture was cooled to 0° C. to complete precipitation of the product, which was collected and washed with toluene. This was stirred as a suspension in CH$_2$Cl$_2$ (25 mL) for 10 min at 20° C., diluted with iPr$_2$O, and the resulting solid collected to give 1,1-di(methoxycarbonyl)-5-nitro-1,2-dihydro-3H-benz[e]indole-2one (8) (5.60 g, 81%). A sample crystallised from CH$_2$Cl$_2$ had mp 218–222° C. (dec.). $^1$H NMR [CD$_3$)$_2$SO] δ 11.59 (s, 1H, NH), 8.21 (d, J=8.7 Hz, 1H, H-7), 7.95 (s, 1H, H-9), 7.87 (d, J=8.5 Hz, 1H, H-4), 7.74 (t, J=7.6 Hz, 1H, H-6), 7.65 (t, J=7.7 Hz, 1H, H-5), 3.72 (s, 6H, 2×CO$_2$CH$_3$). Anal. Calculated for C$_{16}$H$_{12}$N$_2$O$_7$.1.5 H$_2$O: C, 51.8; H, 4.1; N, 7.5. Found: C, 52.1; H, 3.1; N, 7.8%.

A solution of BH$_3$.DMS in THF (9.2 mL of 10 M, 92 mmol) was added to a solution of indolone 8 (17.60 g, 51 mmol) in THF (150 mL) and the mixture was stirred under reflux for 15 h. After cooling, MeOH (15 mL) was slowly added, followed by water (30 mL), and the mixture was then concentrated under reduced pressure below 30° C. to remove MeOH. The residue was shaken with water and the resulting semi-solid was collected and dissolved in CH$_2$Cl$_2$. The solution was washed with water (2×), dried (Na$_2$SO$_4$) and then concentrated under reduced pressure to provide a solid which was chromatographed on silica gel. Elution with CH$_2$Cl$_2$/EtOAc) 10:1) provided a crude product which was recrystallized from iPr$_2$O, and following prolonged cooling was collected to give 1,1-de(methoxycarbonyl)-5-nitro-1,2-dihydro-3H-benz[e]indole (9) (9.62 g, 57%) (contaminated with ca. 5% of 1-methoxycarbonyl-5-nitro-1,2-dihydro-3H-benz[e]indole). A sample recrystallised from iPr$_2$O had mp 141° C. $^1$H NMR (CDCl$_3$) δ 8.25 (d, J=8.7 Hz, 1H, H-7), 7.82 (d, J=8.6 Hz, 1H, H-4), 7.59 (s, 1H, H-9), 7.51 (br t, J=7.7 Hz, 1H, H-6), 7.42 (br t, J=7.8 Hz, 1H, H-5), 4.36 (d, J=2.3 Hz, 2H, NCH$_2$), 4.23 (brs, 1H, NH), 3.79 (s, 6H, 2×CO$_2$CH$_3$). Anal. Calculated for C$_{16}$H$_{14}$N$_2$O$_6$: C, 58.2; H, 4.3; N, 8.5. Found: C, 58.2; H, 4.0; N, 8.6%.

A mixture of crude 9 (9.35 g, 28.3 mmol), ditertbutyldicarbonate (8.28 g, 36.8 mmol) and 1-methylimidazole (3.02 g, 36.8 mmol) in THF (100 mL) was stirred at 45° C. for 1 h, and then concentrated under reduced pressure. The residue was partitioned between CH$_2$Cl$_2$ and 0.1 N AcOH, and the organic layer was washed twice with water, dried (Na$_2$SO$_4$) and concentrated under reduced pressure. The residue was stirred with CH$_2$Cl$_2$ (40 mL), then cooled and filtered to remove some of the 3-(tert-butyloxycarbonyl)-1-methoxycarbonyl-5-nitro-3H-benz[e]indole impurity. The CH$_2$Cl$_2$ solution was evaporated and the residue was chromatographed on silica gel. Elution with CH$_2$Cl$_2$/petroleum ether (1:1) provided a quantity of the indole impurity and further elution with CH$_2$Cl$_2$ gave a solid which was triturated with iPr$_2$O/petroleum ether to give 3-(tert-butyloxycarbonyl)-1,1-di(methoxycarbonyl)-5-nitro-1,2-dihydro-3H-benz[e]indole (10) (9.98 g, 82%). A sample recrysallised from iPr$_2$O had mp 151° C. $^1$H NMR (CDCl$_3$) δ8.85 (br s, 1 H, H-7), 7.93 (d, J=7.8 Hz, 1 H, H-4), 7.61–7.51 (m, 2 H, H-5,6), 4.69 (s, 2 H, NCH$_2$), 3.80 (s, 6 H, 2×CO$_2$CH$_3$), 1.61 (s, 9 H, C(CH$_3$)$_3$).

Anal. Calculated for C$_{21}$H$_{22}$N$_2$O$_8$: C, 58.6; H, 5.2; N, 6.5. Found: C, 58.7; H, 5.4; N, 6.4%.

NaOMe (5.61 mL of a 0.62 M solution in MeOH, 3.48 mmol) was added dropwise to a stirred solution of 10 (1.00 g, 2.32 mmol) in THF (20 mL) at 10° C. After 15 min at 20° C., trifluoroacetic acid (0.29 mL, 3.8 mmol) was added in one portion, causing dissipation of the deep purple colour of the solution. The reaction was diluted with saturated NaCl, extracted with CH$_2$Cl$_2$ and the extract was washed twice with water and dried (Na$_2$SO$_4$). The CH$_2$Cl$_2$ solution was filtered through a short column of silica gel, eluting with additional CH$_2$Cl$_2$, and the solvent was evaporated under reduced pressure below 30° C. to give crude 3-(tert-butyloxycarbonyl)-1-methoxycarbonyl-5-nitro-1,2-dihydro-3H-benz[e]indole (11) (0.85 g, 98%), which was used without further purification. $^1$H NMR (CDCl$_3$) δ8.89 (br s, 1 H, H-9), 8.38 (br s, 1 H, H-7), 7.87 (d, J=8.3 Hz, 1 H, H-4), 7.63–7.51 (m, 2 H, H-5,6), 4.61 (dd, J=10.5, 3.9 Hz, 1 H, NCH$_2$CH), 4.50 (br s, 1 H, NCH$_2$CH), 4.32 (t, J=11.1 Hz, 1 H, HCH$_2$CH), 3.72 (s, 3 H, CO$_2$CH$_3$), 1.61 (s, 9 H, C(CH$_3$)$_3$).

The crude ester 11 (0.85 g, 2.28 mmol) from the preceding procedure was dissolved in THF (25 mL) and added dropwise over 20 min to a stirred solution of DIBAL (9.1 mL of a 1M solution in toluene, 9.1 mmol) in THF (30 mL) under $N_2$ at 0° C. The mixture was stirred for a further 30 min at 0° C., then poured into ice-cold 2 N HCl (40 mL) and extracted twice with EtOAc. The combined extracts were dried ($Na_2SO_4$) and concentrated under reduced pressure below 30° C. and the residue was chromatographed on silica gel. Elution with $CH_2Cl_2$EtOAc (4:1) afforded a crude product which was crystallised from $CH_2Cl_2/iPr_2O$/petroleum ether to give 3-(tert-butyloxycarbonyl)-1-hydroxymethyl-5-nitro,1,2-dihydro-3H-benz[e]indole (12) (0.48 g, 61%). A sample recrystallised from $iPr_2O$/petroleum ether had mp 176° C. $^1H$ NMR ($CDCl_3$) δ(br s, 1 H, H-9), 8.42 (br s, 1 H, H-7), 7.88 (d, J=7.9 Hz, 1 H, H-4), 7.62–7.51 (m, 2 H, H5,6), 4.30 (m, 1 H, H-2), 4.17 (dd, J=11.4, 9.5 Hz, 1 H, H-2), 4.04–3.93 (m, 2 H, H-3, CHHOH), 383–3.74 (m, 1 H, CHHOH), 1.61 (s, 9 H, $C(CH_3)_3$).

Anal. Calculated for $C_{18}H_{20}N_2O_5$: C, 62.8; H, 5.9; N, 8.1. Found: C, 62.9; H, 6.1; N, 8.0%.

A stirred solution of 12 (0.42 g, 1.22 mmol) in pyridine (1.8 mL) was treated dropwise at 0° C. with mesyl chloride (1.13 mL, 1.46 mmol) and then stirred at 20° C. for a further 2 h. The mixture was diluted with water and the resulting solid was collected, dissolved in $CH_2Cl_2$, and the solution was washed twice with water, dried ($Na_2SO_4$) and evaporated under reduced pressure below 30° C. A mixture of the resulting crude mesylate and LiCl (0.21 g, 5 mmol) in DMF (4 mL) was stirred at 80° C. for 30 min, then cooled and diluted with water. The precipitated solid was dissolved in $CH_2Cl_2$ and filtered through a column of silica gel to give a crude product which was triturated with $iPr_2O$/petroleum ether, yielding 3-(tert-butyloxycarbonyl)-1-chloromethyl-5-nitro-1,2-dihydro-3H-benz[e]indole (13) (0.34 g, 77%). A sample recrystallised from $iPr_2o$/petroleum ether had mp 168–169° C. $^1H$ NMR ($CDCl_3$) δ8.88 (br s, 1 H, H-9), 8.42 (br s, 1 H, H-7), 7.80 (d, J=8.1 Hz, 1 H, H-4), 7.67–7.51 (m, 2 H, H-5,6), 4.34 (br s, 1 H, H-2), 4.20 (t, J=10.2 Hz, 1 H, H-2), 4.17–4.08 (m, 1 H, H-3), 3.92 (dd, J=11.2, 2.5 Hz, 1 H, CHHCl), 3.54 (t, J=10.3 Hz, CHHCl), 1.62 (s, 9 H, $C(CH_3)_3$).

Anal. Calculated for $C_{18}H_{19}ClN_2O_4$: C, 59.6; H, 5.3; N, 7.7; Cl, 9.8. Found: C, 59.98; H, 5.2; N, 7.7; Cl, 9.7%.

A solution of 13 (170 mg, 0.47 mmol) in HCl-saturated dioxane (10 mL) was stirred at 20° C. for 2 h, then evaporated under reduced pressure below 30° C. EDCI-HCl (270 mg, 1.41 mmol), 5,6,7-trimethoxyindole-2-carboxylic acid (118 mg, 0.47 mmol) and DMF (2.5 mL) were then added, and the mixture was stirred at 20° C. for 2 h. Addition of water precipitated a crude product, which was recrystallised twice from $CH_2Cl_2/iPr_2O$ to give 1-chloromethyl-5-nitro-3-[5,6,7-trimethoxyindol-2-yl)carbonyl]-1,2-dihydro-3H-benz[e]indole (14a) (156 mg, 67%), mp 243–245° C. $^1H$ NMR ($CDCl_3$) δ9.44 (s, 1 H, NH), 9.24 (s, 1 H, H-9), 8.43 (dd, J=7.9, 1.2 Hz, 1 H, H-7), 7.87 (dd, J=7.7, 1.5 Hz, 1 H, H-4), 7.70–7.60 (m, 2 H, H-5,6), 7.03 (d, J=2.5 Hz, 1 H, H-3'), 6.87 (s, 1 H, H-4'), 4.88 (dd, J=10.8, 2.1 Hz, 1 H, H-2), 4.74 (dd, J=10.4, 8.9 Hz, 1 H, H-2), 4.36–4.26 (m, 1 H, H-3), 4.10 (s, 3 H, $OCH_3$), 3.99 (dd, J=11.4, 3.1 Hz, 1 H, CHHCl), 3.95 (s, 3 H, $OCH_3$), 3.92 (s, 3 H, $OCH_3$), 3.58 (dd, J=11.4, 9.9 Hz, 1 H, CHHCl).

Anal. Calculated for $C_{25}H_{22}ClN_3O_6$: C, 60.5; H, 4.5; N, 8.5. Found: C, 60.1; H, 4.5; N, 8.4%.

EXAMPLE B

Preparation of 5-amino-1-(chloromethyl)-3-[(5,6,7-trimethoxyindol-2-yl)carbonyl]-1,2-dihydro-3H-benz[e]indole (15a) (Scheme 1).

A solution of 14a (60 mg, 0.12 mmol) in THF (15 mL) was hydrogenated over $PtO_2$ (15 mg) at 50 psi for 2 h. The catalyst was removed by filtration, the solution was concentrated to a small volume under reduced pressure below 30° C., and $iPr_2O$ was then added. The resulting solid was purified by precipitation from a THF solution with $iPr_2O$ at 20° C. to give 15a (53 mg, 94%), mp 199–204° C. $^1H$ NMR [($CD_3)_2SO$] δ 11.41 (d, J=1.2 Hz, 1 H, NH), 8.07 (d, J=8.5 Hz, 1 H, H-6), 7.75 (d, J=8.3 Hz, 1 H, H-9), 7.63 (br s, 1 H, H-4), 7.45 (t, J=7.6 Hz, 1 H, H-8), 7.28 (t, J=7.7 Hz, 1 H, H-7), 7.03 (d, J=2.0 Hz, 1 H, H-3'), 6.96 (s, 1 H, H-4'), 5.98 (s, 2 H, $NH_2$), 4.67 (dd, J=10.8, 8.9 Hz, 1 H, H-2), 4.41 (dd, J=10.9, 1.4 Hz, 1 H, H-2), 4.12–4.02 (m, 1 H, H-1), 3.96 (dd, J=11.0, 3.1 Hz, 1 H, CHHCl), 3.94 (s, 3 H, 7(—$OCH_3$), 3.82 (s, 3 H, 5(—$OCH_3$), 3.80 (s, 3 H, 6(—$OCH_3$), 3.71 (dd, J=10.9, 8.2 Hz, 1 H, CHHCl). $^{13}C$ NMR δ 160.1 (CO), 146.1 (C-5), 142.5 (C-3a), 139.7 (C-6'), 139.0 (C-7'), 131.3 (C-2'), 130.0 (C-9a), 126.7 (C-8), 125.2 (C-7a), 123.3 (C-6), 123.1 (C-3'a), 122.9 (C-9), 122.0 (C-7), 120.3 (C-5a), 111.9 (C-9b), 105.8 (C-3'), 98.5 (C-4), 97.9 (C-4'), 61.0 (7'—$OCH_3$), 60.9 (6'—$OCH_3$), 55.9 (5'—$OCH_3$), 55.0 (C-2), 47.3 ($CH_2Cl$), 41.2 (C-1)

Anal. Calculated for $C_{25}H_{24}ClN_3O_4$: C, 64.4, H, 5.2, N, 9.0, Cl, 7.6. Found: C, 64.8; H, 5.3, N, 8.8 Cl, 7.6%.

EXAMPLE C

Preparation of 1-(chloromethyl)-5-nitro-3-[(5-nitroindol-2-yl)carbonyl]-1,2-dihydro-3H-benz[e]indole (14b).

A solution of 13 (280 mg, 0.77 mmol) in HCl-saturated dioxane (10 mL) was stirred at 10° C. for 2 h, then evaporated to dryness under reduced pressure below 30° C. 5-Nitroindole-2-carboxylic acid [S. M. Parmerter, J. Amer. Chem. Soc. 80, 1958, 4621–4625] (167 mg, 0.81 mmol) EDCI.HCl (370 mg, 1.93 mmol) and DMA (3 mL) were then added and the mixture was stirred at 20° C. for 2 h. Addition of dilute $KHCO_3$ precipitated a yellow solid which was collected, washed well with water and recrystallised from THF to give 14b (282 mg, 81%), mp >300° C. $^1H$ NMR [($CD_3)_2SO$] δ 12.56 (s, 1 H, NH), 9.14 (s, 1 H, H-4), 8.74 (d, J=2.2 Hz, 1 H, H-4'), 8.35 (dd, J=7.0, 2.7 Hz, 1 H, H-6), 8.24 (dd, J=6.8, 2.7 Hz, 1 H, H-9), 8.12 (dd, J=9.1, 2.3 Hz, 1 H, H-6'), 7.80–7.72 (m, 2 H, H-7,8), 7.64 (d, J=9.1 Hz, 1 H, H-7'), 758 (s, 1 H, H-3'), 4.96 (t, J=10.1 Hz, 1 H, H-2), 4.71 (dd, J=10.8, 2.3 Hz, 1 H, H-2), 4.68–4.61 (m, 1 H, H-1), 4.18–4.09 (m, 2 H, $CH_2Cl$).

Anal. Calculated for $C_{22}H_{15}ClN_4O_5$: C, 58.6; H, 3.4; N, 12.4; Cl, 7.9. Found: C, 58.6; H, 3.4; N, 12.3; Cl, 7.7%.

EXAMPLE D

Preparation of 5-amino-3-[(5-aminoindol-2-yl)carbonyl]-1-(chloromethyl)-1,2-dihydro-3H-benz[e]indole (15b).

A solution of the preceding dinitro compound 14b (170 mg, 0.38 mmol) in THF (120 mL) was hydrogenated over $PtO_2$ at 50 psi for 2 h. After removal of the catalyst, the solution was concentrated to a small volume under reduced pressure below 25° C. and diluted with $iPr_2O$ to give 15b (136 mg, 92%), mp >300° C. $^1H$ NMR [($CD_3)_2SO$] δ 11.23 (d, J=1.4 Hz, 1 H, NH), 8.07 (d, J=8.4 Hz, 1 H, H-6), 7.75 (d, J=8.2 Hz, 1 H, H-9), 7.70 (s, 1 H, H-4), 7.45 (t, J=7.5 Hz, 1 H, H-8), 7.27 (t, J=7.7 Hz, 1 H, H-7), 7.21 (d, J=8.6 Hz, 1 H, H-7'), 6.88 (d, J=1.8 Hz, 1 H, H-3'), 6.76 (d, J=1.8 Hz, 1 H, H-4'), 6.68 (dd, J=8.6, 2.1 Hz, 1 H, H-6'), 5.96 (s, 2 H, dihydroindole $NH_2$), 4.70 (dd, J=10.9, 8.9 Hz, 1 H, H-2), 4.64 (br, s, 2 H, indole $NH_2$), 4.49 (dd, J=11.0, 1.6 Hz, 1 H, H-2), 4.15–4.07 (m, 1 H, H-1), 3.97 (dd, J=11.0, 3.0 Hz, 1 H, CHHCl), 3.74 (dd, J=11.0, 8.0 Hz, 1 H, CHHCl).

Anal. Calculated for $C_{22}H_{19}ClN_4O$: C, 67.5; H, 5.9; N, 12.1; Cl, 7.7. Found: C, 67.3; H, 5.6; N, 12.2; Cl, 7.3%.

EXAMPLE E

Preparation of 3-[[5-(acetylamino)indol-2-yl]carbonyl]-1-(chloromethyl)-5-nitro-1,2-dihydro-3H-benz[e]indole (14c).

Deprotection of 13 (300 mg, 0.83 mmol) as in Example C, and treatment with 5-acetylaminoindole-2-carboxylic acid [M. A. Warpehoski et al., J. Med. Chem. 31, 1988, 590–603] (181 mg, 0.83 mmol) and EDCI.HCl (397 mg, 2.07 mmol) in DMA (3 mL) gave 14c (310 mg, 79%), mp (THF) 252–253° C. $^1H$ NMR [$(CD_3)_2SO$] δ 11.77 (d, J=1.2 Hz, 1 H, indole NH), 9.86 (s, 1 H, NHCO), 9.16 (s, 1 H, H-4), 8.35 (dd, J=7.1, 2.6 Hz, 1 H, H-6), 8.24 (dd, J=6.8, 2.5 Hz, 1 H, H-9), 8.10 (d, J=1.3 Hz, H-4'), 7.79–7.70 (m, 2 H, H-7,8), 7.43 (d, J=8.8 Hz, 1 H, H-7'), 7.35 (dd, J=8.8, 1.8 Hz, 1 H, H-6'), 7.27 (d, J=1.8 Hz, 1 H, H-3'), 4.94 (t, J=10.2 Hz, 1 H, H-2), 4.71 (dd, J=11.0, 2.3 Hz, 1 H, H-2), 4.66–4.58 (m, 1 H, H-1), 4.13 (d, J=4.3 Hz, 2 H, $CH_2Cl$), 2.06 (s, 3 H, $COCH_3$).

Anal. Calculated for $C_{24}H_{19}ClN_4O_4$: C, 62.2; H, 4.1; N, 12.1; Cl, 7.7. Found: C, 62.3; H, 4.3; N, 12.1; Cl, 7.9%.

EXAMPLE F

Preparation of 3-[[5-(acetylamino)indol-2-yl]carbonyl]-5-amino-1-(chloromethyl)-1,2-dihydro-3H-benz[e]indole (15c).

A solution of 14c (170 mg, 0.37 mmol) in THF (60 mL) was hydrogenated over $PtO_2$ at 50 psi for 2 h. After removal of the catalyst, the solution was concentrated to a small volume under reduced pressure below 25° C. and diluted with EtOAc/$iPr_2O$ to give 15c (141 mg, 89%). mp >300° C. $^1H$ NMR [$(CD_3)_2SO$] δ 11.61 (d, J=1.4 Hz, 1 H, indole NH), 9.84 (s, 1 H, NHCO), 8.08 (d, J=8.5 Hz, 1 H, H-6), 8.05 (d, J=1.4 Hz, 1 H, H-4'), 7.76 (d, J=8.2 Hz, 1 H, H-9), 7.71 (s, 1 H, H-4), 7.46 (t, J=7.5 Hz, 1 H, H-8), 7.42 (d, J=8.9 Hz, 1 H, H-7'), 7.33 (dd, J=8.8, 1.9 Hz, 1 H, H-6'), 7.29 (t, J=7.5 Hz, 1 H, H-7), 7.14 (d, J=1.7 Hz, 1 H, H-3'), 5.98 (s, 2 H, $NH_2$), 4.74 (dd, J=10.8, 9.0 Hz, 1 H, H-2), 4.51 (dd, J=11.0, 1.6 Hz, 1 H, H-2), 4.17–4.08 (m, 1 H, H-1), 3.97 (dd, J=11.0, 3.0 Hz, 1 H, CHHCl), 3.77 (dd, J=10.9, 7.8 Hz, 1 H, CHHCl), 2.06 (s, 3 H, $CH_3$).

Anal. Calculated for $C_{24}H_{21}ClN_4O_2$: C, 66.6; H, 4.9; N, 12.9; Cl, 8.2. Found: C, 66.3; H, 5.2; N, 12.7; Cl, 8.0%.

EXAMPLE G

Preparation of 1-(chloromethyl)-3-[(5-methoxyindol-2-yl)carbonyl]-5-nitro-1,2-dihydro-3H-benz[e]indole (14d).

Deprotection of 13 (260 mg, 0.72 mmol) as in Example C, and reaction with 5-methoxyindole-2-carboxylic acid (145 mg, 0.76 mmol) and EDCI.HCl (344 mg, 1.80 mmol) in DMA (3 mL) gave 14d (237 mg, 76%), mp (2×EtOAc/$iPr_2O$) 241–243° C. $^1H$ NMR [$(CD_3)_2SO$] δ 11.73 (d, J=1.3 Hz, 1 H, NH), 9.16 (s, 1 H, H-4), 8.35 (dd, J=7.2, 2.5 Hz, 1 H, H-6), 8.23 (dd, J=6.9, 2.4 Hz, 1 H, H-9), 7.79–7.70 (m, 2 H, H-7,8), 7.42 (d, J=8.9 Hz, 1 H, H-7'), 7.20 (d, J=1.9 Hz, 1 H, H-3'), 7.17 (d, J=2.4 Hz, 1 H, H-4'), 6.94 (dd, J=9.0, 2.4 Hz, 1 H, H-6'), 4.93 (dd, J=10.6, 9.2 Hz, 1 H, H-2), 4.70 (dd, J=10.9, 2.4 Hz, 1 H, H-2), 4.65–4.57 (m, 1 H, H-1), 4.18–4.07 (m, 2 H, $CH_2Cl$), 3.79 (s, 3 H, $OCH_3$).

Anal. Calculated for $C_{23}H_{18}ClN_3O_4$: C, 63.4; H, 4.2; N, 9.6; Cl, 8.1. Found: C, 63.1; H, 4.2; N, 9.9; Cl, 8.0%.

EXAMPLE H

Preparation of 5-amino-1-(chloromethyl)-3-[(5-methoxyindol-2-yl)carbonyl]-1,2-dihydro-3H-benz[e]indole (15d).

A solution of 14d (140 mg, 0.32 mmol) in THF (10 mL) was hydrogenated over $PtO_2$ at 50 psi for 2 h. After removal of the catalyst, the solution was concentrated to a small volume below 25° C. and diluted with $iPr_2O$ to give 15d (124 mg, 95%), mp 250–255° C. $^1H$ NMR [$(CD_3)_2SO$] δ 11.56 (d, J=1.6 Hz, 1 H, NH), 8.08 (d, J=8.4 Hz, 1 H, H-6), 7.76 (d, J=8.2 Hz, 1 H, H-9), 7.70 (s, 1 H, H-4), 7.46 (t, J=7.6 Hz, 1 H, H-8), 7.40 (d, J=8.8 Hz, 1 H, H-7'), 7.28 (t, J=7.6 Hz, 1 H, H-7), 7.16 (d, J=2.4 Hz, 1 H, H-4'), 7.08 (d, J=1.8 Hz, 1 H, H-3'), 6.91 (dd, J=8.8, 2.5 Hz, 1 H, H-6'), 5.98 (s, 2 H, $NH_2$), 4.73 (dd, J=10.8, 8.9 Hz, 1 H, H-2), 4.51 (dd, J=10.9, 1.7 Hz, 1 H, H-2), 4.17–4.08 (m, 1 H, H-1), 3.98 (dd, J=11.0, 3.1 Hz, 1 H, CHHCl), 3.78 (s, 3 H, $OCH_3$), 3.75 (dd, J=11.0, 8.1 Hz, 1 H, CHHCl).

Anal. Calculated for $C_{23}H_{20}ClN_3O_2$: C, 68.1; H, 5.0; N, 10.4; Cl, 8.7. Found: C, 67.9; H, 5.3; N, 10.2; Cl, 8.5%.

EXAMPLE I

Preparation of 1-(chloromethyl)-3-[[5-[2-(dimethylamino)ethoxy]indol-2-yl]carbonyl]-5-nitro-1,2-dihydro-3H-benz[e]indole (14e).

A stirred solution of 4-[2-(dimethylamino)ethoxy]aniline [R Paul et al, J. Med. Chem. 36, 1993, 2716–2725](3.61 g, 20 mmol) in water (34 mL) and concentrated HCl (10 mL) was diazotized at 0° C. with a solution of $NaNO_2$ (1.52 g, 22 mmol) in water (4 mL). The cold solution was added in one portion to a vigorously stirred ice-cold mixture of ethyl 2-methylacetoacetate (3.03 g, 21 mmol), anhydrous NaOAc (17 g), EtOH (25 mL), and freshly added ice (20 g). After stirring at 20° C. for 1 h, the mixture was cooled to 0° C., basified by the slow addition of solid $Na_2CO_3$, and extracted immediately with $CH_2Cl_2$ (×2). The combined organic layers were washed with water, dried ($Na_2SO_4$), and evaporated. The residue was extracted with hot petroleum ether (bp 60–65° C.) in the presence of decolorizing charcoal, and the clarified solution was evaporated. The remaining oil (4.55 g) was dissolved in absolute EtOH (6 mL) and HCl-saturated EtOH (10 mL) was added. After heating at reflux for 25 min, the solution was concentrated and the residue was partitioned between dilute $Na_2CO_3$ and $CH_2Cl_2$. The organic layer was washed with water and NaCl solution, dried, and evaporated. The residue was triturated with $iPr_2O$/hexanes and the resulting solid was recrystallized from $iPr_2O$/hexanes to give ethyl 5-[2-(dimethylamino)ethoxy]indole-2-carboxylate (1.32 g, 24% overall yield) as needles, mp 110° C. $^1H$ NMR [$(CD_3)_2SO$] δ 11.72 (s, 1 H, NH), 7.34 (d, J=9.0 Hz, 1 H, H-7), 712 (d, J=2.4 Hz, 1 H, H-4), 7.03 (d, J=1.6 Hz, 1 H, H-3), 6.91 (dd, J=9.0, 2.4 Hz, 1 H, H-6), 4.32 (q, J=7.1 Hz, 2 H, $CH_2CH_3$), 4.03 (t, J=5.9 Hz, 2 H, $OCH_2$), 2.63 (t, J=5.9 Hz, 2 H, $OCH_2CH_2$), 2.22 (s, 6 H, $N(CH_3)2$), 1.33 (t, J=7.1 Hz, 3 H, $CH_2CH_3$).

Anal. Calculated for $C15H_{20}N20_3$: C, 65.2; H, 7.3; N, 10.1. Found: C, 64.9; H, 7.0; N, 10.2%.

A mixture of the above ester (0.75 g, 2.7 mmol), $Cs_2CO_3$ (3.0 g), MeOH (6 mL), and water (3mL) was heated at reflux for 2 h, then evaporated to dryness. The residue was dissolved in water (5 mL) and the filtered solution was adjusted to pH 6.5 with HCl and cooled to 0° C. for 24 h. The resulting crystalline solid was collected, washed with ice-cold water and $Me_2CO$, and treated with dry HCl/dioxane/EtOAc. The resulting solid was recrystallized from MeOH/EtOAc/trace HCl to give 5-[2-(dimethylamino)ethoxy]indole-2-carboxylic acid hydrochloride (0.69 g, 89%) as colourless plates, mp 239–240° C. (dec.). $^1H$ NMR [$(CD_3$ ₂SO] δ 12.88 (br s, 1 H, CO₂H), 11.69 (s, 1 H, indole NH), 10.56 (br s, 1 H, NH+), 7.37 (d, J=9.1 Hz, 1 H, H-7), 7.20 (d, J=2.4 Hz, 1 H, H-4), 7.01 (d, J=1.7 Hz, 1 H, H-3), 6.98 (dd, J=9.0, 2.4 Hz, 1 H, H-6), 4.34 (t, J=5.1 Hz, 2 H, OCH₂), 3.50 (t, J=5.1 Hz, 2 H, OCH₂CH₂), 2.85 (s, 6 H, N(CH₃)2).

Anal. Calculated for C13H16N2O₃.HCl: C, 54.8; H, 6.0; N, 9.8; Cl, 12.5. Found: C, 54.8; H, 5.9; N, 9.9; Cl, 12.3%.

Deprotection of 13 (260 mg, 0.72 mmol) as in Example C, the reaction of the product with the above 5-[2-(dimethylamino)ethoxy]indole-2-carboxylic acid hydrochloride (210 mg, 0.74 mmol), EDCI.HCl (345 mg, 1.80 mmol) and DMA (3 mL) gave crude material that was purified by precipitation from a CH₂Cl₂ solution at 20° C. with iPr₂O (2×) to give 14e (237 mg, 67%), mp 224–227° C. ¹H NMR [(CD₃)₂SO] δ 11.72 (d, J=1.5 Hz, 1 H, NH), 9.16 (s, 1 H, H-4), 8.35 (dd, J=7.2, 2.5 Hz, 1 H, H-6), 8.23 (dd, J=6.9, 2.5 Hz, 1 H, H-9), 7.79–7.71 (m, 1 H, H-7,8), 7.41 (d, J=8.9 Hz, 1 H, H-7'), 7.21–7.16 (m, 2 H, H-3',4', 6.94 (dd, J=9.0, 2.4 Hz, 1 H, H-6'), 4.93 (dd, J=10.6, 9.8 Hz, 1 H, H-2), 4.70 (dd, 10.9, 2.4 Hz, 1 H, H-2), 4.65–4.58 (m, 1 H, H-1), 4.18–4.09 (m, 2 H, CH₂Cl), 4.07 (t, J=5.9 Hz, 2 H, OCH₂), 2.66 (t, J=5.8 Hz, OCH₂CH₂), 2.24 (s, 6 H, N(CH₃)2).

Anal. Calculated for C₂₆H₂₅ClN₄O₄: C, 63.4; H, 5.1; N, 11.4; Cl, 7.2. Found: C, 63.5; H, 5.1; N, 11.3; Cl, 7.2%.

EXAMPLE J

Preparation of 5-amino-1-(chloromethyl)-3-[[5-[2-(dimethylamino)ethoxy]indol-2-yl]carbonyl]-1,2-dihydro-3H-benz[e]indole (15e).

A solution of 14e (125 mg, 0.25 mmol) in THF (10 mL) was hydrogenated over PtO₂ at 50 psi for 2 h. After removal of the catalyst, the solution was concentrated to a small volume under reduced pressure below 25° C. and diluted with iPr₂O to give 15e (115 mg, 98%): mp >250° C.; ¹H NMR [(CD₃)₂SO] δ 11.56 (d, J=1.4 Hz, 1 H, NH), 8.08 (d, J=8.5 Hz, 1 H, H-6), 7.76 (d, J=8.2 Hz, 1 H, H-9), 7.70 (s, 1 H, H-4), 7.46 (t, J=7.4 Hz, 1 H, H-8), 7.39 (d, J=8.9 Hz, 1 H, H-7'), 7.28 (t, J=7.7 Hz, 1 H, H-7), 7.17 (d, J=2.2 Hz, 1 H, H-4'), 7.07 (d, J=1.8 Hz, 1 H, H-3'), 6.91 (dd, J=8.9, 2.4 Hz, 1 H, H-6'), 5.98 (s, 2 H, NH₂), 4.73 (dd, J=10.6, 9.1 Hz, 1 H, H-2), 4.51 (dd, J=10.9, 1.4 Hz, 1 H, H-2), 4.16–4.08 (m, 1 H, H-1), 4.06 (t, J=5.9 Hz, 2 H, OCH₂), 3.98 (dd, J=10.9, 3.0 Hz, 1 H, CHHCl), 3.75 (dd, J=10.9, 8.1 Hz, 1 H, CHHCl), 2.65 (t, J=5.9 Hz, 2 H, OCH₂CH₂), 2.24 (s, 6 H, N(CH₃)2).

Anal. Calculated for C₂₆H₂₇ClN₄O₂: C, 67.5; H, 5.9; N, 12.1; Cl, 7.7. Found: C, 67.3; H, 5.6; N, 12.2; Cl, 7.8%.

EXAMPLE K

Preparation of 1-(chloromethyl)-3-[[6-[2-(dimethylamino) ethoxy]-5-methoxyindol-2-yl]carbonyl]-5-nitro-1,2-dihydro-3H-benz[e]indole (14f).

A mixture of vanillin (10.00 g, 65.7 mmol), K₂CO₃ (45.4 g, 329 mmol), 1,2-dichloroethane (104 mL, 1.31 mol), and DMF (300 mL) was stirred at 65–70° C. for 16 h. The dichloroethane was evaporated and the remaining slurry was poured onto ice. The oil that separated was extracted with Et₂O (×4) and EtOAc (×3). The combined extracts were washed with water (×3), dried (Na₂SO₄/MgSO₄), and evaporated to give a clear oil that solidified upon trituration with hexanes. Crystallization from Et2O gave 4-(2-chloroethoxy)-3-methoxybenzaldehyde (12.04 g, 85%) as white needles, mp 60–61° C. ¹H NMR (CDCl₃) δ 9.87 (s, 1 H, CHO), 7.46 (dd, J=8.0, 2.0 Hz, 1 H, H-6), 7.43 (d, J=2.0 Hz, 1 H, H-5), 6.99 (d, J=8.0 Hz, 1 H, H-2), 4.36 (t, J=6.1 Hz, 2 H, OCH₂), 3.94 (s, 3 H, OCH₃), 3.89 (t, J=6.1 Hz, 2 H, CH₂Cl); ¹³C NMR δ 190.8 (CHO), 153.9 (C-4), 150.0 (C-3), 130.8 (C-1), 126.3 (C-6), 112.3 (C-2), 109.8 (C-5), 68.9 (OCH₂), 56.0 (OCH₃), 41.2 (CH₂Cl).

Anal. Calculated for C₁₀H₁₁ClO₃: C, 56.0; H, 5.2; N, 16.5. Found: C, 56.3; H, 5.1; N, 16.7%.

A solution of the above aldehyde (4.50 g, 20.97 mmol) and methyl azidoacetate (8.20 g, 71.3 mmol) in MeOH (18 mL) was added to a cooled (ice/salt) solution of sodium methoxide (from 7.45 g of sodium 62.9 mmol) in MeOH (36 mL) over 1 h. The white slurry was allowed to stand at 5° C. for 1.5 h then at −15° C. for 18 h. Ice cold water (200 mL) was added and the precipitate was removed by filtration, washed with water, and dissolved in CH₂Cl₂. The CH₂Cl₂ solution was washed with water, dried (MgSO₄), and evaporated to give methyl (-azido-4-(2-chloroethoxy)-3-methoxycinnamate as fine unstable off-white needles (5.08 g, 78%), mp 115–116° C. (dec.), that were used without further purification. ¹H NMR (CDCl₃) δ 7.52 (d, J=2.0 Hz, 1 H, H-2), 7.33 (dd, J=8.6, 2.0 Hz, 1 H, H-6), 6.89 (d, J=8.6 Hz, 1 H, H-5), 6.87 (s, 1 H, H-β), 4.31 (t, J=6.2 Hz, 2 H, OCH₂), 3.91, 3.90 (2×s, 3 H each, OCH₃), 3.85 (t, J=6.2 Hz, 2 H, CH₂Cl); ¹³C NMR δ 164.1 (CO₂), 149.2, 148.7 (C-3,4), 127.3 (C-1), 125.6, 124.7 (C-6,β), 123.7 (C-α), 113.9, 113.3 (C-2,5), 69.0 (OCH₂), 56.1 (OCH₃), 52.8 (CO₂CH₃), 41.4 (CH₂Cl).

A warmed (40° C.) solution of the above azidocinnamate (5.08 g, 16.3 mmol) in xylenes (140 mL) was added to boiling xylenes (60 mL) over 1 h. After a further 15 min at reflux, most of the xylene was removed by distillation. The precipitate that formed in the cooled residue was isolated by filtration, washed with CHCl₃ and hexanes, and crystallized from MeOH to give methyl 6-(2-chloroethoxy)-5-methoxyindole-2-carboxylate (2.423 g, 52%) as fluffy white needles, mp 164–166° C. (sublimes 110° C.). ¹H NMR [(CD₃)₂SO] δ 11.65 (br s, 1 H, NH), 7.13 (s, 1 H, H-4), 7.03 (d, J=1.6 Hz, 1 H, H-3), 6.91 (s, 1 H, H-7), 4.24 (t, J=5.2 H, 2 H, OCH₂), 3.98 (t, J=5.2 H, 2 H, CH₂Cl), 3.84 3.78 (2×s, 3 H each, OCH₃); ¹³C NMR δ 161.5 (CO₂), 147.8, 145.8, 132.4, 125.5, 120.3 (C-2, 3a, 5, 6, 7a), 107.8 (C-3), 103.0 (C-4), 96.3 (C-7), 68.9 (OCH₂), 55.7 (OCH₃), 51.4 (CO₂CH₃), 42.9 (CH₂Cl).

Anal. Calculated for C₁₃H₁₄ClNO₄: C, 55.0; H, 5.0; N, 4.9; Cl, 12.5. Found: C, 54.9; H, 5.2; N, 4.9; Cl, 12.4%. Purification of the evaporated mother liquors by flash chromatography (CH₂Cl₂) and by crystallization from 1,2-dichloroethane then MeOH gave further product (0.42 g, 9%).

A mixture of the above ester (1.00 g, 3.52 mmol), CsCO₃ (1.723 g, 5.29 mmol), 95% EtOH (20 mL), and water (10 mL) was stirred at reflux for 6 h. Water (15 mL) was added and the EtOH was evaporated. The solution was filtered through Celite and acidified with 2 M HCl. The precipitate that formed was collected by filtration, washed with water, and dried to give 6-(2-chloroethoxy)-5-methoxyindole-2-carboxylic acid (0.95 g, 100%) as a white powder, which crystallized from MeOH as white needles, mp 187–189° C. ¹H NMR [(CD₃)₂SO] δ 12.63 (br s, 1 H, CO₂h), 11.47 (s, 1 H, NH), 7.12 (s, 1 H, H-4), 6.97 (d, J=1.6 Hz, 1 H, H-3), 6.91 (s, 1 H, H-7), 4.23 (t, J=5.2 Hz, 2 H, OCH₂), 3.97 (t, J=5.2 Hz, 2 H, CH₂Cl), 3.78 (s, 3 H, OCH₃); ¹³C NMR 162.5 (CO₂), 147.5, 145.6, 132.1, 126.9, 120.4 (C-2,3a,5,6,7a), 107.4 (C-3), 103.1 (C-4), 96.5 (C-7), 68.9 (OCH₂), 55.7 (OCH₃), 43.0 (CH₂Cl).

Anal. Calculated for C₁₂H₁₂ClNO₄: C, 53.4; H, 4.5; N, 5.2. Found: C, 53.2; H, 4.4; N, 5.2%.

A mixture of the above acid (1.20 g, 4.45 mmol), 25% aqueous Me₂NH (16 mL, 89 mmol), Na₂CO₃ (1.18 g, 11.1 mmol), and water (80 mL) was heated at 100° C. for 1.25 h, then evaporated. The residue was taken up in 0.4 M aqueous Na$_2$CO$_3$ (30 mL), extracted with Et$_2$O (×2), acidified to pH 1 with 2 M HCl, and evaporated. The residue was extracted with hot CH$_3$CN (×8) and the extracts were concentrated. The precipitate that formed was removed by filtration and washed with CH$_3$CN and Et$_2$O to give 6-[2-(dimethylamino) ethoxy]-5-methoxyindole-2-carboxylic acid hydrochloride (1.06 g, 76%) as a hydroscopic tan solid, mp 204–205° C. dec. $^1$H NMR [(CD$_3$)$_2$SO] δ 12.7 (br s, 1 H, CO$_2$H), 11.57 (d, J=1.9 Hz, 1 H, indole NH), 10.7 (br s, 1 H, NH+), 7.16 (s, 1 H, H-4), 6.98 (d, J=1.9 Hz, 1 H, H-3), 6.96 (s, 1 H, H-7), 4.38 (t, J=4.9 Hz, 2 H, OCH$_2$), 3.80 (s, 3 H, OCH$_3$), 3.53 (t, J=4.9 Hz, 2 H, NCH$_2$), 2.88 (s, 6 H, N(CH$_3$)$_2$); $^{13}$C NMR δ 162.5 (CO$_2$), 147.0, 145.6, 132.0, 127.1, 120.7 (C-2, 3a, 5, 6, 7a), 107.4 (C-3), 102.9 (C-4), 97.1 (C-7), 64.0 (OCH$_2$), 55.7 (OCH$_3$), 55.3 (NCH$_2$), 42.9 (N(CH$_3$)2).

Deprotection of 13 (260 mg, 0.72 mmol) as in Example C, and reaction of the product with 6-[2-(dimethylamino) ethoxy]-5-methoxyindole-2-carboxylic acid hydrochloride (230 mg, 0.73 mmol), EDCI.HCl (345 mg, 1.80 mmol) and DMA (3 mL) at 20° C. for 3 h gave a solid. This was shaken with dilute KHCO$_3$ and the resulting gelatinous solid was collected and chromatographed on alumina-90. Elution with EtOAc/MeOH (10:1) provided the crude product which was recrystallised from EtOAc/i-Pr$_2$O, followed by CH$_2$Cl$_2$/ petroleum ether, to give 14f (180 mg, 48%), mp 224–234 (C (dec.). $^1$H NMR [(CD$_3$)$_2$SO] δ 11.54 (d, J=1.6 Hz, 1 H, NH), 9.17 (s, 1 H, H-4), 8.34 (dd, J=7.5, 2.2 Hz, 1 H, H-6), 8.22 (dd, J=7.1, 1.8 Hz, 1 H, H-9), 7.79–7.69 (m, 2 H, H-7,8), 7.17 (d, J=1.6 Hz, 1 H, H-3'), 7.16 (s, 1 H, H-4' or 7'), 6.99 (s, 1 H, H-4' or 7'), 4.91 (t, J=10.2 Hz, 1 H, H-2), 4.68 (dd, J=10.9, 2.4 Hz, 1 H, H-2), 4.65–4.57 (m, 1 H, H-1), 4.17–4.09 (m, 2 H, CH$_2$Cl), 4.06 (t, J=6.0 Hz, 2 H, OCH$_2$), 3.79 (s, 3 H, OCH$_3$), 2.69 (t, J=5.9 Hz, 2 H, OCH$_2$CH$_2$), 2.26 (s, 6 H, N(CH$_3$)$_2$).

Anal. Calculated for C$_{27}$H$_{27}$ClN$_4$O$_5$: C, 62.0; H, 5.2; N, 10.7. Found: C, 61.8; H, 5.2; N, 10.4%.

EXAMPLE L

Preparation of 5-amino-1-(chloromethyl)-3-[[6-[2-(dimethylamino)ethoxy]-5-methoxyindol-2-yl]carbonyl]-1, 2-dihydro-3H-benz[e]indole (15f).

A solution of 14f (130 mg, 0.25 mmol) in THF (20 mL) was hydrogenated over PtO$_2$ (30 mg) at 55 psi for 2 h. The catalyst was removed and the solution was concentrated under reduced pressure below 30° C. The residue was dissolved in a small volume of CH$_2$Cl$_2$, the solution was diluted with petroleum ether to precipitate impurities which were removed by filtration, and then further addition of petroleum ether precipitated 15f (87 mg, 71%), mp 130–133° C. $^1$H NMR [(CD$_3$)$_2$SO] δ 11.38 (d, J=1.6 Hz, 1 H, NH), 8.07 (d, J=8.5 Hz, 1 H, H-6), 7.75 (d, J=8.3 Hz, 1 H, H-9), 7.72 (s, 1 H, H-4), 7.45 (t, J=7.4 Hz, 1 H, H-8), 7.27 (t, J=7.7 hz, 1 H, H-7), 7.15 (s, 1 H, H-3'), 7.05 (s, 1 H, H-4' or 7'), 6.99 (s, 1 H, H-4' or 7'), 5.96, 5.94 (2×s, 2 H, NH$_2$), 4.71 (dd, J=10.6, 9.1 Hz, 1 H, H-2), 4.50 (dd, J=10.9 Hz, 1.6 Hz, 1 H, H-2), 4.16–4.08 (m, 1 H, H-1), 4.05 (t, J=6.0 Hz, 2 H, OCH$_2$), 3.98 (dd, J=11.0, 3.0 Hz, 1 H, CHHCl), 3.79 (s, 1 H, OCH$_3$), 3.74 (dd, J=10.9, 8.2 Hz, 1 H, CHHCl), 2.68 (t, J=5.9 Hz, 2 H, OCH$_2$CH$_2$), 2.25 (s, 6 H, N(CH$_3$)2).

Anal. Calculated for C$_{27}$H$_{29}$ClN$_4$O$_3$.0.5H$_2$O: C, 64.6; H, 6.0; N, 11.2; Cl, 7.1. Found: C, 64.4; H, 5.9; N, 11.2; Cl, 6.6%.

EXAMPLE M

Preparation of 1-(chloromethyl)-3-[[7-[2-(dimethylamino) ethoxy]-5-methoxyindol-2-yl]carbonyl]-5-nitro-1,2-dihydro-3H-benz[e]indole (14g).

A mixture of 5-methoxy-3-methyl-2-nitrophenol [J. Atkinson et al., J. Org. Chem. 56, 1991, 1788–1800](5.00 g, 27.3 mmol), 2-(dimethylamino)ethyl chloride hydrochloride (4.33 g, 30 mmol), K$_2$CO$_3$ (15.1 g, 109 mmol), NaI (0.41 g, 2.7 mmol), an butanone (50 mL) was heated at reflux for 1 h then cooled to room temperature. A mi8xture of 2-dimethylaminoethyl chloride hydrochloride (4.33 g, 30 mmol), K2CO$_3$ (7.6 g, 54.6 mmol), and butanone (15 mL) that had been shaken for 5 min was added and the mixture was heated at reflux for 1.5 h. The mixture was concentrated and the remaining slurry was diluted with water and extracted with EtOAc (×4). The combined extracts were washed with 2 N aqueous Na$_2$CO$_3$ (×10) and extracted with 2 N aqueous HCl (×5). The combined extracts were washed with EtOAc, made basic with Na$_2$CO$_3$, and extracted with EtOAc (×4). These extracts were dried (MgSO$_4$) and evaporated to give 2-(5-methoxy-3-methyl-2-nitrophenyloxy)-N, N-dimethylethanamine (4.38 g, 63%) as a yellow oil; $^1$H NMR (CDCl$_3$) δ 6.38 (d, J=2.4 Hz, 1 H, H-6'), 6.32 (d, J=2.4 Hz, 1 H, H-4'), 4.12 (t, J=5.8 Hz, 2 H, OCH$_2$), 3.81 (s, 3 H, OCH$_3$), 2.73 (t, J=5.8 Hz, 2 H, NCH$_2$), 2.31 (s, 6 H, N(CH$_3$)$_2$), 2.28 (s, 3 H, 3(—CH$_3$); $^{13}$C NMR δ 161.0 (C-5'), 151.8 (C-1'), 136.1 (C-2'), 132.7 (C-3'), 106.7 (C-4'), 97.9 (C-6'), 68.1 (OCH$_2$), 57.4 (NCH$_2$), 55.5 (OCH$_3$), 45.8 (N(CH$_3$)$_2$), 17.7 (3'—CH$_3$). Calc. for C$_{12}$H$_{18}$N2O$_4$, M+254.1267. Found, 254.1276. Starting material (1.178 g, 24%) was recovered from the basic washes by acidification and extraction.

A suspension of potassium (0.308 g, 7.87 mmol) in xylenes (6 mL) was heated to 100° C. and stirred rapidly as it was allowed to cool. The xylenes were removed and the potassium was washed with Et$_2$O (×3) and covered with Et$_2$O (10 mL). The mixture was treated with absolute EtOH (1.30 mL, 22.2 mmol) and stirred at reflux until the potassium had dissolved (3 h). The cooled mixture was treated with diethyl oxalate (1.07 mL, 7.87 mmol) then with a solution of the above nitrotoluene (2.00 g, 7.87 mmol) in dry Et$_2$O (5 mL). After 115 h, the dark red precipitate was removed by filtration and washed with Et$_2$O. The red solid (1.189 g) was dissolved in absolute EtOH (45 mL), acidified with AcOH (0.78 mL), and hydrogenated over Pd/C (10%, 0.44 g) at 1 atm H2 for 8 h. The mixture was filtered through Celite, concentrated, diluted with 0.2 M aqueous Na$_2$CO$_3$ (100 mL), and extracted with EtOAc (×4). The combined extracts were washed with water (×2), dried (Na$_2$SO$_4$), evaporated and purified by flash chromatography (2% Et$_3$N/ EtOAc) to give ethyl 7-[2-(dimethylamino)-ethoxy]-5-methoxyindole-2-carboxylate as a clear oil (0.44 g, 18%). $^1$H NMR (CDCl$_3$) δ 10.93 (br s, 1 H, NH), 7.09 (d, J=2.1 Hz, 1 H, H-3), 6.67 (d, J=2.0 Hz, 1 H, H-4), 6.43 (d, J=2.0 Hz, 1 H, H-6), 4.38 (q, J=7.0 Hz, 2 H, OCH$_2$CH$_3$), 4.16 (t, J=6.5 Hz, 2 H, OCH$_2$CH$_2$N), 3.88 (s, 3 H, OCH$_3$), 2.79 (t, J=7.0 Hz, 2 H, NCH$_2$), 2.37 (s, 6 H, N(CH$_3$)$_2$), 1.40 (t, J=6.5 Hz, 3 H, OCH$_2$CH$_3$); $^{13}$C NMR δ 161.9 (CO$_2$), 155.0, 146.0, 128.1, 127.7, 124.9 (C-2, 3a, 5, 7, 7a), 108.1 (C-3), 99.1 (C-4), 94.6 (C-6), 65.9 (OCH$_2$CH$_2$N), 60.6 (OCH$_2$CH$_3$), 58.3 (NCH$_2$), 55.6 (OCH$_3$), 45.1 (N(CH$_3$)$_2$), 14.4 (OCH$_2$CH$_3$). Calc for C16H$_{22}$N2O$_4$, M+306.1580. Found, 306.1577. Starting material (0.77 g, 39%) was recovered from the ethereal washes by extraction into acid, basification, and extraction with Et$_2$O.

A mixture of the above ester (0.410 g, 1.34 mmol), 95% EtOH (21 mL), and 1.0 M aqueous NaOH (2.7 mL, 2.7 mmol) was stirred at reflux for 1.5 h. The EtOH was evaporated, 2 M aqueous HCl (5 mL) was added, and the solution was evaporated. The residue was extracted with hot $CH_3CN$ (×3), and the extracts were concentrated with diluted with $Et_2O$. The precipitate that formed was collected by filtration and washed with $Et_2O$ to give 7-[2-(dimethylamino)ethoxy)-5-methoxyindole-2-carboxylic acid hydrochloride (0.372 g, 88%) as a white powder, mp 175–178° C. $^1$H NMR [$(CD_3)_2SO$] δ 12.85 (br s, 1 H, $CO_2H$), 11.52 (s, 1 H, indole NH), 10.48 (br s, 1 H, NH+), 7.00 (d, J=2.1 Hz, 1 H, H-3), 6.72 (d, J=2.1 Hz, 1 H, H-4), 6.49 (d, J=2.1 Hz, 1 H, H-6), 4.41 (t, J=4.8 Hz, 2 H, $OCH_2$), 3.76 (s, 3 H, $OCH_3$), 3.58 (t, J=4.8 Ha, 2 H, $NCH_2$), 2.88 (s, 6 H, $N(CH_3)_2$); $^{13}$C NMR δ 162.5 ($CO_2H$), 154.4 (C-5), 144.9 (C-7), 128.5, 127.6, 123.5 (C-2,3a, 7a), 107.7 (C-3), 97.6 (C-4), 94.4 (C-6), 61.3 ($OCH_2$), 55.3 ($OCH_3$), 54.8 ($NCH_2$), 42.0 ($N(CH_3)_2$).

Deprotection of 13 (160 mg, 0.44 mmol) as in Example C above, and the reaction of the product with EDCI.HCl (211 mg, 1.10 mmol), 7-[2-(dimkethylamino)ethoxy]-5-methoxyindole-2-carboxylic acid hydrochloride (145 mg, 0.46 mmol) and DMA )2 mL) at 20 (C for 3 h, followed by addition of dilute $KHCO_3$, precipitated a solid. This was recrystallised from $CH_2Cl_2$/i-$Pr_2O$ followed by $CH_2Cl_2$/EtOAc to give 14 g (193 mg, 84%), mp 230–240° C. (dec.). $^1$H NMR [$(CD_3)_2SO$] δ 11.64 (s, 1 H, NH), 9.11 (s, 1 H, H-4), 8.36 (dd, J=7.1, 2.7 Hz, 1 H, H-6), 8.23 (dd, J=6.7, 2.6 Hz, 1 H, H-9), 7.79–7.71 (m, 2 H, H-7,8), 7.14 (s, 1 H, H-3), 6.75 (d, J=2.0 Hz, 1 H, H-4' or 6'), 6.50 (d, J=2.0 Hz, 1 H, H-4' or 6'), 4.89 (dd, J=10.6, 9.6 Hz, 1 H, H-2), 4.65–4.55 (m, 2 H, H-1,2), 4.19 (t, J=5.7 Hz, 2 H, $OCH_2$), 4.16–4.05 (m, 2 H, $CH_2Cl$), 3.78 (s, 3 H, $OCH_3$), 2.74 (t, J=5.7 Hz, 2 H, $OCH_2CH_2$), 2.28 (s, 6 H, $N(CH_3)_2$).

Anal. Calculated for $C_{27}H_{27}ClN_4O_5$: C, 62.0; H, 5.2; N, 10.7; Cl, 6.8. Found: C, 61.9; H, 5.1; N, 10.9; Cl, 6.8%.

EXAMPLE N
Preparation of 5-amino-1-(chloromethyl)-3-[[7-[2-(dimethylamino)ethoxy]-5-methoxyindol-2-yl]carbonyl]-1, 2-dihydro-3H-benz[e]indole (15g).

A solution of 14g (120 mg, 0.23 mmol) in THF (45 mL) was hydrogenated over $PtO_2$ (30 mg) at 55 psi for 1.5 h. After removal of the catalyst the solution was concentrated to a small volume under reduced pressure below 30° C., and then diluted with petroleum ether to give 15g (140 mg. 92%), mp 109–111 (C. $^1$H NMR [$(CD_3)_2SO$] δ 11.41 (s, 1 H, NH), 8.07 (d, J=8.8 Hz, 1 H, H-6), 7.75 (d, J=8.2 Hz, 1 H, H-9), 7.64 (s, 1 H, H-4), 7.45 (t, J=7.5 Hz, 1 H, H-8), 7.28 (t, J=7.6 Hz, 1 H, H-7), 7.00 (d, J=1.2 Hz, 1 H, H-3'), 6.73 (d, J=1.9 Hz, 1 H, H-4' or 6'), 6.48 (d, J=2.0 Hz, 1 H, H-4'or 6'), 5.98, 5.96 (2×s, 2 H, $NH_2$), 4.66 (dd, J=10.7, 9.0 Hz, 1 H, H-2), 4.41 (dd, J=11.0, 1.4 Hz, 1 H, H-2), 4.19 (t, J=5.7 Hz, 2 H, $OCH_2$), 4.12–4.04 (m, 1 H, H-1), 3.96 (dd, J=10.9, 3.0 Hz, 1 H, CHHCl), 3.77 (s, 3 H, $OCH_3$), 3.72 (dd, J=11.0, 8.2 Hz, 1 H, CHHCl), 2.73 (t, J=5.7 Hz, 2 H, $OCH_2CH_2$), 2.28 (s, 6 H, $N(CH_3)_2$).

Anal. Calculated for $C_{27}H_{29}ClN_4O_3$·1.5$H_2O$: C, 62.4; H, 6.2; N, 10.8; Cl, 6.8. Found: C, 62.8; H, 6.3; N, 10.7; Cl, 6.8%.

EXAMPLE O
Preparation of 3-[[5-[(benzofuran-2-yl)carboxamido]indol-2-yl]carbonyl]-1-(chloromethyl)-5-nitro-1,2-dihydro-3H-benz[e]indole (14h).

Deprotection of 13 (300 mg, 0.83 mmol) as in Example C above, and reaction of the product with 5-[(benzofuran-2-yl)carboxamido]indole-2-carboxylic acid [D. L. Boger et al, Bioorg. Med. Chem. 3, 1995, 1429–1453] (278 mg, 0.87 mmol), EDCI.HCl (397 mg, 20.7 mmol) and DMA (10 mL) at 20 (C for 2 h, followed by addition of dilute $KHCO_3$, precipitated a yellow solid. This was collected, washed with water and recrystallised from THF/i-$Pr_2O$ followed by EtOAc to give 14h (341 mg, 73%), mp 277° C. (dec.). $^1$H NMR [$(CD_3)_2SO$] δ 11.88 (d, J=1.5 Hz, 1 H, indole NH), 10.50 (s, 1 H, NHCO), 9.18 (s, 1 H, H-4), 8.36 (dd, J=7.0, 2.8 Hz, 1 H, H-6), 8.27 (d, J=1.5 Hz, 1 H, H-4'), 8.25 dd, J=6.7, 2.6 Hz, 1 H, H-9), 7.84 (d, J=7.7 Hz, 1 H, H-4"), 7.80–7.71 (m, 3 H, H-7,8,7"), 7.78 (d, J=0.6 Hz, 1 H, H-3"), 7.65 (dd, J=8.9, 1.9 Hz, 1 H, H-6'), 7.55–7.48 (m, 1 H, H-6"), 7.52 (d, J=8.8 Hz, 1 H, H-7'), 7.38 (t, J=7.5 Hz, 1 H, H-5"), 7.34 (t, J=1.6 Hz, 1 H, H-3'), 4.97 (dd, J=10.6, 9.9 Hz, 1 H, H-2), 4.74 (dd, J=11.0, 2.3 Hz, 1 H, H-2), 4.68–4.60 (m, 1 H, H-1), 4.15 (d, J=4.3 Hz, 2 H, $CH_2Cl$).

Anal. Calculated for $C_{31}H_{21}ClN_4O_5$: C, 66.1; H, 3.9; N, 10.0; Cl, 6.2. Found: C, 65.9; H, 3.8; N, 9.9; Cl, 6.3%.

EXAMPLE P
Preparation of 5-amino-3-[[5-[(benzofuran-2-yl)carboxyamido]indol-2-yl]carbonyl]-1-(chloromethyl)-1,2-dihydro-3H-benz[e]indole (15h).

A solution of 14h (200 mg, 0.35 mmol) in THF (35 mL) was hydrogenated over $PtO_2$ at 50 psi for 2 h. THF was added to dissolve the precipitated product and after removal of the catalyst the solution was concentrated to a small volume below 25° C. under reduced pressure and diluted with i-$Pr_2O$ to give 15h (187 mg, 99%), mp >300 (C. $^1$H NMR [$(CD_3)_2SO$] δ 11.72 (d, J=1.3 Hz, 1 H, indole NH), 10.48 (s, 1 H, NHCO), 8. 22 (d, J=1.4 Hz, 1 H, H-4'), 8.09 (d, J=8.5 Hz, 1 H, H-6), 7.84 (d, J=7.8 Hz, 1 H, H-4"), 7.80–7.69 (m, 3 H, H-4,9,7"), 7.77 (s, 1 H, H-3"), 7.62 (dd, J=8.9, 1.9 Hz, 1 H, H-6'), 7.54–7.43 (m, 2 H, H-8,6"), 7.50 (d, J=8.6 Hz, 1 H, H-7'), 7.38 (t, J=7.5 Hz, 1 H, H-5"), 7.29 (t, J=7.7 Hz, 1 H, H-7), 7.21 (d, J=0.9 Hz, 1 H, H-3'), 6.00 & 5.98 (2×s, 2 H, $NH_2$), 4.77 (dd, J=10.9, 9.0 Hz, 1 H, H-2), 4.54 (dd, J=10.8, 1.3 Hz, 1 H, H-2), 4.19–4.10 (m, 1 H, H-1), 3.99 (dd, J=10.9, 2.9 Hz, 1 H, CHHCl), 3.79 (dd, J=10.9, 7.8 Hz, 1 H, CHHCl).

Anal. Calculated for $C_{31}H_{23}ClN_4O_3$·0.5 $H_2O$: C, 68.4; H, 4.5; N, 10.3. Found: C, 68.8; H, 4.5; N, 10.2%.

EXAMPLE Q
Preparation of 3-[(E)-4-(butyrylamino)-1-methyl-2-pyrroleacryloyl]-1-(chloromethyl)-5-nitro-1,2-dihydro-3H-benz[e]indole (14i).

A mixture of 1-methyl-4-nitro-2-pyrrolecarboxaldehyde [P. Fournari. Bull. Soc. Chim. Fr., 1963, 488–491] (0.24 g, 1.56 mmol), methyl triphenylphosphorylideneacetate (0.57 g, 1.71 mmol), and benzene (25 mL) was heated under reflux for 24 h. The still-warm solution was purified directly by dry flash chromatogrpahy (0–5% $Et_2O/CH_2Cl_2$) to give methyl (E)-1-methyl-4-nitro-2-pyrroleacrylate as a bright yellow solid (0.33 g, 100%), mp 146–147° C. $^1$H NMR ($CDCl_3$) δ 7.55 (d, J=1.8 Hz, 1 H, H-5), 7.47 (d, J=15.8 Hz, 1 H, H-β), 7.07 (d, J=1.8 Hz, 1 H, H-3), 6.27 (d, J=15.8 Hz, 1 H, H-α), 3.77, 3.75 (2×s, 3 H each, $CO_2CH_3$, $NCH_3$); $^{13}$C NMR δ 166.9 ($CO_2$), 136.6, 129.7 (C-2,4), 130.3, 125.4 (C-3, 5), 117.8, 106.0 (CH=CH), 51.8 ($CO_2CH_3$), 35.3 ($NCH_3$).

Anal. Calculated for $C_9H_{10}N_2O_4$: C, 51.4; H, 4.8; N, 13.3. Found: C, 51.4; H, 4.7; N, 13.3%.

Alternatively, a mixture of 1-methyl-4-nitro-2-pyrrolecarboxaldehyde (0.20 g, 1.30 mmol), malonic acid (0.68 g, 6.5 mmol), piperidine (2 drops), and pyridine (2 mL) was stirred at room temperature at for 20 h and at 100° C. for 4 h, then 30% aqueous $H_2SO_4$ (10 mL) was added. The precipitate that formed was removed by filtration and washed with water to give (E)-1-methyl-4-nitro-2- pyrroleacrylic acid as fine yellow needles (0.23 g, 92%). $^1$H NMR [(CD$_3$)$_2$SO] δ 12.35 (br s, 1 H, CO$_2$H), 8.13 (d, J=1.9 Hz, 1 H, H-5), 7.44 (d, J=15.9 Hz, 1 H, H-β), 7.41 (d, J=1.9 Hz, 1 H, H-3), 6.46 (d, J=15.9 Hz, 1 H, H-α), 3.79 (s, 3 H, NCH$_3$); $^{13}$C NMR δ 167.4 (CO$_2$H), 135.3, 129.9 (C-2,4), 130.6, 127.0, 118.6, 105.8 (C-3,5,α,β), 34.8 (NCH$_3$).

Anal calculated for C$_8$H$_8$N$_2$O$_4$: C, 49.9; H, 4.1; N, 14.3. Found: C, 49.0; H, 4.0; N, 14.1%.

A mixture of the above acid (0.10 g, 0.51 mmol), NaHCO$_3$ (0.10 g, 0.61 mmol). MeOH (6 mL), and water (2 mL) at reflux was treated with dimethyl sulfate (0.12 mL), heated at reflux for 1 h, diluted with water, and extracted with EtOAc (×3). The combined extracts were washed with water (×2), dried (MgSO$_4$), evaporated, and purified by dry flash chromatography (0–5% Et$_2$O/CH$_2$Cl$_2$) to give methyl (E)-1-methyl-4-nitro-2-pyrroleacrylate (63 mg, 59%).

A solution of this nitroester (50 mg, 0.24 mmol) in aqueous MeOH (1:12.5, 5.4 mL) at reflux was treated with iron powder (70 mg, 1.25 mmol) and butyric anhydride (0.40 mL, 2.45 mmol). After 30 min further butyric anhydride (0.10 mL, 0.61 mmol) was added, and 45 min after the addition of the iron the mixture was allowed to cool. The solids were removed by filtration and washed with MeOH and water. The combined filtrates were diluted with water and extracted with EtOAc (×3). The combined extracts were washed sequentially with water, saturated aqueous NaHCO$_3$, and water, then dried (MgSO$_4$), evaporated and purified by dry flash chromatography (0–50% EtOAc/CH$_2$Cl$_2$) to give methyl (E)-4-butyrylamino-1-methyl-2-pyrroleacrylate (45 mg. 75%) as cream plates, mp 109–110° C. $^1$H NMR (CDCl$_3$) δ 8.0–7.4 (br s, 1 H, NH), 7.51 (d, J=15.6 Hz, 1 H, H-β), 7.31 (d, J=1.8 Hz, 1 H, H-5), 6.39 (d, J=1.8 Hz, 1 H, H-3), 6.03 (d, J=15.6 Hz, 1 H, H-α), 3.72, 3.62 (2×s, 3 H each, CO$_2$CH$_3$, NCH$_3$), 2.27 (t, J=7.4 Hz, 2 H, CH$_2$CH$_2$CH$_3$), 1.71 (sextet, J=7.4 Hz, 2 H, CH$_2$CH$_2$CH$_3$), 0.96 (t, J=7.4 Hz, 3 H, CH$_2$CH$_2$CH$_3$); $^{13}$C NMR δ 170.3, 168.1 (NHCO, CO$_2$), 131.9, 118.5, 112.5, 102.0 (C-3, 5, α,β), 126.7, 123.5 (C-2,4), 51.5 (CO$_2$CH$_3$), 38.8 (NCH$_3$), 34.2 (CH$_2$CH$_2$CH$_3$), 19.1 (CH$_2$CH$_2$CH$_3$), 13.7 (CH$_2$CH$_2$CH$_3$).

Anal. Calculated for C13H$_{18}$N$_2$O$_3$: C, 62.4; H, 7.3; N, 11.1. Found: C, 62.1; H, 7.6; N, 11.0%.

A solution of the above ester (0.167 g, 0.667 mmol) and 0.2 M aqueous NaOH (5.7 mL, 1.13 mmol) in MeOH (10 mL) was heated under reflux for 50 min. The mixture was cooled in ice, acidified with 2 M aqueous HCl, and poured onto ice. The precipitate that formed was collected by filtration and washed with water to give (E)-4-butyrylamino-1-methyl-2-pyrroleacrylic acid as yellow needles (0.133 g, 85%) mp 74–76° C. (dec.) and 165–166° C. (with evolution of gas). $^1$H NMR [(CD$_3$)$_2$SO] δ 12.02 (br s, 1 H, CO$_2$H), 9.76 (br s, 1 H, CONH), 7.44 (d, J=15.6 Hz, 1 H, H-β), 7.27 (d, J=1.6 Hz, 1 H, H-5), 6.53 (d, J=1.6 Hz, 1 H, H-3), 6.02 (d, J=15.6 Hz, 1 H, H-α), 3.66 (s, 3 H, NCH$_3$), 2.19 (t, J=7.3 Hz, 2 H, CH$_2$CH$_2$CH$_3$), 1.57 (sextet, J=7.3 Hz, 2 H, CH$_2$CH$_2$CH$_3$), 0.88 (t, J=7.3 Hz, 3 H, CH$_2$CH$_2$CH$_3$),.; $^{13}$C NMR δ 169.2, 168.0 (NHCO, CO$_2$), 131.9, 117.8, 113.6, 101.9 (C-3,5,α,β), 125.8, 124.2 (C-2, 4), 37.5 (CH$_2$CH$_2$CH$_3$),, 33.6 (NCH$_3$), 18.7 (CH$_2$CH$_2$CH$_3$), 13.6 (CH$_2$CH$_2$CH$_3$). Anal. Calculated for C$_{12}$H$_{16}$N$_2$O$_4$: C, 61.0; H, 6.8; N, 11.9. Found: C, 61.2; H, 6.6; N, 11.9%.

Deprotection of 13 (300 mg, 0.83 mmol) as in Example C above and reaction with (E)-4-butyrylamino-1-methyl-2-pyrroleacrylic acid (197 mg, 0.83 mmol), EDCI.HCl (397 mg, 2.07 mmol) and DMA gave a product that was chromatographed on silica gel. Elution with CH$_2$Cl$_2$/EtOAc (1:1), followed by crystallisation from CH$_2$Cl$_2$/iPr$_2$O gave 14i (246 mg, 62%), mp 216° C. $^1$H NMR [(CD$_3$)$_2$SO] δ 9.79 (S, 1 H, NH), 9.22 (s, 1 H, H-4), 8.32 (d, J=8.7 Hz, 1 H, H-6), 8.17 (d, J=8.1 Hz, 1 H, H-9), 7.76–7.65 (m, 2 H, H-7,8), 7.64 (d, J=14.9 Hz, 1 H, COCH=CH), 7.25 (d, J=1.6 Hz, 1 H, H-5'), 6.81 (d, J=1.6 Hz, 1 H, H-3'), 6.71 (d, J=15.0 Hz, 1 H, COCH=CH), 4.65–4.50 (m, 3 H, H-1,2), 4.08 (d, J=3.6 Hz, 2 H, CH$_2$Cl), 3.71 (s, 3 H, NCH$_3$), 2.22 (t, J=7.3 Hz, 2 H, COCH$_2$), 1.60 (sextet, J=7.4 Hz, 2 H, CH$_2$CH$_3$), 0.90 (t, J=7.4 Hz, 3 H, CH$_2$CH$_3$). Anal. Calculated for C$_{25}$H$_{25}$ClN$_4$O$_4$: C, 62.4;H, 5.2; N, 11.7. Found: C, 62.6; H, 5.2; N, 11.5%.

EXAMPLE R

Preparation of 5-amino-1-[(E)-4-butyrylamino-1-methyl-2-pyrroleacryloyl]-1-(chloromethyl)-1,2-dihydro-3H-benz[e]indole (15i). A solution of 14i (100 mg, 0.21 mmol) in EtOAc (10 mL) was hydrogenated over EtOAc-washed Raney nickel (ca. 100 mg) at 40 psi for 3 h. The filtered solution was evaporated to dryness below 30° C., and the residue was chromatographed on silica gel to give a yellow oil which was crystallized from EtOAc/iPr$_2$O/petroleum ether to give 15i (9 mg, 10%); mp 245–250 (dec.). $^1$H NMR [(CD$_3$)$_2$SO] δ 9.76 (s, 1 H, NH), 8.04 (d, J=8.4 Hz, 1 H, H-6), 7.79 (v br s, 1 H, H-4), 7.71 (d, J=8.1 Hz, 1 H, H-9), 7.55 (d, J=15.0 Hz, 1 H, COCH=CH), 7.43 (t, J=9.3 Hz, 1 H, H-8), 7.28–7.20 (m, 2 H, H-7.5'), 6.75–6.65 (m, 2 H, COCH=CH, H-3'), 5.94 (br s, 2 H, NH$_2$), 4.47–4.34 (m, 1 H, H-2), 4.33 (dd, J=10.9, 2.1 Hz, 1 H, H-2), 4.13–4.04 (m, 1 H, H-1), 3.95 (dd, J=10.9, 3.0 Hz, 1 H, CHHCl), 3.73 (dd, J=11.0, 8.3 Hz, 1 H, CHHCl), 3.69 (s, 3 H, NCH$_3$), 2.21 (t, J=7.3 Hz, 2 H, COCH$_2$), 1.59 (sextet, J=7.3 Hz, 2 H, CH$_2$CH$_3$), 0.90 (t, J=7.4 Hz, 3 H, CH$_2$CH$_3$). Anal. Calculated for C$_{25}$H$_{27}$ClN$_4$O$_2$: C, 66.6 ; H, 6.0; N, 12.4. Found: C, 66.6, H, 6.0; N, 12.2%.

EXAMPLE S

Preparation of 3-[[5-[(5-acetylamino-1-methylpyrazol-3-yl)carboxamido]-1-methylpyrazol-3-yl]carbonyl]-1-(chloromethyl)-5-nitro-1,2-dihydro-3H-benz[e]indole (14j). A solution of methyl 5-[(5-benzyloxycarbonylamino-1-methylpyrazol-3-yl)carboxamido]-1-methylpyrazole-3-carboxylate [H. H. Lee et al., Anti-Cancer Drug Design, 6, 1991, 501–517] in MeOH was hydrogenated over 5% Pd-C at 55 psi for 2 h. Recrystallisation of the product from a small volume of EtOAc gave methyl 5-[(5-amino-1-methylpyrazol-3-yl)carboxamido]-1-methylpyrazole-3-carboxylate (93%), mp 167–168° C. $^1$H NMR [(CD$_3$)$_2$SO] δ 10.01 (s, 1 H, NH), 6.62 (s, 1 H, H-4), 5.77 (s, 1 H, H-4'), 5.49 (s, 2 H, NH$_2$), 3.78 (s, 3 H, CH$_3$), 3.74 (s, 3 H, CH$_3$), 3.64 (s, 3 H, CH$_3$). Anal. Calculated for C$_{11}$H$_{14}$N$_6$O$_3$: C, 47.5; H, 5.1; N, 30.2. Found: C, 47.8; H, 5.0; N, 30.1%.

The preceding amine (0.39 g, 1.40 mmol) was powdered and suspended in THF (20 mL) containing AcCl (2 mL). The mixture was heated at reflux with stirring for 30 min, then cooled and diluted with iPr$_2$O. The resulting solid was recrystallised from MeOH/EtOAc to give methyl 5-[(5-acetylamino-1-methylpyrazol-3-yl)carboxamido]-1-methylpyrazole-3-carboxylate (0.35 g, 78%), mp 215–216° C. $^1$H NMR [(CD$_3$)$_2$SO] δ 10.28 (s, 1 H, NH), 10.19 (s, 1 H, NH), 6.73 (s, 1 H, pyrazole H-4), 6.65 (s, 1 H, pyrazole H-4), 3.80 (s, 3 H, CH$_3$), 3.79 (s, 3 H, CH$_3$), 3.76 (s, 3 H, CH$_3$), 2.11 (s, 3 H, COCH$_3$). Anal. Calculated for C13H16N$_6$O$_4$: C, 48.7; H, 5.0; N, 26.2; Found: C, 48.9; H, 4.8; N, 26.1%.

A mixture of the preceding ester (0.38 g, 1.19 mmol and Cs$_2$CO$_3$ (3.26 g) in water (10 mL) was heated at reflux for 2 h, then concentrated, cooled to 0° C. and acidified with conc. HCl. After prolonged cooling, the crude product was collected and recrystallised from MeOH/EtOAc to give 5-[(5-acetylamino-1-methylpyrazol-3-yl)carboxamido]-1-methylpyrazole-3-carboxylic acid (0.19 g, 52%), mp 263–264° C. (dec.). $^1$H NMR [(CD$_3$)$_2$SO] δ 12.62 (s, 1 H, CO$_2$H), 10.24 (s, 1 H, NH), 10.18 (s, 1 H, NH), 6.72 (s, 1 H, pyrazole H-4), 6.59 (s, 1 H, pyrazole H-4), 3.80 (s, 3 H, NCH$_3$), 3.74 (s, 3 H, NCH$_3$), 2.11 (s, 3 H, COCH$_3$). Anal. Calculated for C12H14N$_6$O$_4$: C, 47.1; H, 4.6; N, 27.4. Found: C, 47.0; H, 4.5; N, 27.1%.

Deprotection of 13 (153 mg, 0.42 mmol) as in Example C above, and reaction with the preceding acid (135 mg, 0.44 mmol), EDCI.HCl (201 mg, 1.05 mmol) and DMA (2 mL) at 20° C. for 2.5 h, followed by addition of dilute KHCO$_3$, gave a solid that was collected, washed with water and dried. This solid was dissolved in THF (10 mL), and the solution was diluted with EtOAc (5 mL) and then filtered through a column of silica gel, elusting with further THF/EtOAc (2:1). The solution was concentrated under reduced pressure to a small volume and diluted with iPr$_2$O to precipitate a crude product that was twice recrystallised from THF/EtOAc/ iPr$_2$O to give 14j (125 mg, 54%), mp 158–160° C. $^1$H NMR [(CD$_3$)$_2$SO] δ 10.35 (s 1 H, NH), 10.20 (s, 1 H, NH), 9.19 (s, 1 H, H-4), 8.35 (dd, J=7.1, 2.7 Hz, 1 H, H-6), 8.21 (dd, J=6.8, 2.6 Hz, 1 H, H-9), 7.79–7.70 (m, 2 H, H-7,8), 6.78 (s, 1 H, pyrazole H-4), 6.75 (s, 1 H, pyrazole H-4), 4.92 (dd, J=11.9, 1.6 Hz, 1 H, H-2), 4.79 (dd, J=12.0, 9.4 Hz, 1 H, H-2), 4.59–4.50 (m, 1 H, H-1), 4.16–5.04 (m, 2 H, CH$_2$Cl), 3.84 (s, 3 H, NCH$_3$), 3.82 (s, 3 H, NCH$_3$), 2.12 (s, 3 H, CoCH$_3$). Anal. Calculated for C$_{25}$H$_{23}$ClN$_8$O$_5$: C, 54.5; H, 4.2; N, 20.3. Found: C, 54.2; H, 4.3; N, 19.9%.

EXAMPLE T

Preparation of 3-[[5-[(5-acetylamino-1-methylpyrazol-3-yl)carboxamido]-1-methylpyrazol-3-yl]carbonyl]-5-amino-1-(chloromethyl)-1,2-dihydro-3H-benz[e]indole (15j). A solution of 14j (77 mg, 0.14 mmol) in THF (50 mL) was hydrogenated over PtO$_2$ at 55 psi for 2.5 h. After removal of the catalyst, the solution was concentrated to a small volume under reduced pressure below 25° C. and diluted with iPr$_2$O to give 15j (63 mg, 87%) as an unstable solid, mp >250° C. $^1$H NMR [(CD$_3$)$_2$SO] δ 10.30 (s, 1 H, NH), 10.19 (s, 1 H, NH), 8.06 (d, J=8.5 Hz, 1 H, H-6), 7.75 (br s, 1 H, H-4), 7.73 (d, J=8.3 Hz, 1 H, H-9), 7.44 (t, J=7.5 Hz, 1 H, H-8), 7.27 (t, J=7.6 Hz, 1 H, H-7), 6.75 (s, 1 H, pyrazole H-4), 6.69 (s, 1 H, pyrazole H-4), 5.95 (s [associated smaller signal at 5.93], 2 H, NH$_2$;), 4.69 (d, J=11.5 Hz, 1 H, H-2), 4.56 (dd, J=11.9, 8.8 Hz, 1 H, H-2), 4.10–4.03 (m, 1 H, H-1), 3.94 (dd, J=10.9, 3.0 Hz, 1 H, CHHCl), 3.82 (s, 3 H, NCH$_3$), 3.80 (s, 3 H, NCH$_3$), 3.69 (dd, J=10.9, 8.3 Hz, 1 H, CHHCl), 2.12 (s, 3 H, COCH$_3$). Anal. Calculated for C$_{25}$H$_{25}$ClN$_8$O$_3$: C, 57.6; H, 4.8; N, 21.5; Cl, 6.8. Found: C, 5.75; H, 5.0; N, 21.3; Cl, 6.6%.

EXAMPLE U

Preparation of 3-[(E)-3-(acetylamino)cinnamoyl]-1-(chloromethyl)-5-nitro-1,2-dihydro-3H-benz[e]indole (14k). Deprotection of 13 (250 mg, 0.69 mmol) as in Example C above and reaction of the product with EDCI-.HCl (332 mg, 1.73 mmol), (E)-3-(acetylamino)cinnamic acid (148 mg, 0.72 mmol) and DMA (3 mL) at 20° C. for 3 h, followed by addition of dilute KHCO$_3$, precipitated. This was collected, dissolved in warm EtOAc (180 mL) and filtered through a column of silica gel. Solvent concentration followed by addition of i-Pr$_2$O precipitated the crude product which was recrystallised from EtOAc/i-Pr$_2$O to give 14k (232 mg, 75%), mp 214–216° C. $^1$H NMR [(CD$_3$)$_2$SO] δ 10.07 (s, 1 H, NH), 9.22 (s, 1 H, H-4), 8.33 (dd, J=7.8, 1.9 Hz, 1 H, H-6), 8.19 (dd, J=7.3, 1.6 Hz, 1 H, H-9), 7.88 (s, 1 H, H-2'), 7.78–7.63 (m, 3 H, H-7,8,4'), 7.68 (d, J=15.3 Hz, 1 H, PhCH=CH), 7.55 (d, J=7.8 Hz, 1 H, H-6'), 7.39 (t, J=7.9 Hz, 1 H, H-5'), 7.14 (d, J=15.4 Hz, 1 H, PhCH=CH), 4.72–4.55 (m, 3 H, H-1,2), 4.12–4.05 (m, 2 H, CH$_2$Cl), 2.08 (s, 3 H, CH$_3$). Anal. Calculated for C$_{24}$H$_{20}$ClN$_3$O$_4$: C, 64.1; H, 4.5; N, 9.2; Cl, 7.9. Found: C, 64.3; H, 4.4; N, 9.3; Cl, 7.8%.

EXAMPLE V

Preparation of 3-[(E)-3-(acetylamino)cinnamoyl]-5-amino-1-(chloromethyl)-1,2-dihydro-3H-benz[e]indole (15k). A solution of 13 (200 mg, 0.55 mmol) in THF (15 mL) was hydrogenated over PtO$_2$ at 55 psi for 1.5 h. The catalyst was removed, the solvent was evaporated, and the resulting solid was triturated with petroleum ether to give 5-amino-3-(tert-butyloxycarbonyl)-1-(chloromethyl)-1,2-dihydro-3H-benz[e]indole (166 mg, 90%), mp >200° C. $^1$H NMR [(CD$_3$)$_2$SO] δ 8.01 (d, J=8.4 Hz, 1 H, H-6), 7.64 (d, J=8.3 Hz, 1 H, H-9), 7.45–7.25 (underlying br s, 1 H, H-4), 7.40 (t, J=7.4 Hz, 1 H, H-8), 7.20 (t, J=7.4 Hz, 1 H, H-7), 7.91 (s, 2 H, NH$_2$), 4.11–3.87 (m, 4 H, H-1,2, CHHCl), 3.66 (dd, J=10.5, 8.3 Hz, 1 H, CHHCl), 1.53 (s, 9 H, C(CH$_3$)$_3$).

A solution of 9-fluorenylmethyl chloroformate (97%, 270 mg, 1.01 mmol) in dry CH$_2$Cl$_2$ (20 mL) was treated with 1-methylimidazole (90 mg, 1.10 mmol), followed by the above amine (270 mg, 0.84 mmol). The mixture was stirred at 20° C. for 1.5 h, then treated with additional 1-methylimidazole (18 mg, 0.22 mmol) and 9-fluorenylmethyl chloroformate (54 mg, 0.20 mmol). The mixture was stirred for a further 3 h and was then concentrated under reduced pressure, and the residue was chromatographed on silica gel. Elution with CH$_2$Cl$_2$/petroleum ether (9:1) gave a solid that was recrysallized from iPr$_2$O/ petroleum ether to give give 3-(tert-butyloxycarbonyl)-1-(chloromethyl)-5-(9-fluorenylmethyloxycarbonylamino)-1,2-dihydro-3H-benz[e]indole (417 mg, 89%), mp 103–106° C. $^1$H NMR [(CD$_3$)$_2$SO] δ 9.73 (s, 1 H, NHCO$_2$), 8.21 (br s, 1 H, H-4), 7.98 (d, J=8.5 Hz, 1 H, ArH), 7.95–7.85 (m, 3 H, ArH), 7.76 (br s, 2 H, ArH), 7.54 (t, J=7.5 Hz, 1 H, ArH), 7.48–7.27 (m, 5 H, ArH), 4.46 (d, J=7.0 Hz, 2 H, aliphatic H), 4.32 (t, J=6.8 Hz, 1 H, aliphatic H), 4.26–4.11 (m, 2 H, aliphatic H), 4.11–3.97 (m, 2 H, CHHCl, aliphatic H), 3.88 (dd, J=10.7, 6.9 Hz, 1 H, CHHCl), 1.52 (s, 9 H, C(CH$_3$)$_3$).

A solution of the above 5-NHFMOC compound (94 mg, 0.17 mmol) in HCl-saturated dioxane (6 mL) was stirred at 20° C. for 2 h, then evaporated to dryness under reduced pressure below 30° C. EDCI.HCl (81 mg, 0.42 mmol), (E)-3-(acetylamino)cinnamic acid (37 mg, 0.18 mmol) and DMA (2 mL) were then added and the mixture was stirred at 20° C. for 4 h. Addition of dilute KHCO$_3$ precipitated a yellow solid which was collected, dried and dissolved in EtOAc. Addition of petroleum ether precipitated impurities that were removed by filtration. The solution was then concentrated to small volume and diluted with iPr$_2$O to give 3-[(E)-3-(acetylamino)cinnamoyl]-1-(chloromethyl)-5-(9-fluorenylmethyloxycarbonylamino)-1,2-dihydro-3H-benz [e]indole (47 mg, 43%), mp 208–209° C. $^1$H NMR [(CD$_3$)$_2$SO] δ 10.06 (s, 1 H, NHCO), 9.75 (s, 1 H, NHCO$_2$), 8.65 (s, 1 H, H-4), 7.01–7.87 (m, 4 H, ArH), 7.85 (s, 1 H, H-2'), 7.77 (br s, 2 H, ArH), 7.69–7.30 (m, 9 H, ArH), 7.62 (d, J=15.5 Hz, 1 H, PhCH=CH), 7.14 (d, J=15.4 Hz, 1 H, PhCH=CH), 4.65–4.27 (m, 6 H, aliphatic H), 4.06 (dd, J=11.1, 3.0 Hz, 1 H, CHHCl), 3.96 (dd, J=11.0, 7.2 Hz, 1 H, CHHCl), 2.07 (s, 3 H, CH$_3$).

A solution of the above compound (31 mg, 0.048 mmol) in dry DMF (0.4 mL) was treated at 20° C. with piperidine (0.04 mL). After 20 min the mixture was poured into water and the precipitated solid was collected, dried and dissolved in EtOAc. The solution was filtered through a short column of silica gel, and the eluates were concentrated to small volume and diluted with iPr$_2$. The resulting solid was recrystallised from EtOAc/iPr$_2$O/petroleum ether to give 15k (17 mg, 84%), mp >250° C. $^1$H NMR [(CD$_3$)$_2$SO] δ 10.06 (s, 1 H, NH), 8.06 (d, J=8.5 Hz, 1 H, H-6), 7.86 (s, 1 H, H-2'), 7.83 (br s, 1 H, H-4), 7.72 (d, J=8.3 Hz, 1 H, H-9), 7.65 (d, J=8.0 Hz, 1 H, H-4'), 7.59 (d, J=15.3 Hz, 1 H, PhCH=CH), 7.50 (d, J=7.6 Hz, 1 H, H-6'), 7.44 (d, J=7.6 Hz, 1 H, H-8), 7.38 (t, J=7.9 Hz, 1 H, H-5'), 7.26 (d, J=7.7 Hz, 1 H, H-7), 7.11 (dd, J=15.4 Hz, 1 H, PhCH=CH), 5.97 (s, 2 H, NH$_2$), 4.54–4.42 (m, 1 H, H-1), 4.39 (d, J=9.5 Hz, 1 H, NH$_2$), 4.18–0.07 (m, 1 H, H-1), 3.96 (dd, J=10.9, 2.9 Hz, 1 H, CHHCl), 2.75 (dd, J=10.9, 8.3 Hz, 1 H, CHHCl), 2.07 (s, 3 H, CH$_3$). Anal. Calculated for C$_{24}$H$_{22}$ClN$_3$O$_2$: C, 68.6; H, 5.3; N, 10.0; Cl, 8.4. Found: C, 68.4; H, 5.4; N, 10.0; Cl, 8.1%.

EXAMPLE W

Preparation of 1-(chloromethyl)-3-[(E)-3-methoxycinnamoyl]-5-nitro-1,2-dihydro-3H-benz[e]indole (14l). Deprotection of 13 (250 mg, 0.69 mmol) as in Example C above, and reaction of the product with EDCl.HCl (331 mg, 1.73 mmol), (E)-3-methoxycinnamic acid (129 mg, 0.72 mmol) and DMA (3 mL) at 20° C. for 3 h, followed by addition of dilute KHCO$_3$, gave a solid. This was recrystallised from CH$_2$Cl$_2$/i-Pr$_2$O followed by EtOAc to give 14l (215 mg, 74%), mp 200° C. $^1$H NMR [(CD$_3$)$_2$SO] δ 9.22 (s, 1 H, H-4), 8.33 (dd, J=7.9, 1.8 Hz, 1 H, H-6), 8.19 (dd, J=7.5, 1.7 Hz, 1 H, H-9), 7.78–7.68 (m, 2 H, H-7,8), 7.72 (d, J=15.4 Hz, 1 H, PhCH=CH), 7.45–7.34 (m, 2 H, H-5',6'), 7.39 (s, 1 H, H-2'), 7.26 (d, J=15.4 Hz, 1 H, PhCH=CH), 7.02 (dt, J=7.2, 2.2 Hz), 1 H, H-4'), 4.71–4.56 (m, 3 H, H-1,2), 4.11–4.05 (m, 2 H, CH$_2$Cl), 3.84 (s, 3 H, CH$_3$). Anal. Calculated for C$_{23}$H$_{19}$ClN$_2$O$_4$: C, 65.3; H, 4.5; N, 6.6; Cl, 8.4. Found: C, 65.0; H, 4.6; N, 6.6; Cl, 8.5%.

EXAMPLE X

Preparation of 5-amino-1-(chloromethyl)-3-[(E)-3-methoxycinnamoyl]-1,2-dihydro-3H-benz[e]indole (15l). To a hot solution of 14l (110 mg, 0.26 mmol) in THF (10 mL) was added in sequential fashion MeOH (5 mL), H$_2$O (2 mL), AcOH (0.2 mL) and Fe powder (0.5 mL). The mixture was heated at reflux for 1 h, then basified with CaO (1 g), filtered, concentrated to a small volume under reduced pressure below 30° C. and diluted with water. The resulting precipitate was chromatographed on silica gel, eluting with CH$_2$Cl$_2$/EtOAc (9:1), to give a solid which was recrystallised from CH$_2$Cl$_2$/petroleum ether to give 15l (55 mg, 54%) mp >200° C. $^1$H NMR [(CD$_3$)$_2$SO] δ 8.06 (d, J=8.5 Hz, 1 H, H-6), 7.83 (bs, 1 H, H-4), 7.72 (d, J=8.3 Hz, 1 H, H-9), 7.63 (d, J=15.4 Hz, 1 H, PhC=CH), 7.44 (t, J=7.4 Hz, 1 H, H-8), 7.40–7.34 (m, 3 H, PhH), 7.26 (t, partially obscured, J=7.9 Hz, 1 , H-7), 7.22 (d, J=15.4 Hz, 1 h, PhCH=CH), 7.04–6.97 (m, 1 H, PhH), 5.95 (br s, 2 H, NH$_2$), 4.53–4.38 (m, 2 H, H-2), 4.19–4.08 (m, 1 H, H-1), 3.95 (dd, J=11.0, 2.9 Hz, 1 H, CHHCl), 3.83 (s, 3 H, OCH$_3$), 3.76 (dd, J=10.9, 8.1 Hz, 1 H, CHHCl). Anal. Calculated for C$_{23}$H$_{21}$ClN$_2$O$_2$: C, 70.3; H, 5.4; N, 7.1; Cl, 9.0. Found: C, 70.4; H, 5.6; N, 6.9; Cl, 9.1%.

EXAMPLE Y

Preparation of 3-[(E)-4-(acetylamino)cinnamoyl]-5-amino-1-(chloromethyl)-1,2-dihydro-3H-benz[e]indole (15m). Deprotection of 13 (302 mg, 0.83 mmol) as in Example C above and evaporation of the reaction to dryness under reduced pressure gave a solid that was dissolved in pyridine (5 mL). The stirred solution was treated dropwise at 0° C. with trifluoroacetic anhydride (0.14 mL, 0.99 mmol). The mixture was stirred for a further 10 min at 20° C., then poured into water and the precipitated solid was dissolved in CH$_2$Cl$_2$ and filtered through a column of silica gel. The solvent was removed under reduced pressure and the residue was crystallised from EtOAc/petroleum ether to give 1-(chloromethyl)-5-nitro-3-trifluoroacetyl-1,2dihydro-3H-benz[e]indole (241 mg, 81%), mp 182° C. $^1$H NMR (CDCl$_3$) δ 9.10 (s, 1 H, H-4), 8.49–8.43 (m, 1 H, H-6), 7.93–7.87 (m, 1 H, H-9), 7.76–7.68 (m, 2 H, H-7,8), 4.70 (dt, J=11.4, 1.4 Hz, 1 H, H-2), 4.51 (dd, J=11.5, 8.6 Hz, 1 H, H-2), 4.35–4.28 (m, 1 H, H-1), 3.97 (dd, J=11.7, 3.4 Hz, 1 H, CHHCl), 3.64 (dd, J=11.7, 8.8 Hz, 1 H, CHHCl). Anal. Calculated for C$_{15}$H$_{10}$ClF$_3$N$_2$O$_3$: C, 50.2; H, 2.8; N, 7.8; Cl, 9.9. Found: C, 50.1; H, 2.8; N, 7.8; Cl, 9.9%.

A solution of the above nitro compound (175 mg, 0.49 mmol) in benzene (30 mL) was hydrogenated over PtO$_2$ (45 mg) at 50 psi for 1 h. Removal of the catalyst and solvent provided a solid which was recrystallised from i-Pr$_2$O/petroleum ether to give 5-amino-1-(chloromethyl)-3-trifluoroacetyl-1,2-dihydro-3H-benz[e]indole (143 mg, 89%), mp 177° C. $^1$H NMR [(CD$_3$)$_2$SO] δ 8.11 (d, J=8.4 Hz, 1 H, H-6), 7.80 (d, J=8.3 Hz, 1 H, H-9), 7.60 (s, 1 H, H-4), 7.50 (t, J=7.7 Hz, 1 H, H-8), 7.35 (t, J=7.7 Hz, 1 H, H-7), 6.14 (s, 2 H, NH$_2$), 4.45 (dd, J=11.0, 8.7 Hz, 1 H, H-2), 4.33 (d, J 11.2 Hz, 1 H, H-2), 4.24–4.16 (m, 1 H, H-1), 4.03 (dd, J=11.0, 3.0 Hz, 1 H, CHHCl), 3.84 (dd, J=11.0, 7.1 Hz, 1 H, CHHCl). Anal. Calculated for C$_{15}$H$_{12}$ClF$_3$N$_2$O: C, 54.8; H, 3.7; N, 8.5; Cl, 10.8. Found: C, 55.1; H, 3.4; N, 8.6; Cl, 10.7%.

A mixture of the above 5-amino compound (200 mg, 0.61 mmol) and di-tert-butyl dicarbonate (266 mg, 1.22 mmol) in dioxane (20 mL) was stirred at 65° C. under N$_2$ with the exclusion of light for 4 h. Additional di-tert-butyl dicarbonate (200 mg, 0.92 mmol) was added and the mixture was stirred for a further 8 h at 70° C. and then concentrated under reduced pressure. The residue was chromatographed on silica gel, eluting with petroleum ether/CH$_2$Cl$_2$ (1:3), to provide a solid which was recrystallised from i-Pr$_2$O/petroleum ether to give 5-(tert)butyloxycarbonylamino)-1-(chloromethyl)-3-trifluoroacetyl-1,2-dihydro-3H-benz[e]indole (192 mg, 74%), mp 185° C. $^1$H NMR [(CD$_3$)$_2$SO] δ 9.41 (s, 1 H, HN), 8.48 (s, 1 H, H-4), 8.10 (d, J=8.4 Hz, 1 H, H-6), 8.01 (d, J=8.2 Hz, 1 H, H-9), 7.61 (t, J=7.1 Hz, 1 H, H-8), 7.52 (t, J=7.7 Hz, 1 H, H-7), 4.56 (dd, J=11.1, 9.7 Hz, 1 H, H-2), 4.47–4.37 (m, 2 H, H-1,2), 4.12 (dd, J=11.1, 2.8 Hz, 1 H, CHHCl), 4.01 (dd, J=11.2, 5.8 Hz, 1 H, CHHCl), 1.50 (s, 9 H, C(CH$_3$)3). Anal. Calculated for C$_{20}$H$_{20}$ClF3N$_2$O$_3$: C, 56.0; H, 4.7; N, 6.5; Cl, 8.3. Found: C, 56.3; H, 4.6; N, 6.6; Cl, 8.0%.

A stirred solution of the above trifluoroacetate (180 mg, 0.42 mmol) in N-methylpyrrolidone (4.5 mL) was treated dropwise at 20° C. with a solution of Cs$_2$CO$_3$ (1.2 g) in water (2.7 mL). The mixture was stirred for a further 45 min at 20° C. then diluted with water (35 mL) and extracted with benzene (2×25 mL). The combined organic extracts were washed with water (2×), dried (Na$_2$SO$_4$) and concentrated under reduced pressure below 30° C. The residue was treated sequentially with EDCI.HCl (201 mg, 1.05 mmol), (E)-4-(acetylamino)cinnamic acid (86 mg, 0.42 mmol), DMA (2 mL) and DMA.HCl (52 mg, 0.42 mmol). The mixture was stirred for a further 30 min at 20° C., diluted with KHCO$_3$ solution. The precipitated solid was collected, washed with water, dried and dissolved in warm EtOAc. This solution was filtered through a short column of silica gel, then concentrated to a small volume and diluted with i-Pr$_2$O/petroleum ether to give 3-[(E)-4-(acetylamino) cinnamoyl]-5-(tert-butyloxycarbonylamino)-1-(chloromethyl)-1,2-dihydro-3H-benz[3]indole (97 mg, 44%), mp 200° C. $^1$H NMR [(CD$_3$)$_2$SO] δ 10.15 (br s, 1 H, NHCO), 9.28 (br s, 1 H, NHCO$_2$), 8.64 (br s, 1 H, H-4), 8.02 (d, J=8.1 Hz, 1 H, H-6), 7.92 (d, J=8.3 Hz, 1 H, H-9), 7.76 (d, J=8.6 Hz, 2 H, H-3',5'), 7.67 (d, J=9.1 Hz, 2 H, H-2',6'), 7.64 (d, J=15.6 Hz, 1 H, PhCH=CH), 7.55 (t, J=7.3 Hz, 1 H, H-8), 7.43 (t, J=7.5 Hz, 1 H, H-7), 7.13 (br d, J=15.3 Hz, 1 H, PhCH=CH), 4.60–4.45 (m, 2 H, H-2), 4.35 (br s, 1 H, H-1), 4.02 (dd, J=11.1, 3.0 Hz, 1 H, CHHCl), 3.92 (dd, J=11.1, 7.2 Hz, 1 H, CHHCl), 2.08 (s, 3 H, OCH$_3$). 1.51 (s, 9 H, C(CH$_3$)$_3$).

A cold suspension of the preceding compound (83 mg, 0.16 mmol) in dioxane (8 mL) was saturated with HCl gas and left at 20° C. for 10 min. The mixture was diluted with EtOAc/petroleum ether and the product was collected and partitioned between dilute KHCO$_3$ and EtOAc. The organic layer was washed with water, dried (Na$_2$SO$_4$) and filtered through a short column of silica gel. The solution was concentrated to small volume under reduced pressure below 30° C. and then diluted with petroleum ether to give 15m (54 mg, 81%), mp >250° C. $^1$H NMR [(CD$_3$)$_2$SO] δ 10.14 (s, 1 H, NH), 8.05 (d, J=8.5 Hz, 1 H, H-6), 7.83 (br s, 1 H, H-4), 7.74 (d, J=8.8 Hz, 2 H, H-3',5'), 7.72 (d, J=9.1 Hz, 1 H, H-9), 7.66 (d, J=8.5 Hz, 2 H, H-2',6'), 7.60 (d, J=15.3 Hz, 1 H, PhCH=CH), 7.44 (t, J=7.5 Hz, 1 H, H-8), 7.26 (t, J=7.6 Hz, 1 H, H-8), 7.10 (d, J=15.3 Hz, 1 H, PhCH=CH), 5.97 (br s, 2 H, NH$_2$), 4.50–4.35 (m, 2 H, H-2), 4.12 (br s, 1 H, H-1), 3.95 (dd, J=10.9, 2.6 Hz), 1 H, CHHCl), 3.74 (dd, J=10.6, 8.5 Hz, 1 H, CHHCl), 2.07 (s, 3 H, OCH$_3$). Anal. Calculated for C$_{24}$H$_{22}$ClN$_3$O$_2$: C, 68.6; H, 5.3; N, 10.1; Cl, 8.5. Found: C, 68.5; H, 5.4; N, 9.9; Cl, 8.2%.

EXAMPLE Z

Preparation of 5-amino-1-(chlorometyl)-3-[(E)-4-methoxycinnamoyl]-1,2-dihydro-3H-benz[e]indole (15n). A stirred solution of the above 5-(tert-butyloxycarbonylamino)-1-(chloromethyl)-3-trifluoroacetyl-1,2-dihydro-3H-benz[e]indole (100 mg, 0.23 mmol) in N-methylpyrrolidone (2.5 mL) was treated dropwise at 20° C. with a solution of Cs$_2$CO$_3$ (650 mg) in water (1.5 mL). the mixture was stirred for a further 45 min at 20° C. then diluted with water (20 mL) and extracted with benzene (2×15 mL). The combined organic extracts were washed with water (2×), dried (Na$_2$SO$_4$) and concentrated under reduced pressure below 30° C. The residue was dissolved in pyridine (2 mL), cooled to −5° C. and treated with (E)-4-methoxycinnamoyl chloride (46 mg, 0.23 mmol) followed by DMAP (15 mg). The mixture was stirred for a further 30 min at 20° C., then diluted with KHCO$_3$ solution. The precipitated solid was collected, washed with water, dried and chromatographed on silica gel. Elution with CH$_2$Cl$_2$/EtOAc gave the crude product which was recrystallised from CH$_2$Cl$_2$/petroleum either to give 5-(tert-butyloxycarbonylamino)-1-(chloromethyl)-3-[(E)-4-methoxycinnamoyl]-1,2-dihydro-3H-benz[e]indole (55 mg, 48%), mp 185–185.5° C. $^1$H NMR [(CD$_3$)$_2$SO] δ 9.28 (br s, 1 H, NH), 8.64 (br s, 1 H, H-4), 8.01 (d, J=8.1 Hz, 1 H, H-6), 7.92 (d, J=8.3 Hz, 1 H, H-9), 7.78 (d, J=8.6 Hz, 2 H, H-2',6'), 7.66 (d, J=15.3 Hz, 1 H, PhCH=CH), 7.54 (t, J=7.6 Hz, 1 H, H-8), 7.42 (t, J=7.7 Hz, 1 H, H-7), 7.10 (d, J=15.2 Hz, 1 H, PhCH=CH), 7.01 (d, J=8.7 Hz, 2 H, H-3',5'), 4.60–4.44 (m, 2 H, H-2), 4.41–4.28 (m, 1 H, H-1), 4.02 (dd, J=11.1, 3.0 Hz, 1 H, CHHCl), 3.92 (dd, J=11.1, 7.2 Hz, 1 H, CHHCl), 3.82 (s, 3 H, OCH$_3$), 1.51 (s, 9 H, C(CH$_3$)$_3$).

A cold suspension of the preceding compound (46 mg, 0.09 mmol) in dioxane (5 mL) was saturated with HCl gas and left at 20° C. for 10 min. The mixture was diluted with EtOAc/petroleum ether and the product was collected and partitioned between dilute KHCO$_3$ and EtOAc. The organic layer was washed with water, dried (Na$_2$SO$_4$), concentrated under reduced pressure below 30° C. and the residue chromatographed on silica gel. Elution with CH$_2$Cl$_2$/EtOAc (2:1) gave a solid which was recrystallised from CH$_2$Cl$_2$/petroleum ether to give 15n (26 mg, 71%), mp 114–116° C. $^1$H NMR [(CD$_3$)$_2$SO] δ 8.05 (d, J=8.4 Hz, 1 H, H-6), 7.82 (br s, 1 H, H-4), 7.76 (d, J=8.7 Hz, 2 H, H-2',6'), 7.71 (d, J=8.3 Hz, 1 H, H-9), 7.62 (d, J=15.3 Hz, 1 H, PhCH=CH), 7.44 (t, J=7.5 Hz, 1 H, H-8), 7.01 (d, J=8.7 Hz, 2 H, H-3',5'), 5.96 (br s, 2 H, NH$_2$), 4.49–4.36 (m, 2 H, H-2), 4.17–4.06 (m, 1 H, H-1), 3.94 (dd, J=11.0, 2.9 Hz, 1 H, CHHCl), 3.82 (s, 3 H, OCH$_3$), 3.74 (dd, J=10.9, 8.3 Hz, 1 H, CHHCl). Anal. Calculated for C$_{23}$H$_{21}$ClN$_2$O$_2$: C, 70.3; H, 5.4; N, 7.1; Cl, 9.0. Found: C, 70.6; H, 5.5; N, 6.9; Cl; 8.7%

EXAMPLE AA

Preparation of 1-[(methanesulfonyloxy)methyl]-5-nitro-3-[(5,6,7-trimethoxyindol-2-yl)carbonyl]-1,2-dihydro-3H-benz[e]indole (14o). A stirred solution of 3-(tert-butyloxycarbonyl)-1-(hydroxymethyl)-5-nitro-1,2-dihydro-3H-benz[e]indole (12) (450 mg, 1.31 mmol) in pyridine (1.3 mL) was treated dropwise at −5° C. with methanesulfonyl chloride (0.121 mL, 1.57 mmol) and then stirred at 20° C. for 2 h. The mixture was diluted with water then cooled and the resulting solid collected, washed with water and dried. This product was dissolved in CH$_2$Cl$_2$ and the solution was filtered through a short column of silica gel, eluting with further CH$_2$Cl$_2$. The resulting product was triturated with iPr$_2$O/petroleum ether to give 3-(tert-butyloxycarbonyl)-1-[(methanesulfonyloxy)methyl]-5-nitro-1,2-dihydro-3H-benz[e]indole (494 mg, 89%), mp 147° C. (dec.). $^1$H NMR [(CD$_3$)$_2$SO] δ 8.75 (br s, 1 H, H-4), 8.32 (d, J=8.5 Hz, 1 H, H-6), 8.12 (d, J=8.2 Hz, 1 H, H-9), 7.77–7.63 (m, 2 H, H-7, 8), 4.54 (dd, J=10.0, 3.7 Hz, 1 H, H-2), 4.43 (dd, J=10.0, 6.4 Hz, 1 H, H-2), 4.42–4.33 (m, 1 H, H-1), 4.25 (t, J=10.3 Hz, 1 H, CHHO), 4.14 (dd, J=11.4, 2.5 Hz, 1 H, CHHO), 3.11 (s, 3 H, SO$_2$CH$_3$), 1.56 (s, 9 H, C(CH$_3$)$_3$). Anal. Calculated for C19H$_{22}$N$_2$O$_7$S: C, 54.0; H, 5.3; N, 6.6; S, 7.6. Found: C, 54.3; H, 5.4; N, 6.9; S, 7.4%.

A solution of the preceding compound (265 mg, 0.63 mmol), was stirred in HCl-saturated dioxane (12 mL) at 20° C. for 2 h, then evaporated to dryness under reduced pressure below 30° C. 5,6,7-Trimethoxyindole-2-carboxylic acid (165 mg, 0.66 mmol), EDCI.HCl (301 mg, 1.57 mmol) and DMA (2.5 mL) were added and the mixture was stirred at 20° C. for 2.5 h. Addition of dilute KHCO$_3$ precipitated a solid which was collected, washed well with water and chromatographed on silica gel. elution with CH$_3$Cl$_2$/EtOAc (4:1) provided a crude product which was recrystallised from EtOAc/petroleum ether to give 14o (264 mg, 76%), mp 213.5–214.5° C. $^1$H NMR [(CD$_3$)$_2$SO] δ 11.61 (d, J=1.6 Hz, 1 H, NH), 9.11 (s, 1 H, H-4), 8.36 (d, J=8.7 Hz, 1 H, H-6), 8.21 (d, J=7.6 Hz, 1 H, H-9), 7.82–7.71 (m, 2 H, H-7,8), 7.17 (d, J=2.0 Hz, 1 H, H-3'), 6.98 (s, 1 H, H-4'), 4.88 (t, J=9.8 Hz, 1 H, H-2), 4.66–4.46 (m, 4 H, H-1,2, CH$_2$O), 3.94 (s, 3 H, OCH$_3$), 3.83 (s, 3 H, OCH$_3$), 3.81 (s, 3 H, OCH$_3$), 3.06 (s, 3 H, SO$_2$CH$_3$). Anal. Calculated for C$_{26}$H$_{25}$N$_3$O$_9$S: C, 56.2; H, 4.5; N, 7.6. Found: C, 56.2; H, 4.5; N, 7.7%.

EXAMPLE BB

Preparation of 5-amino-1-[(methanesulfonyloxy)methyl]-3-[(5,6,7-trimethoxyindol-2-yl)carbonyl]-1,2-dihydro-3H- benz[e]indole (15o). A solution of 14o (162 mg, 0.29 mmol) in THF (15 mL) was hydrogenated over PtO$_2$ at 55 psi for 2 h. After removal of the catalyst, the solution was concentrated to a small volume under reduced pressure below 25° C. and diluted with iPr$_2$O to give a crude product. This was purified by precipitation from an EtOAc solution with petroleum ether at 20° C. to give 5-amino-1-[(methanesulfonyloxy)methyl]-3-[(5,6,7-trimethoxyindol-2-yl)carbonyl]-1,2-dihydro-3H-benz[e]indole (15o) (116 mg, 76%) as an unstable solid, mp >260° C. $^1$H NMR [(CD$_3$)$_2$SO] δ 11.41 (d, J=1.6 Hz, 1 H, NH), 8.08 (d, J=8.5 Hz, 1 H, H-6), 7.76 (d, J=8.3 Hz, 1 H, H-9), 7.67 (s, 1 H, H-4), 7.49 (t, J=7.6 Hz, 1 H, H-8), 7.30 (t, J=7.6 Hz, 1 H, H-7), 7.04 (d, J=2.0 Hz, 1 H, H-3'), 6.96 (s, 1 H, H-4'), 6.15 (v br s, 2 H, NH$_2$), 4.66 (dd, J=10.9, 8.5 Hz, 1 H, H-2), 4.47 (dd, J=9.9, 3.4 Hz, 1 H, H-2), 4.41 (d, J=10.9 Hz, 1 , CHHO), 4.17 (t, J=9.2 Hz, 1 H, CHHO), 4.13–4.04 (m, 1 H, H-1), 3.94 (s, 3 H, OCH$_3$), 3.82 (s, 3 H, OCH$_3$), 3.80 (s, 3 H, OCH$_3$), 3.07 (s, 3 H, SO$_2$CH$_3$). Anal. Calculated for C$_{26}$H$_{27}$N$_3$O$_7$S: C, 59.4; H, 5.2; N, 8.0. Found: C, 59.3; H, 5.4; N, 8.1%.

EXAMPLE CC

Preparation of (R)- and (S)-1-(chloromethyl)-5-nitro-3-[(5,6,7-trimethoxyindol-2-yl)carbonyl]-1,2-dihydro-3H-benz[e]indole (14aR and 14aS). (R,S)-3-(tert-Butyloxycarbonyl)-1[(methanesulfonyloxy)methyl]-5-nitro-1,2-dihydro-3H-benz[e]indole [for preparation see Example AA] was resolved by HPLC on a Diacel Chiralcel OD semi-preparative column (10 (m, 2×25 cm), loading 15 mg samples in acetonitrile/iPrOH/hexane (25:37.5:37.5) and running in iPrOH/hexane (50:50) at a flow rate of 6.75 mL/min. This gave baseline separation of the enantiomers (α value of ca. 1.45), with the R enantiomer ([α]D −60°; c 0.31, THF( having an RT of 30 min and the S enantiomer ([α]D +61°; c 0.31, THF) an RT of 42 min. The absolute configurations of the enantiomers were determined by an X-ray crystal structure of the R enantiomer. Conversion of these enantiomers as above gave (R)-1-(chloromethyl)-3[(5,6,7-trimethoxyindol-2-yl)carbonyl]-1,2-dihydro-3H-benz[e]indole (14aR): ([α]D −55°; c 0.23, THF); and (S)-1-(chloromethyl)-3-[(5,6,7-trimethoxyindol-2-yl)carbonyl]-1,2-dihydro-3H-benz[e]indole (14aS): ([α]D +54°; c 0.23, THF).

EXAMPLE DD

Preparation of (R)- and (S)-5-amino-1-(chloromethyl)-3-[(5,6,7-trimethoxyindol-2-yl)carbonyl]-1,2-dihydro-3H-benz[e]indole (15aR and 15aS). Reduction of 14aR and 14aS as above gave, respectively, (R)-5-amino-1-(chloromethyl)-3-[(5,6,7-trimethoxyindol-2-yl)carbonyl]-1,2-dihydro-3H-benz[e]indole (15aR): ([α]D-10°; c 0.20, THF); and (S)-5-amino-1-(chloromethyl)-3-[(5,6,7-trimethoxyindol-2-yl)carbonyl]-1,2-dihydro-3H-benz[e]indole (15aS): ([α]D +10°; c 0.20, THF).

EXAMPLE EE

Preparation of 1-(chloromethyl)-5-methylamino-3-[(5,6,7-trimethoxyindol-2-yl)carbonyl]-1,2-dihydro-3H-benz[e]indole (15p). Acetic-formic anhydride [60 μL of a solution prepared from formic acid (1.25 mL, 33 mmol) and acetic anhydride (2.5 mL, 27 mmol)] was added to a solution of 15a (206 mg, 0.44 mmol) in THF (20 mL) at 0° C. under N$_2$. After stirring for 30 min at 0° C., additional acetic-formic anhydride (60 μL) was added to the heterogeneous mixture, and stirring was continued for 2.5 h at 0° C. The mixture was then evaporated to dryness under very low pressure. The residue was suspended in THF (35 mL), treated with BH$_3$.DMS (0.15 mL, 1.5 mmol), then stirred under reflux for 45 min. The reaction was cooled, MeOH (2 mL) followed by 2 N HCl (10 mL) were added, and the mixture was stirred at 20° C. for 15 min. Volatiles were removed under reduced pressure, and the residue was shaken with aqueous KHCO$_3$ and extracted with EtOAc (2×). The combined extracts were washed with water, dried, and concentrated under reduced pressure. Chromatography of the residue on silica gel, eluting with CH$_2$Cl$_2$/EtOAc (5:1), followed by precipitation from an EtOAc solution with iPr$_2$O at 20° C., gave 15p (89 mg, 42%), mp 122–125° C. $^1$H NMR [(CD$_3$)$_2$SO] δ 11.45 (d, J=1.4 Hz, 1 H, indole NH), 8.09 (d, J=8.5 Hz, 1 H, H-6), 7.78 (d, J=8.1 Hz, 1 H, H-9), 7.48 (t, J=7.6 Hz, 1 H, H-8), 7.32 (t, J=7.6 Hz, 1 H, H-7), ca. 7.3 (underlying s, 1 H, H-4), 7.04 (d, J=1.8 Hz, 1 H, H-3'), 6.97 (s, 1 H, H-4'), 6.53 (q, J=4.6 Hz, 1 H, NHCH$_3$), 4.67 (t, J=9.9 Hz, 1 H, H-2), 4.46 (dd, J=11.0, 1.5 Hz, 1 H, H-2), 4.17–4.07 (m, 1 H, H-1), 3.98 (dd, J=11.0, 3.0 Hz, 1 H, CHHCl), 3.92 (s, 3 H, OCH$_3$), 3.82 (s, 3 H, OCH$_3$), 3.80 (s, 3 H, OCH$_3$), 3.77 (dd, J=11.0, 8.2 Hz, 1 H, CHHCl), 2.80 (br s, 3 H, NHCH$_3$). Anal. Calculated for C$_{26}$H$_{26}$ClN$_3$O$_4$: C, 65.1; H, 5.5; N, 8.8; Cl, 7.4. Found: C, 65.3; H, 5.6; N, 8.5; Cl, 7.1%.

EXAMPLE FF

Preparation of 1-(chloromethyl)-5-dimethylamino-3-[(5,6,7-trimethoxy-indol-2-yl)carbonyl]-1,2-dihydro-3H-benz [e]indole (15q). A mixture of 15a (181 mg, 0.39 mmol) and formaldehyde (0.30 mL of ca. 40% w/v, 4 mmol) in THF (5 mL) was treated with solid NaB$_3$CN (63 mg, 1.0 mmol), followed by 2 N HCl (0.7 mL). The mixture was stirred at 20° C. for 2 h, then diluted with water and extracted with CH$_2$Cl$_2$ (3×). The combined extracts were washed with water, dried, and concentrated under reduced pressure, and the residue was chromatographed on silica gel. Elution with CH$_2$Cl$_2$/EtOAc (4:1) gave a gum which was triturated with etOAc/iPr$_2$O, and the resulting crude product was purified by precipitation from a CH$_2$Cl$_2$ solution with iPr$_2$O at 20° C. to give 15q (130 mg, 68%), mp 174–175° C. $^1$H NMR [(CD$_3$)$_2$SO] δ 11.48 (d, J=1.6 Hz, 1 H, NH), 8.14 (d, J=8.3 Hz, 1 H, H-6), ca. 8.0 (underlying br s, 1 H, H-4), 7.92 (d, J=8.2 Hz, 1 H, H-9), 7.54 (t, J=7.5 Hz, 1 H, H-8), 7.44 (t, J=7.6 Hz, 1 H, H-7), 7.07 (d, J=1.8 Hz, 1 H, H-3'), 6.98 (s, 1 H, H-4'), 4.73 (t, J=9.9 Hz, 1 H, H-2), 4.51 (dd, J=11.1, 1.8 Hz, 1 H, H-2), 4.30–4.20 (m, 1 H, H-1), 4.05 (dd, J=11.1, 3.1 Hz, 1 H, CHHCl), 3.93 (s, 3 H, OCH$_3$), 3.88 (dd, J=11.1, 7.6 Hz, 1 H, CHHCl), 3.82 (s, 3 H, OCH$_3$), 3.80 (s, 3 H, OCH$_3$), 2.50 (s, 6 H, N(CH$_3$)$_2$). Anal. Calculated for C$_{27}$H$_{28}$ClN$_3$O$_4$: C, 65.7; H, 5.8; N, 8.5; Cl, 7.2. Found: C, 65.7; H, 6.0; N, 8.6; Cl, 7.1%.

EXAMPLE GG

Preparation of 1-(chloromethyl)-5-[(4-nitrobenzyloxycarbonyl)amino]-3-[(5,6,7-trimethoxyindol-2-yl)carbonyl]-1,2-dihydro-3H-benz[e]indole (15r). A solution of 15a (430 mg, 0.92 mmol) in THF (50 mL) was treated portionwise at −5° C. with solid 4-nitrobenzyl chloroformate (298 mg, 1.38 mmol). The mixture was stirred at 10° C. for 30 min and then at 20° C. for 2 h, before being diluted with iPr$_2$O/petroleum ether. The precipitate was collected and extracted with CH$_2$Cl$_2$ at 20° C. and the filtered solution was evaporated to give a residue which was chromatographed on silica gel. Elution with CH$_2$Cl$_2$/EtOAc (9:1) provided an eluate which was concentrated under reduced pressure until the appearance of a solid. Addition of iPr$_2$O completed precipitation of the crude product, which was then recrystallised from $CH_2Cl_2/iPr_2O$ to give 15r (290 mg, 49%), mp 191–192° C. $^1$H NMR [$(CD_3)_2SO$] δ 11.48 (d, J=1.7 Hz, 1 H, indole NH), 9.91 (s, 1 H, $NHCO_2$), 8.57 (br s, 1 H, H-4), 8.39 (d, J=8.7 Hz, 2 H, H-3",5"), 8.09 (d, J=8.5 Hz, 1 H-6), 7.99 (d, J=8.3 Hz, 1 H, H-9), 7.73 (d, J=8.5 Hz, 2 H, H-2",6"), 7.58 (t, J=7.6 Hz, 1 H, H-8), 7.48 (t, J=7.7 Hz, 1 H, H-7), 7.10 (d, J=2.2 Hz, 1 H, H-3'), 6.98 (s, 1 H, H-4'), 5.36 (s, 2 H, $COh_2CH_2$), 4.80 (dd, J=10.8, 9.4 Hz, 1 H, H-2), 4.53 (dd, J=11.1, 1.9 Hz, 1 H, H-2), 4.39–4.31 (m, 1 H, H-1), 4.07 (dd, J=11.1, 3.1 Hz, 1 H, CHHCl), 3.97–3.91 (m, 1 H, CHHCl), 3.94 (s, 3 H, $OCH_3$), 3.82 (s, 3 H, $OCH_3$), 3.80 (s, 3 H, $OCH_3$). Anal. Calculated for $C_{33}H_{29}ClN_4O_8$: C, 61.4%; H, 4.5; N, 8.7; Cl, 9.5. Found: C, 61.1; H, 4.4; N, 8.6; Cl, 5.5%

EXAMPLE HH

Preparation of N-[1-(chloromethyl)-3-[(5,6,7-trimethoxyindol-2-yl)carbonyl]-1,2-dihydro-3H-benz[e]indol-5-yl]-2-methyl-2-(2-nitrophenyl)propanamide (15s). A stirred mixture of 2-methyl-2-(2-nitrophenyl)propanoic acid [Atwell et al., J. Med. Chem. 37, 1994, 371–380] (29 mg, 0.14 mmol) and $SOCl_2$ (2 mL) containing a trace of DMF was warmed for 30 min, then evaporated to dryness under a high vacuum. The residue was cooled to −10° C. and treated in one portion with an ice-cold solution of 15a (64 mg, 0.14 mmol) in dry pyridine (0.8 mL). The reaction mixture was stirred at 20° C. for 4 h then diluted with aqueous $KHCO_3$, and the resulting precipitate was collected and chromatographed on silica gel. Elution with $CH_2Cl_2$/EtOAc (9:1) gave a product which was twice recrystallised from $CH_2Cl_2/iPr_2O$ to give 15s (16 mg, 18%), mp 139–143° C. $^1$H NMR [$(CD_3)_2SO$] δ 11.52 (d, J=1.6 Hz, 1 H, indole NH), 9.54 (s, 1 H, NHCO), 8.35 (br s, 1 H, H-4), 7.98 (d, J=8.3 Hz, 1 H, H-6), 7.92 (d, J=8.4 Hz, 1 H, H-9), 7.90–7.80 (m, 2 H, 2×PhH), 7.74 (t, J=7.7 Hz, 1 H, PhH), 7.60–7.50 (m, 2 H, H-8, PhH), 7.46 (t, J=7.7 Hz, 1 H, H-7), 7.10 (d, J=2.0 Hz, 1 H, H-3'), 6.98 (s, 1 H, H-4'), 4.81 (t, J=10.1 Hz, 1 H, H-2), 4.54 (dd, J=11.1, 1.8 Hz, 1 H, H-2), 4.42–4.33 (m, 1 H, H-1), 4.08 (dd, J=11.1, 3.1 Hz, CHHCl), 3.99–3.91 (m, partially obscured, 1 H, CHHCl), 3.93 (s, 3 H, $OCH_3$), 3.82 (s, 3 H, $OCH_3$), 3.80 (s, 3 H, $OCH_3$), 1.84 (s, 3 H, $CCH_3$), ), 1.83 (s, 3 H, $CCH_3$). HRMS(FAB). Calculated for $C_{36}H_{33}ClN_4O_7$ (M+H+): 657.2116, 659.2087. Found: 657.2093, 659.2069.

EXAMPLE II

Preparation of 2-(S)-[N-[1-(S,R)-(chloromethyl)-3-[(5,6,7-trimethoxyindol-2-yl)carbonyl]-1,2-dihydro-3H-benz[e]indol-5-yl]ureylene]pentanedioate (15t). A solution of di-t-butyl (S)-2-isocyanatopentanedioate (0.19 g, 0.66 mmol) [prepared by the method of J. S. Nowick et al, J. Org. Chem., 57, 1992, 7364–7366], 15a (154 mg, 0.33 mmol), and dibutyltin diacetate (1 drop) in 1,2-dichloroethane (20 mL) was stirred at 20° C. More isocyanate (4×0.19 g) was added after 2, 5, 7, and 9 days. After 12 days ethanolamine (0.21 g, 3.4 mmol) was added, and after a further 30 min the solvent was evaporated. The residue was purified by chromatography (30% EtOAc-petroleum ether then 20% EtOAc-$CHCl_3$) to give di-t-butyl 2-(S)-[N-[1-(S,R)-(chloromethyl)-3-[(5,6,7-trimethoxyindol-2-yl)carbonyl]-1,2-dihydro-3H-benz[e]indol-5-yl]ureylene]pentanedioate as a light tan film (155 mg, 62%). $^1$H NMR [$(CD_3)_2SO$] δ 11.46 (s, 1 H, NH), 8.91 (s, 1 H, NH or H-4), 8.73 (s, 1 H, NH or H-4), 8.10 (d, J=8.6 Hz, 1 H, H-6 or 9), 7.94 (d, J=8.3 Hz, 1 H, H-6 or 9), 7.57 (t, J=7.4 Hz, 1 H, H-7 or 8), 7.48 (t, J=7.7 Hz, 1 H, H-7 or 8), 7.08 (d, J=2.1 Hz, 1 H, H-3'), 6.97 (s, 1 H, H-4'), 6.93 (dd, J=7.6, 1.2 Hz, 1 H, NH), 4.77 (t, J=10 Hz, 1 H, H-2), 4.50 (dd, J=11.0, 1.7 Hz, 1 H, H-2), 4.31–4.25 (m, 1 H, H-1), 4.24–4.17 (m, 1 H, $NCHCO_2tBu$), 4.04 (dd, J=11.2, 3.2 Hz, 1 H, $CH_2Cl$), 3.94 (s, 3 H, $OCH_3$), 3.87 (dd, J=11.0, 7.3 Hz, 1 H, $CH_2Cl$), 3.82 (s, 3 H, $OCH_3$), 3.80 (s, 3 H, $OCH_3$), 2.41–2.23 (m, 2 H, $CH_2CH_2CO_2tBu$), 2.04–1.94 (m, 1 H, $CH_2CH_2CO_2tBu$), 1.88–1.79 (m, 1 H, $CH_2CH_2CO_2tBu$), 1.45, 1.43 (2×s, 9 H, $CO_2tBu$), 1.41, 1.40 (2 (s, 9 H, $CO_2tBu$). MS (FAB, $^{35}Cl$) m/z 750 (M+, 25%), 639 (20%), 234 (100%). HRMS Calculated for $C_{39}H_{47}ClN_4O_9$ 750.3031. Found 750.3038.

The above di-t-butyl ester (149 mg, 0.20 mmol) was stirred in HCl-saturated dioxane (8 mL) at 20° C. for 4 h, monitoring the reaction by HPLC. The solvent was evaporated and the residue separated by HPLC ($CH_3CN$-formate buffer). The fraction containing the diacid was evaporated and the residue was diluted with water and extracted with EtOAc. The extracts were dried ($Na_2SO_4$) and evaporated to give 15t as a yellow foam (58 mg, 46%). $^1$H NMR [$(CD_3)_2SO$] δ 12.4 (v br s, 2 H, $CO_2H$), 11.47 (s, 1 H, NH), 8.95 (d, J=2.8 Hz, 1 H, NH), 8.76 (s, 1 H, H-4), 8.11 (d, J=8.6 Hz, 1 H, H-6 or 9), 7.94 (d, J=8.3 Hz, 1 H, H-6 or 9), 7.58 (t, J=7.7 Hz, 1 H, H-7 or 8), 7.48 (t, J=7.6 Hz, 1 H, H-7 or 8), 7.09 (d, J=2.1 Hz, 1 H, H-3'), 7.00–6.95 (m, 2 H, H-4' and NH), 4.77 (t, J=10.0 Hz, 1 H, H-2), 4.50 (dd, J=11.0, 1.7 Hz, 1 H, H-2), 4.31–4.24 (m, 2 H, H-1 and $NCHCO_2H$), 4.04 (dd, J=11.0, 3.0 Hz, 1 H, $CH_2Cl$), 3.94 (s, 3 H, $OCH_3$), 3.87 (dd, J=11.1, 7.2 Hz, 1 H, $CH_2Cl$), 3.82 (s, 3 H, $OCH_3$), 3.80 (s, 3 H, $OCH_3$), 2.43–2.27 (m, 2 H, $CH_2CH_2CO_2H$), 2.10–2.01 (m, 1 H, $CH_2CH_2CO_2H$), 1.91–1.81 (m, 1 H, $CH_2CH_2CO_2H$). HRMS (FAB, $^{35}Cl$) Calculated for $C_{31}H_{31}ClN_3O_9$ 639.1858. Found 639.1852.

EXAMPLE JJ

Preparation of methyl 1-(chloromethyl)-5-nitro-3-[(5,6,7-trimethoxyindol-2-yl)carbonyl]-1,2-dihydro-3H-pyrrolo[3,2-e]indole-7-carboxylate (31) (Scheme 4). Borane-dimethylsulfide (34 mL, 0.34 mmol) was added to a solution of 2-iodo-3-nitrobenzoic acid (43) [P. J. Culhane, Org. Synth. Coll. Vol 1, 1967, 125–127] (82.3 g, 0.28 mol) and trimethyl borate (64 mL, 0.56 mol) in dry THF (400 mL) under nitrogen, and the mixture stirred at reflux for 90 min. The solution was cooled, MeOH then $H_2O$ were added, and the mixture was evaporated. Aq NaCl was added to the residue and the mixture was extracted with EtOAc (×3). The extracts were washed with aq NaCl, dried ($Na_2SO_4$), and evaporated to give crude 2-iodo-3-nitrobenzyl alcohol (44) as a yellow-orange solid suitable for use in the next step. A sample was filtered through a short column of silica eluting with $CH_2Cl_2$ and recrystallized from PhH as pale yellow needles, mp 91–91.5° C. $^1$H NMR ($CDCl_3$) δ 7.72 (dd, J=7.7, 1.1 Hz, 1 H, H-4 or 6), 7.59 (dd, J=8.1, 1.5 Hz, 1 H, H-4 or 6), 7.50 (t, J=7.8 Hz, 1 H, H-5), 4.78 (s, 2 H, $CH_2$), 2.14 (br s, 1 H, OH). Anal. Calculated for $C_7H_6INO_3$: C, 30.1; H, 2.2; N, 5.0. Found: C, 30.4; H, 2.1; N, 4.9%.

Acetic anhydride (37 mL, 0.39 mol) was added to a solution of 44, triethylamine (59 mL, 0.42 mol) and DMAP (0.25 g, 2 mmol) in $CH_2Cl_2$ (400 mL) at 0° C. The ice-bath was removed and the yellow solution was stirred for 10 min, then evaporated. The residue was dissolved in EtOAc, washed with aq HCl (2 N, ×2), aq $NaHCO_3$ (×2), dried ($Na_2SO_4$), and evaporated. The resulting orange oil crystallized from MeOH—$H_2O$ to give 2-iodo-3-nitrogenzyl acetate (45) as a pale yellow solid (7.58 g, 84% for two steps), mp 65–65° C. $^1$H NMR ($CDCl_3$) δ 7.60 (dd, J=7.9, 1.7 Hz, 1 H, H-4 or 6), 7.57 (dd, J=7.9, 1.7 Hz, 1 H, H-4 or 6), 7.48 (t, J=7.8 Hz, 1 H, H-5), 5.22 (s, 2 H, CH$_2$), 2.18 (s, 3 H, CH$_3$). Anal. Calculated for C$_9$H$_8$INO$_4$: C, 33.7; H, 2.5; N, 4.4. Found: C, 33.9; H, 2.4; N, 4.3%.

A solution of 45 (8.00 g, 24.9 mmol) in EtOH (100 mL) and H$_2$O (100 mL) at reflux was treated with AcOH (20 mL). Fe powder (5.57 g, 97 mmol) was washed with HCl (2 N) then H$_2$O and added to the hot solution. The mixture was stirred vigorously at reflux for a further 15 min, then cooled to 20° C. Conc. NH$_3$ (40 mL) was added and the mixture was filtered through Celite, eluting with EtOAc. The EtOH was evaporated, and the residue was diluted with aq NaCl and extracted with EtOAc (×2). The extracts were dried (Na$_2$SO$_4$) and evaporated and the resulting solid was recrystallized from MeOH to give 3-amino-2-iodobenzyl acetate (46) as a cream powder (3.72 g, 51%), mp 80–81° C. The mother liquor was evaporated and the residue purified by chromatography (30% EtOAc-petroleum ether) to give more product (2.93 g, 40%). $^1$H NMR (CDCl$_3$) δ 7.12 (t, J=7.7 Hz, 1 H, H-5), 6.76 (dd, J=7.2, 1.3 Hz, 1 H, H-4 or 6), 6.72 (dd, J=7.9, 1.4 Hz, 1 H, H-4 or 6), 5.11 (s, 2 H, CH$_2$), 4.24 (br s, 2 H, NH$_2$), 2.14 (s, 3 H, CH$_3$). Anal. Calculated for C$_9$H$_{10}$INO$_2$: C, 37.1; H, 3.5; N, 4.8. Found: C, 37.4; H, 3.4; N, 4.8%.

A solution of 46 (26.9 g, 92 mmol) and di-t-butyldicarbonate (40.3 g, 184 mmol) in dioxane (200 mL) was stirred at reflux for 2 days. The solution was evaporated and the residue separated by chromatography (10–20% EtOAc-petroleum ether) to give recovered starting material (13.2 g, 49%) and 3-(t-butyloxycarbonyl)amino-2-iodobenzyl acetate (47) as a pale yellow oil (17.5 g, 48%). A sample crystallized from petroleum ether as a white solid, mp 62–63° C. $^1$H NMR (CDCl$_3$) δ 8.00 (dd, J=8.2, 1.0 Hz, 1 H, H-4 or 6), 7.31 (t, J =7.9 Hz, 1 H, H-5), 7.08 (dd, J=7.7, 1.4 Hz, 1 H, H-4 or 6), 6.99 (br s, 1 H, NH), 5.14 (s 2 H, CH$_2$), 2.15 (s, 3 H, COCH$_3$), 1.53 (s, 9 H, t-Bu). Anal. Calculated for C$_{14}$H$_{18}$INO$_4$: C, 43.0; H, 4.6; N, 3.6. Found: C, 43.3; H, 4.7; N, 3.8%.

Sodium hydride (4.48 g of a 60% dispersion in oil, 113 mmol) was washed with petroleum ether (×3) and suspended in DMF (80 mL) under nitrogen at 0° C. A solution of 47 (29.2 g, 75 mmol) and allyl bromide (19.4 mL, 225 mmol) in DMF (100 mL) was added in a single portion. After 5 min the mixture was allowed to warm to 20° C. and stirred for a further 1 h. H$_2$O was added and the DMF was evaporated. The residue was diluted with H$_2$O, extracted with CH$_2$Cl$_2$ (×3), and the extracts were dried (Na$_2$SO$_4$) and evaporated. This gave crude 3-[N-(t-butyloxycarbonyl)-N-(2-propenyl)] amino-2-iodobenzyl acetate 48) as a colourless oil, suitable for use in the next step. $^1$NMR (CDCl$_3$) δ 7.36–7.24 (m, 2 H), 7.19 (br d, J=7.1 Hz, ca. 0.4 H, H-4 or 6 minor rotamer), 7.08 (br d, J=7.1 Hz, ca. 0.6 H, H-4 or 6 major rotamer), 6.00–5.90 (m, 1 H, CH=CH$_2$), 5.18 (s, 2 H, CH$_2$OAc), 5.24–5.05 (m, 2 H, CH=CH$_2$), 4.59–4.43 (m, 1 H, CH$_2$CH=CH$_2$), 3.75–3.58 (m, 1 H, CH$_2$CH=CH$_2$), 2.16 (s, 3 H, COCH$_3$), 1.53 (s, ca. 3 H, t-Bu minor rotamer), 1.34 (s, ca. 6 H, t-Bu major rotamer); MS (CI, NH$_3$) m/z 449 (10%, M+NH$_4$), 432 (3%, M+H), 393 (100%, M-C$_4$H$_8$+NH$_4$), 376 (30%, M-C$_4$H$_8$+H); HRMS Calculated for C$_{17}$H$_{23}$INO$_4$ 432.0672. Found 432.0665.

Crude 48 was dissolved in MeOH (400 mL) and a solution of K2CO$_3$ (12.4 g, 90 mmol) in H$_2$O (80 mL) was added. The mixture was stirred at 20° C. for 15 min and the MeOH was evaporated. The aqueous residue was extracted with EtOAc (×2), and the extracts were dried (Na$_2$SO$_4$) and evaporated to give crude 3-[N-(t-butyloxycarbonyl)-N-(2-propenyl)]amino-2-iodobenzyl alcohol (49) as a pale yellow oil, suitable for use in the next step. A sample crystallized from petroleum ether as white prisms, mp 91.5–92.5° C. $^1$H NMR (CDCl$_3$) δ7.39–7.29 (m, 2 H), 7.16 (br d, J=6.3 Hz, ca. 0.4 H, H-4 or 6 minor rotamer), 7.06 (br d, J=7.2 Hz, ca. 0.6 H, H-4 or 6 major rotamer), 6.00–5.89 (m, 1 H, CH=CH$_2$), 5.14–5.03 (m, 2 H, CH=CH$_2$), 4.74–4.68 (m, 2 H, CH$_2$OH), 4.57–4.42 (m, 1 H, CH$_2$CH=CH$_2$), 3.74–3.59 (m, 1 H, CH$_2$CH=CH$_2$), 2.12 (br s, 1 H, OH), 1.53 (s, ca. 3 H, t-Bu minor rotamer), 1.34 (s, ca. 6 H, t-Bu major rotamer). Anal. Calculated for C$_{15}$H$_{20}$INO$_3$: C, 46.3; H, 5.2; N, 3.6. Found: C, 46.5; H, 5.4; N, 3.6%.

Crude 49 was dissolved in EtOAc (300 mL), MNO$_2$ (40 g, 0.46 mol) was added, and the mixture was stirred at reflux for 20 h. The mixture was filtered through Celite eluting with EtOAc, more MNO$_2$ (40 g, 0.46 mol) was added, and the mixture was stirred at reflux for a further 6 h. The filtration and oxidation was repeated once more with fresh MNO$_2$ (40 g, 0.46 mol), and after a further 6 h at reflux TLC (25% EtOAc-petroleum ether) indicated that the oxidation was complete. The mixture was filtered through Celite eluting with EtOAc, and the filtrate was evaporated to give 3-[N-(t-butyloxycarbonyl)-N-(2-propenyl)]amino-2-iodobenzaldehyde (50) as a pale yellow oil (25.3 g, 88% for three steps). $^1$NMR (CDCl$_3$) δ 10.17 (s, 1 H, CHO), 7.80–7.75 (m, 1 H), 7.49–7.34 (m, 2 H), 6.01–5.89 (m, 1 H, CH=CH$_2$), 5.18–5.03 (m, 2 H, CH=CH$_2$), 4.62–4.46 (m, 1 H, CH$_2$CH=CH$_2$), 3.77–3.64 (m, 1 H, CH$_2$CH=CH$_2$), 1.55 (s, ca. 4 h, t-Bu minor rotamer), 1.34 (s, ca. 5 H, t-Bu major rotamer); MS (CI, NH$_3$) m/z 405 (4%, M+NH$_4$), 388 (4%, M+H), 349 (100%, M-C$_4$H$_8$+NH$_4$), 332 (40%, M-C$_4$H$_8$+H); HRMS Calculated for C$_{15}$H$_{19}$INO$_3$ 388.0410. Found 388.0399.

Sodium bis(trimethylsilyl)amide (38.4 mL of a 2M solution in THF, 77 mmol) was added dropwise over 45 min to a solution of 50 (7.43 g, 19.2 mmol) and methyl azidoacetate (11.0 g, 96 mmol) in THF (80 mL) under nitrogen at −78° C. The brown solution was stirred at this temperature for 1 h then poured into H$_2$O (300 mL) containing aq HCl (2N, 43 mL). The mixture was extracted with EtOAc (×2) and the extracts were dried (Na$_2$SO$_4$) and evaporated. Chromatography (10–20% EtOAc-petroleum ether) gave recovered starting material (0.83 g, 11%) and crude azidoalcohol (51) as a pale yellow foam (6.18 g, 64%). Cruce 51 (6.34 g, 12.6 mmol) was dissolved in CH$_2$Cl$_2$ (50 mL) at 0° C. and triethylamine (4.40 mL, 32 mmol) and methanesulfonyl chloride (1.2 mL, 15 mmol) were added. The mixture was stirred at 0° C. for 30 min, then diluted with H$_2$O and extracted with CH$_2$Cl$_2$ (×2). The extracts were dried (Na$_2$SO$_4$) and evaporated and the residue purified by chromatography (8% EtOAc-petroleum ether) to give crude azidocinnamte (52) as a pale yellow oil (5.11 g, 84%).

A solution of crude 52 (5.11 g, 10.6 mmol) in xylene (80 mL) was added dropwise over 40 min to xylene (70 mL) at reflux under nitrogen. The solution was stirred at reflux for a further 10 min then evaporated. Chromatography (20% EtOAc-petroleum ether) gave methyl 5-[N-(t-butyloxycarbonyl)-N-(2-propenyl)]amino-4-iodoindole-2-carboxylate (53) as a cream solid (4.09 g, 85%, 46% overall from the benzaldehyde), mp 178–179° C. (MeOH). $^1$NMR (CDCl$_3$) δ 9.32 (br s, 1 H, NH), 7.35–7.04 (m, 3 H), 6.03–5.92 (m, 1 H, CH=CH$_2$), 5.13–5.02 (m, 2 H, CH=CH$_2$), 4.58–4.46 (m, 1 H, CH$_2$CH=CH$_2$), 3.97 (s, 3 H, CO$_2$Me), 3.90 (dd, J=14.6, 5.9 Hz, ca. 0.7 H, CH$_2$CH=CH$_2$ major rotamer), 3.75 (dd, J=15.5, 6.5 Hz, ca. 0.3 H, CH$_2$CH=CH$_2$ minor rotamer), 1.56 (s, ca. 3 H, t-Bu minor rotamer), 1.33 (s, ca. 6 H, t-Bu major rotamer). Anal. Calculated for C$_{18}$H$_{21}$IN$_2$O$_4$: C, 47.4; H, 4.6; N, 6.1. Found: C, 47.3; H, 4.8; N, 6.3%.

A solution of tributyltin hydride (13.8 mL), 51 mmol) in toluene (150 mL) was added dropwise over 3 h to a solution of 53 (5.86 g, 12.8 mmol) and Tempo (2,2,6,6-tetramethylpiperidinyloxy, 10.0 g, 64 mmol) in toluene (400 mL) under nitrogen at 70–80° C., during which time the red Tempo colour faded to pale yellow. TLC analysis (30% EtOAc-petroleum ether) showed some unreacted starting material. More Tempo (3.0 g, 19 mmol) was added in a single portion, followed by a solution of tributyltin hydride (3.5 mL, 13 mmol) in toluene (80 mL) added dropwise over 2 h. The mixture was cooled and evaporated. Chromatography ($CHCl_3$ then 5–20% EtOAc-petroleum ether) gave a pink solid (ca. 10 g) which was recrystallized from MeOH to give methyl 3-(t-butyloxycarbonyl)-1-[(2,2,6,6-tetramethylpiperidino)oxy]methyl-1,2-dihydro-3H-pyrrolo[3,2-e]indole-7-carboxylate (54) as a white solid (3.65 g, 59%), mp 191.5–193° C. The mother liquor was evaporated and purified by chromatography (5–20% EtOAc-petroleum ether) followed by recrystallization (MeOH) to give a second crop (1.12 g, 18%). $^1$H NMR ($CDCl_3$) δ 8.84 (s, 1 H, NH), 8.05 (br, s, ca. 0.7 H, H-4 major rotamer), 7.63 (br, s, ca. ).3 H, H-4 minor rotamer), 7.26 (d, J=8.8 Hz, 1 H, H-5), 7.13 (s, 1 H, H-8), 4.20–4.05 (m, 3 H), 3.94 (s, 3 H, $CO_2Me$), 3.91–3.74 (m, 2 H), 1.58 (br s, 9 H, t-Bu), 1.48–1.27 (m, 6 H, $CH_2CH_2CH_2$), 1.21 (s, 3 H, $CH_3$), 1.11 (s, 3 H, $CH_3$), 1.08 (s, 3 H, $CH_3$), 1.06 (s, 3 H, $CH_3$); $^{13}$C NMR (one peak not observed) δ 162.2, 152.7, 137.2, 134.0, 127.9, 124,4, 114.5, 110.9, 106.3, 80.1, 78.4, 59.9, 52.2, 52.0, 39.7, 33.1, 28.5, 20.2, 17.1. Anal. Calculated for $C_{27}H_{39}N_3O_5$: C, 66.8; H, 8.1; N. 8.7. Found: C, 66.8; H, 8.2; N, 8.7%.

Zinc powder (7.39 g, 113 mmol) was added to a solution of 54 (6.86 g, 14.1 mmol) in THF (150 mL), HOAc (150 mL), and $H_2O$ (50 mL). The mixture was stirred at reflux for 40 min, cooled, and filtered through Celite eluting with EtOAc. The filtrate was evaporated and the residue diluted with $H_2O$ and extracted with EtOAc (×2). The extracts were washed with $H_2O$, aq $NaHCO_3$, and dried ($Na_2SO_4$) and evaporated. Recrystallization from MeOH gave methyl 3-(t-butyloxycarbonyl)-1-hydroxymethyl-1,2-dihydro-3H-pyrrolo[3,2-e]indole-7-carboxylate (55) as a white solid (3.86 g, 79%), mp 189.5–191° C. (dec.). The mother liquor was purified by chromatography (40% EtOAc-petroleum ether) to give more alcohol (0.74 g, 15%). $^1$H NMR [($CD_3$)$_2$SO] δ 11.88 (s, 1 H, NH), 7.87 (v br s, 1 H, H-4), 7.29 (d, J=8.9 Hz, 1 H, H-5), 7.11 (d, J=1.4 Hz, 1 H , H-8), 4.95 (t, J=5.2 Hz, 1 H, OH), 4.03 (t, J=10.5 Hz, 1 H), 3.92–3.86 (m, 1 H), 3.87 (s, 3 H, $CO_2Me$), 3.82–3.75 (m, 1 H), 3.67 (br s, 1 H), 3.55–3.48 (m, 1 H), 1.51 (s, 9 H, t-Bu); $^{13}$C NMR δ 161.6, 151.8, 136.2, 134.6, 127.8, 123.7, 122.6, 113.3, 113.3, 111.3, 105.5, 79.3, 63.1, 51.7, 51.2, 42.2, 28.1. Anal. Calculated for $C18H_{22}N2O_5$: C, 62.4; H, 6.4; N, 8.1. Found: C, 62.3; H, 6.6; N, 8.3%.

A warm solution of 55 (447 mg, 1.29 mmol) in $CH_3NO_2$ (50 mL) was cooled in an ice bath. As the starting material began to precipitate (internal temperature ca. 5° C.) c.$HNO_3$ (0.16 mL, 2.6 mmol) was added dropwise, giving an orange-red mixture. The suspension was stirred at 0° C. for 40 min, then poured into cold $H_2O$ and extracted with $CH_2Cl_2$ (×3). The extracts were washed with aq. $NaHCO_3$, dried ($Na_2SO_4$), and evaporated. The residue was recrystallized from MeOH to give methyl 3-(t-butyloxycarbonyl)-1-hydroxymethyl-5-nitro-1,2-dihydro-3H-pyrrolo[3,2-e]indole-7-carboxylate (29) as an orange powder (229 mg, 45%), mp 200° C. (dec.). The mother liquor was purified by chromatography (40% EtOAc-petroleum ether) to give more 29 (70 mg, 14%). $^1$H NMR [($CD_3$)$_2$SO] δ 11.22 (d, J=1.5 Hz, 1 H, NH), 8.72 (br, s, ca. 0.8 H, H-4 major rotamer), 8.42 (br s, ca. 0.2 H, H-4 minor rotamer), 7.47 (d, J=2.0 Hz, 1 H, H-8), 5.02 (t, J=5.2 Hz, 1 H, OH), 4.14 (t, J=10.5 Hz, 1 H), 3.95 (dd, J=11.2, 4.7 Hz, 1 H), 3.92 (s, 3 H, $CO_2Me$), 3.89–3.80 (m, 1 H), 3.73 (t, J=5.2 Hz, 2 H), 1.54 (s, 9 H, t-Bu). Anal. Calculated for $C18H_{21}N_3O_7$: C, 55.2; H, 5.4; N, 10.7. Found: C, 55.4; H, 5.4; N, 10.7%.

A solution of 29 (1.52 g, 3.87 mmol) in HCl-saturated dioxane (120 mL) was stirred for 100 min (until TLC indicated complete reaction) and the suspension was evaporated. EDCI.HCl (1.48 g, 7.74 mmol) and 5,6,7-trimethoxyindole-2-carboxylic acid (0.97 g, 3.87 mmol) in DMA (12 mL) were added, and the mixture stirred at 20° C. for 16 h. Dilute aq $NaHCO_3$ (100 mL) was added, and the precipitated solid was filtered off, washed with $H_2O$, and dried. Trituration with hot MeOH gave methyl 1-hydroxymethyl-5-nitro-3-[(5,6,7-trimethoxyindol-2-yl)carbonyl]-1,2-dihydro-3H-pyrrolo[3,2-e]indole-7-carboxylate (56) as an orange powder (1.45 g, 71%), mp 239–240.5° C. (dec.). $^1$H NMR [($CD_3$)$_2$SO] δ 11.46 (d, J=32 1.6 Hz, 1 H, NH), 11.30 (s, 1 H, NH), 9.19 (s, 1 H, H-4), 7.54 (s, 1 H, H-8), 7.09 (s, 1 H, H-3'), 6.95 (s, 1 H, H-4'), 5.11 (t, J=5.3 Hz, 1 H, OH), 4.71 (t, J=10.1 Hz, 1 H, H-2), 4.47 (dd, J=10.6, 4.1 Hz, 1 H, H-2), 4.02–3.95 (m, 1 H), 3.94 (s, 3 H, OMe), 3.93 (s, 3 H, OMe), 3.82 (s, 3 H, OMe), 3.80 (s, 3 H, OMe), 3.81–3.75 (m, 2 H). Anal. Calculated for $C_{25}H_{24}N_4O_9 \cdot \frac{1}{2}H_2O$: C, 56.3; H, 4.7; N, 10.5. Found: C, 56.4; H, 4.4; N, 10.3%.

Dichlorotriphenylphosphorane (1.65 g, 5.1 mmol) was added to a solution of 56 (1.34 g, 2.55 mmol) in pyridine (75 mL) and the solution stirred at 20° C. After 10 min more dichlorotriphenylphosphorane (2.06 g, 6.4 mmol) was added, and after a further 10 min the solution was poured into $H_2O$ and the mixture stirred for 5 min. The precipitated solid was filtered off, washed with $H_2O$, and redissolved in $CH_2Cl_2$ (400 mL). This solution was filtered through Celite, eluting with $CH_2Cl_2$, and the filtrate was dried ($Na_2SO_4$) and evaporated. The resulting orange solid was recrystallized from $CH_2Cl_2$ giving methyl 1-(chloromethyl)-5-nitro-3-[(5,6,7-trimethoxyindol-2-yl)carbonyl]-1,2-dihydro-3H-pyrrolo[3,2-e]indole-7-carboxylate (31) as an orange powder (0.88 g, 64%), mp 246–247.5° C. The mother liquor was evaporated onto silica and purified by chromatography (50% EtOAc-petroleum ether) to give further 31 (0.50 g, 36%). $^1$H NMR ($CDCl_3$) δ 10.39 (s, 1 H, NH), 9.42 (s, 1 H, NH), 9.39 (s, 1 H, H-4), 7.31 (d, J=2.2 Hz, 1 H, H-8), 6.97 (d, J=2.4 Hz, 1 H, H-3'), 6.86 (s, 1 H, H-4'), 4.80 (t, J=10.0 Hz, 1 H, H-2), 4.69 (dd, J=10.8, 4.4 Hz, 1 H, H-2), 4.32–42.3 (m, 1 H, H-1). 4.09 (s, 3 H, OMe), 4.05 (dd, J=11.4, 3.9 Hz, 1 H, $CH_2Cl$), 4.02 (s, 3 H, OMe), 3.95 (s, 3 H, OMe), 3.91 (s, 3 H, OMe), 3.77 (dd, J=11.4, 8.8 Hz, 1 H, $CH_2Cl$); $^{13}$C NMR [($CD_3$)$_2$SO] δ 160.5, 160.0, 149.2, 140.0, 139.0, 137.5, 133.6, 132.1, 131.3, 130.2, 127.7, 126.1, 125.5, 123.2, 111.3, 107.5, 106.4, 97.9, 61.1, 60.9, 55.9, 54.1, 52.3, 47.0, 42.0. Anal. Calculated for $C_{25}H_{23}ClN_4O_8$: C, 55.3; H, 4.3; N, 10.3. Found: C, 55.4; H, 4.1; N, 10.3%.

Example KK: Preparation of methyl 5-amino-1-(chloromethyl)-3-[(5,6,7-trimethoxyindol-2-yl)carbonyl]-1,2-dihydro-3H-pyrrolo[3,2-e]indole-7-carboxylate (32a). A solution of 31 (559 mg, 1.0 mmol) in THF (100 mL) with $PtO_2$ (0.10 g, 0.44 mmol) was hydrogenated at 50 psi for 30 min. The catalyst was filtered off, the filtrate evaporated, and the residue triturated with EtOAc to give 32a as a yellow-orange solid (404 mg, 76%), mp 190–196° C. (dec.). The mother liquor was evaporated to give more 32a (111 mg, 21%). $^1$NMR [($CD_3$)$_2$SO] δ 11.62 (d, J=1.7 Hz, 1 H, NH), 11.30 (d, J=1.6 Hz, 1 H, NH), 7.51 (br s, 1 H), 7.21 (s, 1 H), 6.95 (s, 2 H), 5.63 (br s, 2 H, $NH_2$), 4.62 (dd, J=10.7, 9.4 Hz, 1 H, H-2), 4.29 (dd, J=11.0, 4.0 Hz, 1 H, H-2), 4.05 (dd, J=10.8, 3.6 Hz, 1 H, CH$_2$Cl), 4.01–3.94 (m, 1 H, H-1), 3.93 (s, 3 H, OMe), 3.89 (s, 3 H, OMe), 3.83 (dd, J=10.8, 7.6 Hz, 1 H, CH$_2$Cl), 3.81 (s, 3 H, OMe), 3.79 (s, 3 H, OMe). Anal. Calculated for C$_{25}$H$_{25}$ClN$_4$O$_6$.0.5 EtOAc: 58.2; H, 5.2; N, 10.1. Found: C, 58.2; H, 5.3; N, 10.1%.

Example LL: Preparation of methyl 1-(chloromethyl)-5-methylamino-3-[(5,6,7-trimethoxyindol-2-yl)carbonyl]-1,2-dihydro-3H-pyrrolo[3,2-e]indole-7-carboxylate (32b). Freshly prepared acetic formic anhydride [40 μL of a solution prepared from formic acid (1.22 mL, 32 mmol) and acetic anhydride (2.45 mL, 26 mmol)] was added to a solution of 32a (94 mg, 0.18 mmol) in THF (10 mL) under nitrogen at 20° C. The solution was stirred for 2 h, then evaporated. The residue was redissolved in THF (8 mL) under nitrogen, borane-dimethyl sulfide (45 μL, 0.45 mmol) added, and the yellow solution was stirred at reflux for 30 min. The mixture was cooled, MeOH and H$_2$O were added, and the mixture was evaporated. The residue was diluted with H$_2$O and extracted with EtOAc (×2). The extracts were washed with H$_2$O, dried (Na$_2$SO$_4$) and evaporated. Chromatography (50–60% EtOAc-petroleum ether) followed by recrystallization from PhH gave 32b as a yellow solid (11 mg, 11%), mp 201–205° C. (dec.). $^1$H NMR [(CD$_3$)$_2$SO] δ 11.61 (s, 1 H, NH), 11.34 (s, 1 H, NH), 7.42 (v br s, 1 H, H-4), 7.23 (s, 1 H), 6.96 (s, 2 H), 6.06 (s, 1H, NCH), 4.64 (t, J=9.6 Hz, 1 H, H-2), 4.33 (dd, J=11.0, 3.6 Hz, 1 H, H-2), 4.06 (dd, J=10.5, 3.4 Hz, 1 H, CH$_2$Cl), 4.05–3.96 (m, 1 H, H-1), 3.91 (s, 3 H, OMe), 3.88 (s, 3 H, OMe), 3.88–3.83 (m, 1 H, CH$_2$Cl), 3.81 (s, 3 H, OMe), 3.78 (s, 3 H, OMe), 2.81 (s, 3 H, NMe). Anal. Calculated for C$_{26}$H$_{27}$ClN$_4$O$_6$.H$_2$O: C, 57.3; H, 5.4; N, 10.3. Found: C, 57.2; H, 5.4; n, 10.4%.

Example MM: Preparation of methyl 1-(chloromethyl)-5-dimethylamino-3-[(5,6,7-trimethoxyindol-2-yl)carbonyl]-1,2-dihydro-3H-pyrrolo[3,2-e]indole-7-carboxylate (32c). Sodium cyanoborohydride (40 mg, 0.6 mmol) then aq HCl (2N, 0.4 mL) were added to a solution of 32a (111 mg, 0.22 mmol) and formaldehyde (0.17 mL of a 40% w/v aq solution, 2.3 mmol) in THF (15 mL) and the pale orange solution stirred at 20° C. for 100 min. The THF evaporated and the residue was diluted with H$_2$O and extracted with CH$_2$Cl$_2$ (×2). The extracts were dried (Na$_2$SO$_4$) and evaporated. Chromatography (1% MeOH-CHCl$_3$) followed by crystallization from PhH-petroleum ether gave 32c as a cream powder (33 mg, 28%), mp 200–202° C. (dec.). $^1$H NMR [(CD$_3$)$_2$SO] δ 11.64 (s, 1 H, NH), 11.38 (s, 1 H, NH), 7.92 (v br s, 1 H, H-4), 7.34 (s, 1 H), 6.99 (s, 1 H), 6.97 (s, 1 H), 4.67 (t, J=9.6 Hz, 1 H, H-2), 4.37 (dd, J=11.0, 3.5 Hz, 1 H, H-2), 4.16–4.08 (m, 2 H), 3.96 (dd, J=11.8, 8.2 Hz, 1 H), 3.92 (s, 3 H, OMe), 3.87 (s, 3 H, OMe), 3.82 (s, 3 H, OMe), 3.79 (s, 3 H, OMe), 2.78 (s, 6 H, NMe$_2$). Anal. Calculated for C$_{27}$H$_{29}$ClN$_4$O$_6$: C, 59.9; H, 5.4; N, 10.4. Found: C, 60.3; H, 5.6; N, 10.3%.

Example NN: Preparation of methyl 1-(chloromethyl)-5-[(4-nitrobenzyloxycarbonyl)-amino]-3-[(5,6,7-trimethoxyindol-2-yl)carbonyl]-1,2-dihydro-3H-pyrrolo[3,2-e]indole-7-carboxylate (32d). 4-Nitrobenzyl chloroformate (43 mg, 0.20 mmol) was added to a solution of 32a (92 mg, 0.18 mmol) in pyridine (2 mL) and the mixture stirred at 20° C. After 30 min more 4-nitrobenzyl chloroformate (43 mg, 0.20 mmol) was added, and after a further 5 min the pyridine was evaporated. The residue was diluted with aq HCl (1N) and extracted with EtOAc (×2), and the extracts were dried (Na$_2$SO$_4$) and evaporated. The resulting solid was dissolved in hot THF and the solution evaporated onto silica. Chromatography (60% EtOAc-petroleum ether) and trituration with THF gave 32d as a cream solid (22 mg, 18%), mp 257–258° C. $^1$H NMR [(CD$_3$)$_2$SO] δ 11.86 (s, 1 H, NH), 11.37 (s, 1 H, NH), 9.82 (s, 1 H, NH), 8.89 (s, 1 H, H-4), 8.29 (d, J=8.6 Hz, 2 H, H-4",5"), 7.75 (d, J=8.6 Hz, 2 H, H-2",6"), 7.38 (s, 1 H, H-8), 7.01 (s, 1 H, H-3'), 6.96 (s, 1 H, H-4'), 5.37 (s, 2 H, CH$_2$Ar), 4.71 (t, J=10.2 Hz, 1 H, H-2), 4.38 (dd, J=11.0, 4.2 Hz, 1 H, H-2), 4.19–4.12 (m, 1 H, H-1), 4.11 (dd, J=10.9, 3.3 Hz, 1 H, CH$_2$Cl), 4.01 (dd, J=10.8, 6.6 Hz, 1 H, CH$_2$Cl), 3.93 (s, 3 H, OMe), 3.91 (s, 3 H, OMe), 3.82 (s, 3 H, OMe), 3.79 (s, 3 H, OMe). Anal. Calculated for C$_{33}$H$_{30}$ClN$_5$O$_{10}$: C, 57.3; H, 4.4; N, 10.1. Found: C, 57.4; H, 4.4; N, 10.1%.

The following page provides examples of the biological activity of compounds of the invention.

Biological Activity

Compounds of the invention were tested for cytotoxicity against four different cell lines, all of which are widely available in the art. AA8 is a wild type rodent cell line. UV4 is a mutant AA8 cell line defective in excision repair, and hypersensitive to many alkylating agents. EMT6 is a widely-used rodent line. SKOV is a human ovarian cell line.

Cell culture assays were performed in 96-well microtitre trays. Compounds of the invention were added in culture medium, using serial two-fold dilutions to provide duplicate cultures at five different concentrations for each of eight drugs (plus eight controls) per tray. Drugs were dissolved in water or DMSO immediately prior to addition to the cell culture. After 4 hours, medium, and the trays were incubated for a further three days. Cell density was then determined by staining with methylene blue as described previously (Finlay, G. J., et al, *Anal. Biochm.* 1984, 139, 272–277) and the IC$_{50}$ was calculated as the drug concentration providing 50% inhibition of growth relative to the controls.

The activities of compounds of the invention are shown in Table 2.

TABLE 2

| No. | Form | AA8 IC$_{50}$(nM) | UV4 IC$_{50}$(nM) | EMT6 IC$_{50}$(nM) | SKOV3 IC$_{50}$(nM) |
|---|---|---|---|---|---|
| 15a | A | 0.45 | 0.28 | 0.27 | 1.0 |
| 15aR | A | 13.6 | 2.6 | 7.0 | 7.8 |
| 15aS | A | 0.2 | 0.1 | 0.1 | 0.5 |
| 15b | A | 2.4 | 1.0 | 0.8 | 3.0 |
| 15c | A | 12.5 | 7.6 | 5.2 | 18 |
| 15d | A | 1.2 | 0.8 | 0.9 | 1.8 |
| 15e | A | 3.5 | 1.4 | 0.9 | 6.4 |
| 15h | B | >2 | 1.3 | 1.3 | >2 |
| 15i | C | 31 | 16 | 5.9 | 22 |
| 15j | D | 374 | 253 | 212 | 49 |
| 15l | E | 0.3 | 0.4 | 0.2 | 0.6 |
| 15o | F | 660 | 665 | 233 | 1330 |
| 15p | A | 0.1 | 0.1 | 0.1 | 0.3 |
| 15q | A | 5.6 | 3.7 | 3.8 | 16 |
| 32a | G | 17 | 1.7 | 5.6 | 14 |
| 32b | G | 2.4 | 0.7 | 0.8 | 1.9 |
| 32c | G | 12 | 3.3 | 5.2 | 12 |

Compounds of the invention were further tested against human cell lines (Nr+ in Table 3) transfected with a gene encoding a bacterial nitroreductase (NR) enzyme to test for activation of compounds of the invention with NR. Untransfected control cells (NR− in Table 3) were used as control. The cells used were the human colon NR− (wild-type) line WIDR and its transfected NR+ counterpart WC14.10; and the human ovarian NR− (wild-type) line SKOV3 together with its NR+ (transfected) counterpart SC3.2. The results are shown in Table 3, which also indicates the ratios of IC50s. These are intra-experiment values, and may differ slightly from those calculated from the given NR− and NR+ values.

TABLE 3

| no./form | | Human colon lines | | | Human ovarian lines | | |
|---|---|---|---|---|---|---|---|
| | | NR− | NR+ | ratio | NR− | NR+ | ratio |
| 14a | A | 1.3 | 0.38 | 3.4 | 1.6 | 0.14 | 12 |
| 14aR | A | >20 | >20 | ND | >20 | 0.3 | >60 |
| 14aS | A | 0.35 | 0.09 | 4.2 | 0.4 | 0.04 | 9.5 |
| 14b | A | 0.39 | 0.21 | 1.8 | 0.40 | 0.39 | 1.0 |
| 14c | A | 1.6 | 0.36 | 4.4 | 4.3 | 0.25 | 17 |
| 14d | A | 0.74 | 0.29 | 2.6 | 0.58 | 0.15 | 3.9 |
| 14e | A | 0.37 | 0.13 | 2.8 | 1.0 | 0.09 | 11 |
| 14h | B | 5.5 | 7.7 | 0.7 | 13.5 | 15.6 | 0.8 |
| 14i | C | 2.2 | 0.6 | 3.7 | 4.3 | 0.39 | 11 |
| 14j | D | 27.2 | 4.6 | 5.9 | 29.2 | 0.83 | 35 |
| 14l | E | 0.14 | 0.08 | 1.8 | 0.13 | 0.04 | 3.3 |
| 14o | F | 0.41 | 0.06 | 6.8 | 0.41 | 0.05 | 8.2 |
| 15r | A | 0.39 | 0.012 | 33 | 0.062 | 0.0054 | 11.5 |
| 31 | G | 0.4 | 0.01 | 33 | 0.06 | 0.005 | 12 |
| 32d | G | 0.49 | 0.26 | 2.3 | 1.1 | 0.27 | 5.5 |

The results of Table 2 and 3 show that: (a) the novel compounds of formula 1 in which Y=NH$_2$ have substantial cytotoxicity in a range of animal and human tumour cell lines, and (b) that many of the compounds of formula 1 in which Y=NO$_2$ or is replaced by a 4-nitrobenzyl carbamates [formula II, P=IIb] have substantial selective cytotoxicity towards human cell lines incorporating the *E. coli* nitroreductase gene and expressing the corresponding enzyme.

What is claimed is:

1. A compound of the formula (I):

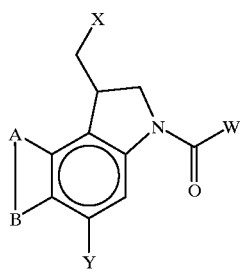

(I)

wherein:

X is halogen or OSO$_2$R, where R represents H or lower alkyl (with from one to four carbon atoms) optionally substituted with hydroxyl or amino groups, the amino groups being optionally substituted by one or two C$_{1-4}$alkyl groups;

Y is NO$_2$, NHOH, N$_3$, NHR, NRR, N=NR, N(O)RR, NHSO$_2$R, N=NPhR, SR or SSR, where Ph is a benzene ring and R is defined as above, but that in the case where Y is N=NR or SSR, then R can also be another moiety of general formula I;

W is selected from the structures of formulae (Ia, Ib or Ic):

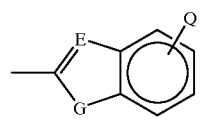

(Ia)

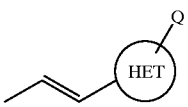

(Ib)

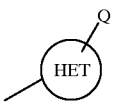

(Ic)

where E is —N= or —CH=, G is O, S, or NH, and Q is either (a) absent or independently one to three of R, OR, NRR, NO$_2$, CONHR, NHCOR, where R is independently as defined above or (b) is an additional group of formulae (Ia, Ib or Ic) and HET represents a 5- or 6-membered carbocycle or heterocycle containing one or two atoms selected from N, O and S;

A and B collectively represent the fused benzene or 2-CO$_2$R pyrrole ring, where R is as defined above;

or a physiologically functional derivative thereof.

2. A compound according to claim 1 of the formula (II):

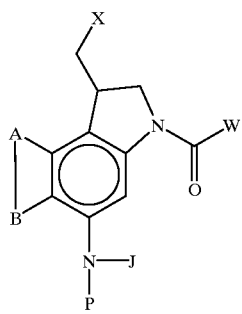

(II)

where J is OH or R, and P is a group which is a substrate for a nitroreducatase or carboxypeptidase enzyme such that one of said enzymes is able to bring about removal of the group P;

or a physiologically functional derivative thereof.

3. A compound according to claim 2 wherein the group P is selected from moieties of the formulae (IIa), (IIb), (IIc) or (IId):

—C(O)—(CZ$_2$)$_n$—Ph (IIa)

—C(O)—O—CH$_2$—Ph (IIb)

—C(O)—NH—C(COOH)—(CH$_2$)$_2$—COOH (IIc)

—C(O)—O—CH$_2$—Phe—L—C(O)—NH—C(COOH)—CH$_2$—COOH (IId)

wherein each occurrence of Z is independently H or Me, n is 1 or 2, Ph is a phenyl moiety substituted in the moiety of (IIa) by a nitro group at the 2-position, and substituted in the moiety of (IIb) by a nitro group in the 2- or 4-position, Phe is a phenylene (C$_6$H$_4$) ring in which the group —L, which is O or NH, is para to the group —O—CH$_2$, the groups Ph and Phe being further optionally substituted by a group R$^1$ which may be a group R, CONHR, NHCOR, NHR, OR or SO$_2$R.

4. A compound according to claim 3 in which R$^1$ represents H or a group CONHR.

5. A compound according to claim 1 in which X represents Cl.

6. A compound according to any one of claim 1 in which W represents a group of the formula Ia, E represents —CH=, G represents NH, and Q represents three OMe groups.

7. A compound according to claim 1 of the formula (III):

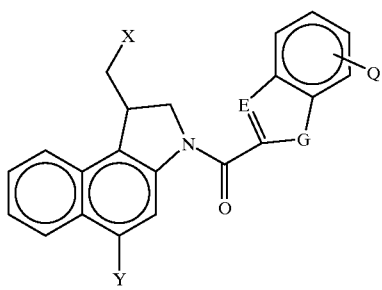

(III)

or a physiologically functional derivative thereof.

8. A compound according to claim 1 of the formula (IV):

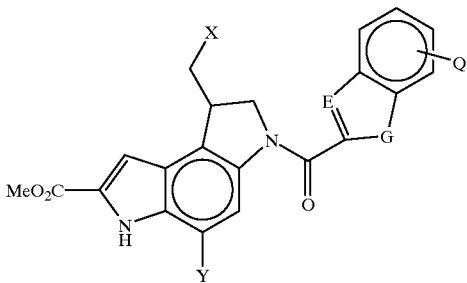

(IV)

9. A compound selected from the group consisting of:

1-Chloromethyl-5-nitro-3-[5,6,7-trimethoxyindol-2-yl)-carbonyl]-1,2-dihydro-3H-benz[e]indole;

1-(Chloromethyl)-3-[[7-[2-(dimethylamino)ethoxy]-5-methoxyindol-2-yl]carbonyl]-5-nitro-1,2-dihydro-3H-benz[e]indole;

1-(Chloromethyl)-3-[[6-[2-(dimethylamino)ethoxy]-5-methoxyindol-2-yl]carbonyl]-5-nitro-1,2-dihydro-3h-benz[e]indole;

1-(Chloromethyl)-3-[(E)-3-methoxycinnamoyl]-5-nitro-1,2-dihydro-3H-benz[e]indole;

(R)-1-(Chloromethyl)-5-nitro-3-[(5,6,7-trimethoxyindol-2-yl)carbonyl]-1,2-dihydro-3H-benz[e]indole;

(S)-1-(Chloromethyl)-5-nitro-3-[(5,6,7-trimethoxyindol-2-yl)carbonyl]-1,2-dihydro-3H-benz[e]indole; and Methyl 1-(chloromethyl)-5-nitro-3-[(5,6,7-trimethoxyindol-2-yl)carbonyl]-1,2-dihydro-3H-pyrrolo[3,2-e]indole-7-carboxylate;

or a physiologically functional derivative thereof.

10. A compound selected from the group consisting of;

5-Amino-1-(chloromethyl)-3-[(5,6,7-trimethoxyindol-2-yl)carbonyl]-1,2-dihydro-3H-benz[e]indole;

1-(Chloromethyl)-5-methylamino-3-[(5,6,7-trimethoxyindol-2-yl)carbonyl]-1,2-dihydro-3H-benz[e]indole;

5-Amino-1-(chloromethyl)-3-[[7-[2-dimethylamino)ethoxy]-5-methoxyindol-2-yl]carbonyl]-1,2-dihydro-3H-benz[e]indole;

5-Amino-1-(chloromethyl)-3-[[6-[2-dimethylamino)ethoxy]-5-methoxyindol-2-yl]carbonyl]-1,2-dihydro-3H-benz[e]indole;

5-Amino-1-(chloromethyl)-3-[[7-[2-dimethylamino)ethoxy]-5-methoxyindol-2-yl]carbonyl]-1,2-dihydro-3H-benz[e]indole;

5-Amino-1-[(E)-4-butyrylamino-1-methyl-2-pyrroleacryloyl]-1-(chloromethyl)-1,2-dihydro-3H-benz[e]indole;

5-Amino-1-(chloromethyl)-3-[(E)-3-methoxycinnamoyl]-1,2-dihydro-3H-benz[e]indole;

(R)-5-Amino-1-(chloromethyl)-3-[(5,6,7-trimethoxyindol-2-yl)carbonyl]-1,2-dihydro-3H-benz[e]indole;

(S)-5-Amino-1-(chloromethyl)-3-[(5,6,7-trimethoxyindol-2-yl)carbonyl]-1,2-dihydro-3H-benz[e]indole;

Methyl 5-amino-1-(chloromethyl)-3-[(5,6,7-trimethoxyindol-2-yl)carbonyl]-1,2-dihydro-3H-pyrrolo[3,2-e]indole-7-carboxylate;

Methyl 1-(chloromethyl)-5-methylamino-3-[(5,6,7-trimethoxyindol-2-yl)carbonyl]-1,2-dihydro-3H-pyrrolo[3,2-e]indole-7-carboxylate; and Methyl 1-(chloromethyl)-5-dimethylamino-3-[(5,6,7-trimethoxyindol-2-yl)carbonyl]-1,2-dihydro-3H-pyrrolo[3,2-e]indole-7-carboxylate;

or a physiologically functional derivative thereof.

11. A compound selected from the group consisting of:

Methyl 1-(chloromethyl)-5-[(4-nitrobenzyloxycarbonyl)amino]-3-[(5,6,7-trimethoxyindol-2-yl)carbonyl]-1,2-dihydro-3H-pyrrolo[3,2-e]indole-7-carboxylate; and 1-(Chloromethyl)-5-[(4-nitrobenzyloxycarbonyl)amino]-3-[(5,6,7-trimethoxyindol-2-yl)carbonyl]-1,2-dihydro-3H-benz[e]indole;

or a physiologically functional derivative thereof.

12. A two component system for the treatment of neoplastic disease which comprises:

(i) a vector encoding and capable of expressing a nitroreductase enzyme in a tumour cell; and (ii) a compound according to claim 2, 3, 9 or 11.

13. A two component system for the treatment of neoplastic disease which comprises:

(i) a tumour-directed antibody linked to a nitroreductase enzyme; and (ii) a compound according to claim 2.

14. A composition comprising a compound according to any one of claims 1 to 11 together with a pharmaceutically acceptable carrier or diluent.

15. A compound according to claim 1 for use in a method of treatment of the human or animal body.

16. A method of treating neoplastic disease which comprises administering to a patient in need of treatment an effective amount of a compound according to claim 1.

17. A method of treating neoplastic disease which comprises administering to a patient in need of treatment an effective amount of a system according to claim 12.

18. A method of treating neoplastic disease which comprises administering to a patient in need of treatment an effective amount of a composition according to claim 14.

* * * * *